US010322949B2

(12) United States Patent
Lipkens et al.

(10) Patent No.: US 10,322,949 B2
(45) Date of Patent: Jun. 18, 2019

(54) TRANSDUCER AND REFLECTOR CONFIGURATIONS FOR AN ACOUSTOPHORETIC DEVICE

(71) Applicant: FLODESIGN SONICS, INC., Wilbraham, MA (US)

(72) Inventors: Bart Lipkens, Hampden, MA (US); Walter M. Presz, Jr., Wilbraham, MA (US); Kedar Chitale, Newton, MA (US); Brian McCarthy, Ludlow, MA (US); Benjamin Ross-Johnsrud, Wilbraham, MA (US); Thomas J. Kennedy, III, Wilbraham, MA (US); Dane Mealey, Springfield, MA (US); Brian Dutra, Rockland, MA (US); David Sokolowski, Worcester, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 67 days.

(21) Appl. No.: 15/490,878

(22) Filed: Apr. 18, 2017

(65) Prior Publication Data
US 2017/0217794 A1    Aug. 3, 2017

Related U.S. Application Data

(63) Continuation-in-part of application No. 14/678,841, filed on Apr. 3, 2015, now Pat. No. 9,623,348, which
(Continued)

(51) Int. Cl.
*C02F 1/36* (2006.01)
*B06B 1/06* (2006.01)
(Continued)

(52) U.S. Cl.
CPC ............... *C02F 1/36* (2013.01); *B01D 17/04* (2013.01); *B01D 17/041* (2013.01);
(Continued)

(58) Field of Classification Search
CPC .... B01D 29/115; B01D 29/865; B01D 29/52; B01D 37/00; B01D 2201/0415;
(Continued)

(56) References Cited

U.S. PATENT DOCUMENTS 2,473,971 A    6/1949  Ross
2,667,944 A    2/1954  Crites
(Continued)

FOREIGN PATENT DOCUMENTS

AU    2002236405      9/2002
CN    104722106 B     4/2016
(Continued)

OTHER PUBLICATIONS

Alvarez et al.; Shock Waves, vol. 17, No. 6, pp. 441-447, 2008.
(Continued)

*Primary Examiner* — Walter D. Griffin
*Assistant Examiner* — Cameron J Allen
(74) *Attorney, Agent, or Firm* — Richard M. Klein, Esq.; Fay Sharpe, LLP

(57) ABSTRACT

Separation of particles or droplets from a host fluid may be achieved using a transducer and/or reflector that is a thin, non-planar structure. The thin non-planar structure improves operation of an acoustic standing wave generated by an acoustic transducer. The structure may operate as a pressure release boundary and may be constructed as plastic film.

20 Claims, 34 Drawing Sheets

Related U.S. Application Data is a continuation-in-part of application No. 14/026,413, filed on Sep. 13, 2013, now Pat. No. 9,458,450, which is a continuation-in-part of application No. 13/844,754, filed on Mar. 15, 2013, now Pat. No. 10,040,011, application No. 15/490,878, which is a continuation-in-part of application No. 15/206,244, filed on Jul. 9, 2016.

(60) Provisional application No. 61/975,035, filed on Apr. 4, 2014, provisional application No. 61/611,159, filed on Mar. 15, 2012, provisional application No. 61/611,240, filed on Mar. 15, 2012, provisional application No. 61/754,792, filed on Jan. 21, 2013, provisional application No. 61/708,641, filed on Oct. 2, 2012, provisional application No. 62/190,715, filed on Jul. 9, 2015.

(51) Int. Cl.

| | | |
|---|---|---|
| *B01D 17/04* | (2006.01) | |
| *C02F 1/40* | (2006.01) | |
| *B01D 19/00* | (2006.01) | |
| *B01D 21/28* | (2006.01) | |
| *C12M 1/42* | (2006.01) | |
| *G10K 11/28* | (2006.01) | |
| *C12N 1/02* | (2006.01) | |
| *C12N 13/00* | (2006.01) | |
| *C12M 1/00* | (2006.01) | |
| *H01L 41/09* | (2006.01) | |

(52) U.S. Cl.
CPC ....... *B01D 17/044* (2013.01); *B01D 19/0078* (2013.01); *B01D 21/28* (2013.01); *B06B 1/0622* (2013.01); *B06B 1/0644* (2013.01); *C02F 1/40* (2013.01); *C12M 35/04* (2013.01); *C12N 1/02* (2013.01); *C12N 13/00* (2013.01); *G10K 11/28* (2013.01); *C12M 47/02* (2013.01); *H01L 41/0913* (2013.01)

(58) Field of Classification Search
CPC ...... B01D 2201/0446; B01D 2201/127; C02F 1/30; C02F 1/32; C02F 1/46
See application file for complete search history.

(56) References Cited

U.S. PATENT DOCUMENTS

| | | |
|---|---|---|
| 3,372,370 A | 3/1968 | Cyr |
| 3,555,311 A | 1/1971 | Weber |
| 4,055,491 A | 10/1977 | Porath-Furedi |
| 4,065,875 A | 1/1978 | Srna |
| 4,118,649 A | 10/1978 | Schwartzman et al. |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,254,661 A | 3/1981 | Kossoff et al. |
| 4,320,659 A | 3/1982 | Lynnworth et al. |
| 4,344,448 A | 8/1982 | Potts |
| 4,398,325 A | 8/1983 | Piaget et al. |
| 4,552,669 A | 11/1985 | Sekellick |
| 4,666,595 A | 5/1987 | Graham |
| 4,673,512 A | 6/1987 | Schram |
| 4,699,588 A | 10/1987 | Zinn et al. |
| 4,743,361 A | 5/1988 | Schram |
| 4,759,775 A | 7/1988 | Peterson et al. |
| 4,800,316 A | 1/1989 | Wang |
| 4,821,838 A | 4/1989 | Chen |
| 4,836,684 A | 6/1989 | Javorik et al. |
| 4,860,993 A | 8/1989 | Goode |
| 4,878,210 A | 10/1989 | Mitome |
| 4,983,189 A | 1/1991 | Peterson et al. |
| 5,059,811 A | 10/1991 | King et al. |
| 5,062,965 A | 11/1991 | Bernou et al. |
| 5,085,783 A | 2/1992 | Feke et al. |
| 5,164,094 A | 11/1992 | Stuckart |
| 5,225,089 A | 7/1993 | Benes et al. |
| 5,371,429 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,475,486 A | 12/1995 | Paoli |
| 5,484,537 A | 1/1996 | Whitworth |
| 5,527,460 A | 6/1996 | Trampler et al. |
| 5,560,362 A | 10/1996 | Sliwa, Jr. et al. |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,834,871 A | 11/1998 | Puskas |
| 5,902,489 A | 5/1999 | Yasuda et al. |
| 5,912,182 A | 6/1999 | Coakley et al. |
| 5,947,299 A | 9/1999 | Vazquez et al. |
| 5,951,456 A | 9/1999 | Scott |
| 6,090,295 A | 6/2000 | Raghavarao et al. |
| 6,161,435 A * | 12/2000 | Bond ............... B01D 61/12 210/785 |
| 6,166,231 A | 12/2000 | Hoeksema |
| 6,216,538 B1 | 4/2001 | Yasuda et al. |
| 6,205,848 B1 | 6/2001 | Faber et al. |
| 6,273,262 B1 | 8/2001 | Yasuda et al. |
| 6,332,541 B1 | 12/2001 | Coakley et al. |
| 6,391,653 B1 | 5/2002 | Letcher et al. |
| 6,475,151 B2 | 11/2002 | Koger et al. |
| 6,482,327 B1 | 11/2002 | Mori et al. |
| 6,487,095 B1 | 11/2002 | Malik et al. |
| 6,592,821 B1 | 7/2003 | Wada et al. |
| 6,641,708 B1 | 11/2003 | Becker et al. |
| 6,649,069 B2 | 11/2003 | DeAngelis |
| 6,699,711 B1 | 3/2004 | Hahn et al. |
| 6,727,451 B1 | 4/2004 | Fuhr et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,481 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,674,630 B2 | 3/2010 | Siversson |
| 7,837,040 B2 | 11/2010 | Ward et al. |
| 7,846,382 B2 | 12/2010 | Strand et al. |
| 7,968,049 B2 | 6/2011 | Takahashi et al. |
| 8,075,786 B2 | 12/2011 | Bagajewicz |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |

(56) References Cited

U.S. PATENT DOCUMENTS

| | | |
|---|---|---|
| 8,679,338 B2 | 3/2014 | Rietman et al. |
| 8,691,145 B2 | 4/2014 | Dionne et al. |
| 8,873,051 B2 | 10/2014 | Kaduchak et al. |
| 8,889,388 B2 | 11/2014 | Wang et al. |
| 9,272,234 B2 | 3/2016 | Lipkens et al. |
| 9,357,293 B2 | 5/2016 | Claussen |
| 9,365,815 B2 | 6/2016 | Miyazaki et al. |
| 9,368,110 B1 | 6/2016 | Hershey et al. |
| 9,388,363 B2 | 7/2016 | Goodson et al. |
| 9,391,542 B2 | 7/2016 | Wischnewskiy |
| 9,403,114 B2 | 8/2016 | Kusuura |
| 9,410,256 B2 | 8/2016 | Dionne et al. |
| 9,416,344 B2 | 8/2016 | Lipkens et al. |
| 9,421,553 B2 | 8/2016 | Dionne et al. |
| 9,422,328 B2 | 8/2016 | Kennedy, III et al. |
| 9,457,139 B2 | 10/2016 | Ward et al. |
| 9,457,302 B2 | 10/2016 | Lipkens et al. |
| 9,458,450 B2 | 10/2016 | Lipkens et al. |
| 9,464,303 B2 | 10/2016 | Burke |
| 9,476,855 B2 | 10/2016 | Ward et al. |
| 9,480,375 B2 | 11/2016 | Marshall et al. |
| 9,480,935 B2 | 11/2016 | Mariella, Jr. et al. |
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |
| 9,517,474 B2 | 12/2016 | Mao et al. |
| 9,532,769 B2 | 1/2017 | Dayton et al. |
| 9,533,241 B2 | 1/2017 | Presz, Jr. et al. |
| 9,550,134 B2 | 1/2017 | Lipkens et al. |
| 9,550,998 B2 | 1/2017 | Williams |
| 9,556,271 B2 | 1/2017 | Blumberg et al. |
| 9,556,411 B2 | 1/2017 | Lipkens et al. |
| 9,566,352 B2 | 2/2017 | Holmes et al. |
| 9,567,559 B2 | 2/2017 | Lipkens et al. |
| 9,567,609 B2 | 2/2017 | Paschon et al. |
| 9,572,897 B2 | 2/2017 | Bancel et al. |
| 9,573,995 B2 | 2/2017 | Schurpf et al. |
| 9,574,014 B2 | 2/2017 | Williams et al. |
| 9,580,500 B2 | 2/2017 | Schurpf et al. |
| 9,587,003 B2 | 3/2017 | Bancel et al. |
| 9,597,357 B2 | 3/2017 | Gregory et al. |
| 9,597,380 B2 | 3/2017 | Chakraborty et al. |
| 9,605,074 B2 | 3/2017 | Shah |
| 9,605,266 B2 | 3/2017 | Rossi et al. |
| 9,606,086 B2 | 3/2017 | Ding et al. |
| 9,608,547 B2 | 3/2017 | Ding et al. |
| 9,611,465 B2 | 4/2017 | Handa et al. |
| 9,616,090 B2 | 4/2017 | Conway et al. |
| 9,623,348 B2 | 4/2017 | McCarthy et al. |
| 9,629,877 B2 | 4/2017 | Cooper et al. |
| D787,630 S | 5/2017 | Lipkens et al. |
| 9,644,180 B2 | 5/2017 | Kahvejian et al. |
| 9,645,060 B2 | 5/2017 | Fiering |
| 9,656,263 B2 | 5/2017 | Laurell et al. |
| 9,657,290 B2 | 5/2017 | Dimov et al. |
| 9,662,375 B2 | 5/2017 | Jensen et al. |
| 9,663,756 B1 | 5/2017 | Lipkens et al. |
| 9,670,477 B2 | 6/2017 | Lipkens et al. |
| 9,670,938 B2 | 6/2017 | Beliavsky |
| 9,675,668 B2 | 6/2017 | Bancel et al. |
| 9,675,902 B2 | 6/2017 | Lipkens et al. |
| 9,675,906 B2 | 6/2017 | Lipkens et al. |
| 9,677,055 B2 | 6/2017 | Jones et al. |
| 9,685,155 B2 | 6/2017 | Hershey et al. |
| 9,686,096 B2 | 6/2017 | Lipkens et al. |
| 9,688,958 B2 | 6/2017 | Kennedy, III et al. |
| 9,689,234 B2 | 6/2017 | Gregory et al. |
| 9,689,802 B2 | 6/2017 | Caseres et al. |
| 9,695,063 B2 | 7/2017 | Rietman et al. |
| 9,695,442 B2 | 7/2017 | Guschin et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0121269 A1 | 6/2005 | Namuduri |
| 2005/0145567 A1 | 7/2005 | Quintel et al. |
| 2005/0196725 A1 | 9/2005 | Fu |
| 2006/0037915 A1 | 2/2006 | Strand et al. |
| 2006/0037916 A1 | 2/2006 | Trampler |
| 2006/0050615 A1 | 3/2006 | Swisher |
| 2007/0053789 A1* | 3/2007 | Ricciardi .............. A61L 2/22 422/28 |
| 2007/0053795 A1 | 3/2007 | Laugharn, Jr. et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0067128 A1 | 3/2008 | Hoyos et al. |
| 2008/0105625 A1 | 5/2008 | Rosenberg et al. |
| 2008/0181838 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper et al. |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0048805 A1 | 2/2009 | Kaduchak et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0218913 A1* | 9/2009 | Hirano .............. G10K 9/22 310/326 |
| 2009/0227042 A1 | 9/2009 | Gauer et al. |
| 2009/0045107 A1 | 12/2009 | Ward et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1* | 5/2011 | Dionne .............. A61L 2/025 422/1 |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Wienand et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |

(56) References Cited

U.S. PATENT DOCUMENTS

| | | |
|---|---|---|
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Reitman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0092266 A1* | 4/2013 | Dhuri ............... B01D 19/0063 137/561 R |
| 2013/0115664 A1 | 5/2013 | Khanna et al. |
| 2013/0175226 A1* | 7/2013 | Coussios ............ B01D 21/283 210/748.05 |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2014/0011240 A1 | 1/2014 | Lipkens et al. |
| 2014/0017758 A1 | 1/2014 | Kniep et al. |
| 2014/0102947 A1 | 4/2014 | Baym et al. |
| 2014/0141413 A1 | 5/2014 | Laugham, Jr. et al. |
| 2014/0154795 A1 | 6/2014 | Lipkens et al. |
| 2014/0319077 A1 | 10/2014 | Lipkens et al. |
| 2014/0329997 A1 | 11/2014 | Kennedy, III et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0252317 A1 | 9/2015 | Lipkens et al. |
| 2015/0274550 A1 | 10/2015 | Lipkens et al. |
| 2015/0321129 A1 | 11/2015 | Lipkens et al. |
| 2016/0060615 A1 | 3/2016 | Walther et al. |
| 2016/0089620 A1 | 3/2016 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 | 8/2016 | Lipkens et al. |
| 2016/0237395 A1 | 8/2016 | Lipkens et al. |
| 2016/0252445 A1 | 9/2016 | Yu et al. |
| 2016/0279540 A1 | 9/2016 | Presz, Jr. et al. |
| 2016/0279551 A1 | 9/2016 | Foucault |
| 2016/0312168 A1 | 10/2016 | Pizzi |
| 2016/0314868 A1 | 10/2016 | El-Zahab et al. |
| 2016/0319270 A1 | 11/2016 | Lipkens et al. |
| 2016/0325039 A1 | 11/2016 | Leach et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |
| 2016/0361670 A1 | 12/2016 | Lipkens et al. |
| 2016/0363579 A1 | 12/2016 | Lipkens et al. |
| 2016/0368000 A1 | 12/2016 | Dionne et al. |
| 2016/0369236 A1 | 12/2016 | Kennedy, III et al. |
| 2016/0370326 A9 | 12/2016 | Kaduchak et al. |
| 2017/0000413 A1 | 1/2017 | Clymer et al. |
| 2017/0002060 A1 | 1/2017 | Bolen et al. |
| 2017/0002839 A1 | 1/2017 | Burkland et al. |
| 2017/0007679 A1 | 1/2017 | Maeder et al. |
| 2017/0008029 A1 | 1/2017 | Lipkens et al. |
| 2017/0016025 A1 | 1/2017 | Poirot et al. |
| 2017/0016027 A1 | 1/2017 | Lee et al. |
| 2017/0020926 A1 | 1/2017 | Mata-Fink et al. |
| 2017/0029802 A1 | 2/2017 | Lipkens et al. |
| 2017/0035866 A1 | 2/2017 | Poirot et al. |
| 2017/0037386 A1 | 2/2017 | Jones et al. |
| 2017/0038288 A1 | 2/2017 | Ward et al. |
| 2017/0042770 A1 | 2/2017 | Warner et al. |
| 2017/0044517 A1 | 2/2017 | Lipkens et al. |
| 2017/0049949 A1 | 2/2017 | Gilmanshin et al. |
| 2017/0056448 A1 | 3/2017 | Glick et al. |
| 2017/0058036 A1 | 3/2017 | Ruiz-Opazo et al. |
| 2017/0065636 A1 | 3/2017 | Moriarty et al. |
| 2017/0066015 A1 | 3/2017 | Lipkens et al. |
| 2017/0067021 A1 | 3/2017 | Moriarty et al. |
| 2017/0067022 A1 | 3/2017 | Poirot et al. |
| 2017/0072405 A1 | 3/2017 | Mao et al. |
| 2017/0073406 A1 | 3/2017 | Schurpf et al. |
| 2017/0073423 A1 | 3/2017 | Juillerat et al. |
| 2017/0073638 A1 | 3/2017 | Campana et al. |
| 2017/0073684 A1 | 3/2017 | Rossi et al. |
| 2017/0073685 A1 | 3/2017 | Maeder et al. |
| 2017/0080070 A1 | 3/2017 | Weinschenk et al. |
| 2017/0081629 A1 | 3/2017 | Lipkens et al. |
| 2017/0088809 A1 | 3/2017 | Lipkens et al. |
| 2017/0088844 A1 | 3/2017 | Williams |
| 2017/0089826 A1 | 3/2017 | Lin |
| 2017/0096455 A1 | 4/2017 | Baric et al. |
| 2017/0107536 A1 | 4/2017 | Zhang et al. |
| 2017/0107539 A1 | 4/2017 | Yu et al. |
| 2017/0119820 A1 | 5/2017 | Moriarity et al. |
| 2017/0128523 A1 | 5/2017 | Ghatnekar et al. |
| 2017/0128857 A1 | 5/2017 | Lipkens et al. |
| 2017/0130200 A1 | 5/2017 | Moriarty et al. |
| 2017/0136168 A1 | 5/2017 | Spain et al. |
| 2017/0137491 A1 | 5/2017 | Matheson et al. |
| 2017/0137774 A1 | 5/2017 | Lipkens et al. |
| 2017/0137775 A1 | 5/2017 | Lipkens et al. |
| 2017/0137802 A1 | 5/2017 | Lipkens et al. |
| 2017/0145094 A1 | 5/2017 | Galetto |
| 2017/0151345 A1 | 6/2017 | Shah |
| 2017/0152502 A1 | 6/2017 | Scharenberg et al. |
| 2017/0152503 A1 | 6/2017 | Scharenberg et al. |
| 2017/0152504 A1 | 6/2017 | Scharenberg et al. |
| 2017/0152505 A1 | 6/2017 | Scharenberg et al. |
| 2017/0152527 A1 | 6/2017 | Paschon et al. |
| 2017/0152528 A1 | 6/2017 | Zhang et al. |
| 2017/0158749 A1 | 6/2017 | Cooper et al. |
| 2017/0159005 A1 | 6/2017 | Lipkens et al. |
| 2017/0159007 A1 | 6/2017 | Lipkens et al. |
| 2017/0166860 A1 | 6/2017 | Presz, Jr. et al. |
| 2017/0166877 A1 | 6/2017 | Bayle et al. |
| 2017/0166878 A9 | 6/2017 | Thanos et al. |
| 2017/0166903 A1 | 6/2017 | Zhang et al. |
| 2017/0173080 A1 | 6/2017 | Lee et al. |
| 2017/0173128 A1 | 6/2017 | Hoge et al. |
| 2017/0173498 A9 | 6/2017 | Lipkens et al. |
| 2017/0175073 A1 | 6/2017 | Lipkens et al. |
| 2017/0175125 A1 | 6/2017 | Welstead et al. |
| 2017/0175139 A1 | 6/2017 | Wu et al. |
| 2017/0175144 A1 | 6/2017 | Zhang et al. |
| 2017/0175509 A1 | 6/2017 | Abdel-Fattah et al. |
| 2017/0175720 A1 | 6/2017 | Tang et al. |
| 2017/0183390 A1 | 6/2017 | Springer et al. |
| 2017/0183413 A1 | 6/2017 | Galetto |
| 2017/0183418 A1 | 6/2017 | Galetto |
| 2017/0183420 A1 | 6/2017 | Gregory et al. |
| 2017/0184486 A1 | 6/2017 | Mach et al. |
| 2017/0189450 A1 | 7/2017 | Conway et al. |
| 2017/0190767 A1 | 7/2017 | Schurpf et al. |
| 2017/0191022 A1 | 7/2017 | Lipkens et al. |

FOREIGN PATENT DOCUMENTS

| | | |
|---|---|---|
| DE | 30 27 433 A1 | 2/1982 |
| DE | 32 18 488 A1 | 11/1983 |
| DE | 196 48 519 A1 | 6/1998 |
| DE | 103 19 467 B3 | 7/2004 |
| DE | 10 2008 006 501 A1 | 9/2008 |
| EP | 0 292 470 B1 | 11/1988 |
| EP | 0 167 406 B1 | 7/1991 |
| EP | 0 641 606 | 3/1995 |
| EP | 1 175 931 A1 | 1/2002 |
| EP | 1 254 669 B1 | 11/2002 |
| EP | 1 308 724 A2 | 5/2003 |
| EP | 2 209 545 | 7/2010 |
| GB | 2 420 510 A | 5/2006 |

(56) References Cited

FOREIGN PATENT DOCUMENTS

| JP | 9-136090 | 5/1997 | |
|---|---|---|---|
| KR | 1442486 | 9/2014 | |
| RU | 2085933 | 7/1997 | |
| SU | 629496 | 10/1978 | |
| WO | WO 1987/07178 A1 | 12/1987 | |
| WO | WO 89/11899 A1 | 12/1989 | |
| WO | WO 90/05008 | 3/1990 | |
| WO | WO 97/34643 | 9/1997 | |
| WO | WO 1998/017373 | 4/1998 | |
| WO | WO 98/50133 A1 | 11/1998 | |
| WO | WO 00/41794 | 7/2000 | |
| WO | WO 02/072234 A1 | 9/2002 | |
| WO | WO 02/072236 A1 | 9/2002 | |
| WO | WO 03/089567 | 10/2003 | |
| WO | WO 2004/079716 A1 | 9/2004 | |
| WO | WO 2009/063198 | 5/2009 | |
| WO | WO 2009/111276 A1 | 9/2009 | |
| WO | WO 2009/144709 A1 | 12/2009 | |
| WO | WO 2010/024753 A1 | 4/2010 | |
| WO | WO 2010/040394 A1 | 4/2010 | |
| WO | WO 2011/023949 A2 | 3/2011 | |
| WO | WO 2011/025890 A1 | 3/2011 | |
| WO | WO 2011/027146 A2 | 3/2011 | |
| WO | WO 2011/131947 A2 | 10/2011 | |
| WO | WO 2011/161463 A2 | 12/2011 | |
| WO | WO-2011161463 A2 * | 12/2011 | ........... B01D 21/283 |
| WO | WO 2013/043297 A1 | 3/2013 | |
| WO | WO 2013/055517 A1 | 4/2013 | |
| WO | WO 2013/138797 A1 | 9/2013 | |
| WO | WO 2013/148376 | 10/2013 | |
| WO | WO 2013/159014 A1 | 10/2013 | |
| WO | WO 2014/014941 A1 | 1/2014 | |
| WO | WO 2014/029505 | 2/2014 | |
| WO | WO 2014/046605 A1 | 3/2014 | |
| WO | WO 2014/055219 A2 | 4/2014 | |
| WO | WO 2014/124306 A1 | 8/2014 | |
| WO | WO 2014/153651 | 10/2014 | |
| WO | WO 2015/006730 | 1/2015 | |
| WO | WO 2015/102528 | 7/2015 | |
| WO | WO 2016/124542 | 8/2016 | |
| WO | WO 2016/209082 | 12/2016 | |

OTHER PUBLICATIONS

Benes et al.; Ultrasonic Separation of Suspended Particles, 2001 IEEE Ultrasonics Symposium; Oct. 7-10, 2001; pp. 649-659; Atlanta, Georgia.
Castilho et al.; Animal Cell Technology: From Biopharmaceuticals to Gene Therapy; 11—Animal Cell Separation; 2008.
Castro; Tunable gap and quantum quench dynamics in bilayer graphene; Jul. 13, 2010; Mathematica Summer School.
Chitale et al.; Understanding the Fluid Dynamics Associated with Macro Scale Ultrasonic Separators; Proceedings of Meetings on Acoustics, May 2015.
Cravotto et al.; Ultrasonics Sonochemistry, vol. 15, No. 5, pp. 898-902, 2008.
Garcia-Lopez, et al; Enhanced Acoustic Separation of Oil-Water Emulsion in Resonant Cavities. The Open Acoustics Journal. 2008, vol. 1, pp. 66-71.
Grenvall et al.; Concurrent Isolation of Lymphocytes and Granulocytes Using Prefocused Free Flow Acoustophoresis; Analytical Chemistry; vol. 87; pp. 5596-5604; 2015.
Higginson et al.; Tunable optics derived from nonlinear acoustic effects; Journal of Applied Physics; vol. 95; No. 10; pp. 5896-5904; 2004.
Hill et al.; Ultrasonic Particle Manipulation; Microfluidic Technologies for Miniaturized Analysis Systems, Jan. 2007, pp. 359-378.
Ilinskii et al.; Acoustic Radiation Force on a Sphere in Tissue; AIP Conference Proceedings; 2012.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.
Li et al.; Electromechanical behavior of PZT-brass unimorphs; J. Am. Ceram. Soc. vol. 82; No. 7; pp. 1733-1740, 1999.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; Separation of bacterial spores from flowering water in macro-scale cavities by ultrasonic standing waves; submitted/uploaded to http://arxiv.org/abs/1006.5467 on Jun. 28, 2010.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et al.; An Industrial-Prototype Acoustic Array for Real-Time Emulsion Layer Detection in Oil Storage Tanks; IEEE Sensors Journal, vol. 9, No. 12, Dec. 2009.
Musiak et al.; Design of a Control System for Acoustophoretic Separation, 2013 IEEE 56$^{th}$ International Midwest Symposium on Circuits and Systems (MWSCAS), Aug. 2013, pp. 1120-1123.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Pangu et al.; Droplet transport and coalescence kinetics in emulsions subjected to acoustic fields; Ultrasonics 46, pp. 289-302 (2007).
Phys. Org. "Engineers develop revolutionary nanotech water desalination membrane." Nov. 6, 2006. http://phys.org/news82047372.html.
Ponomarenko et al.; Density of states and zero Landau level probed through capacitance of graphene; Nature Nanotechnology Letters, Jul. 5, 2009; DOI: 10.1038/NNANO.2009.177.
"Proceedings of the Acoustics 2012 Nantes Conference," Apr. 23-27, 2012, Nantes, France, pp. 278-282.
Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.
Seymour et al, J. Chem. Edu., 1990, 67(9), p. 763, published Sep. 1990.
Volpin et al.; Mesh simplification with smooth surface reconstruction; Computer-Aided Design; vol. 30; No. 11; 1998.
Wang et al.; Retention and Viability Characteristics of Mammalian Cells in an Acoustically Driven Polymer Mesh; Biotechnol. Prog. 2004, pp. 384-367 (2004).
Wicklund et al.; Ultrasonic Manipulation of Single Cells; Methods in Molecular Biology; vol. 853; pp. 1777-196; 2012.
Annex to Form PCT/ISA/206—Communication Relating to the Results of the Partial International Search Report dated Jul. 18, 2013.
European Search Report of European Application No. 11769474.5 dated Sep. 5, 2013.
European Search Report of European Application No. 11796470.0 dated Jan. 5, 2016.
European Search Report of European Application No. 13760840.2, dated Feb. 4, 2016.

(56) References Cited

OTHER PUBLICATIONS

European Search Report of European Application No. 13721179.3 dated Mar. 23, 2016.
European Search Report for European Application No. 14749278.9 dated Jan. 13, 2017.
Extended European Search Report for European Application No. EP 12833859.7 dated Mar. 20, 2015.
Extended European Search Report for European Application No. EP 14787587.6 dated Jan. 2, 2017.
International Search Report and Written Opinion for International Application No. PCT/US2011/032181 dated Dec. 20, 2011.
International Search Report and Written Opinion for International Application No. PCT/US2011/040787 dated Feb. 27, 2012.
International Search Report and Written Opinion for International Application No. PCT/US2012/051804 dated Nov. 16, 2012.
International Search Report and Written Opinion for International Application No. PCT/US2013/037404 dated Jun. 21, 2013.
International Search Report and Written Opinion for International Application No. PCT/US2013/032705 dated Jul. 26, 2013.
International Search Report and Written Opinion for International Application No. PCT/US2013/050729 dated Sep. 25, 2013.
International Search Report and Written Opinion for International Application No. PCT/US2013/059640 dated Feb. 18, 2014.
International Search Report and Written Opinion for International Application No. PCT/US2014/015382 dated May 6, 2014.
International Search Report and Written Opinion for International Application No. PCT/US2014/035557 dated Aug. 27, 2014.
International Search Report and Written Opinion for International Application No. PCT/US2014/043930 dated Oct. 22, 2014.
International Search Report and Written Opinion for International Application No. PCT/US2014/046412 dated Oct. 27, 2014.
International Search Report and Written Opinion for International Application No. PCT/US2014/064088 dated Jan. 30, 2015.
International Search Report and Written Opinion for International Application No. PCT/US2015/010595 dated Apr. 15, 2015.
International Search Report and Written Opinion for International Application No. PCT/US2015/019755 dated May 4, 2015.
International Search Report and Written Opinion for International Application No. PCT/US2015/030009 dated Jul. 30, 2015.
International Search Report and Written Opinion for International Application No. PCT/US2015/039125 dated Sep. 30, 2015.
International Search Report and Written Opinion for International Application No. PCT/US2015/053200 dated Dec. 28, 2015.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/031357 dated Jul. 26, 2016.
International Search Report and Written Opinion for International Application No. PCT/US2016/038233 dated Sep. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/044586 dated Oct. 21, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
International Search Report and Written Opinion for International Application No. PCT/US2017/015197 dated Apr. 3, 2017.
International Search Report and Written Opinion for International Application No. PCT/US2017/015450 dated Apr. 10, 2017.
International Search Report and Written Opinion for International Application No. PCT/US2016/047217 dated Apr. 11, 2017.
International Search Report and Written Opinion for International Application No. PCT/US2016/048243 dated Apr. 20, 2017.
International Search Report and Written Opinion for International Application No. PCT/US2017/017788 dated May 8, 2017.
Sony New Release: <http://www.sony.net/SonyInfo/News/Press/201010/10-137E/index.html>.

* cited by examiner

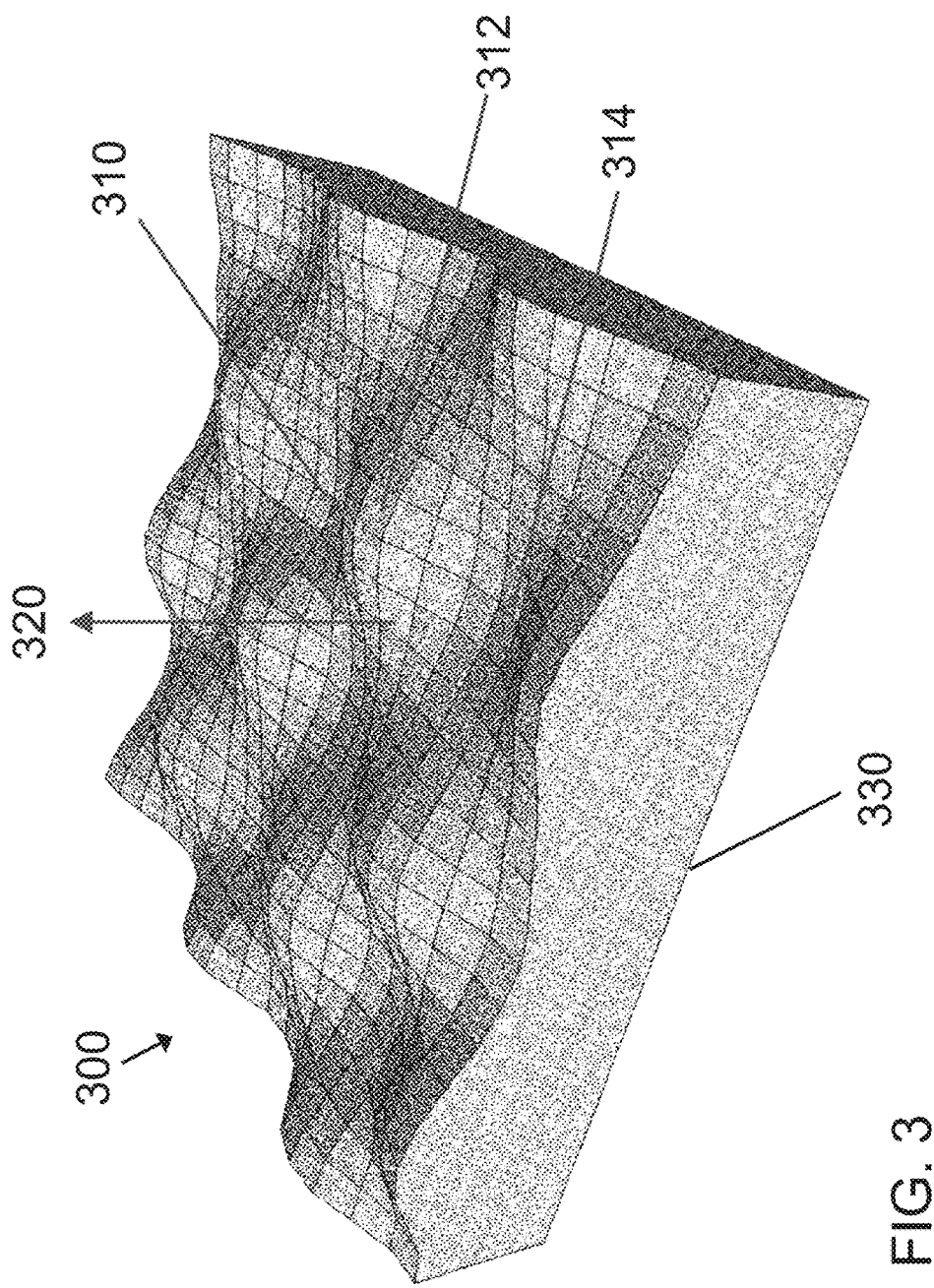

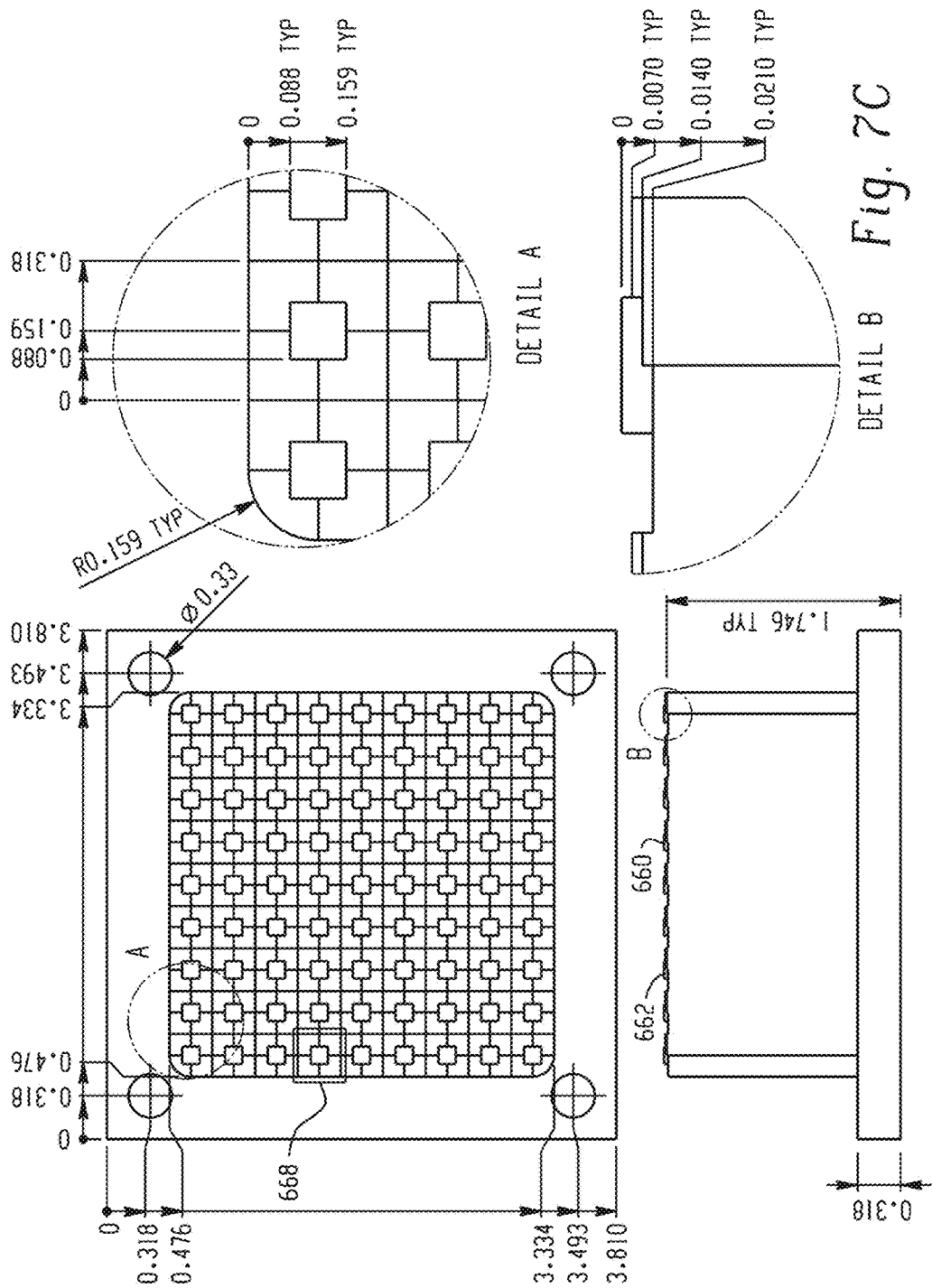

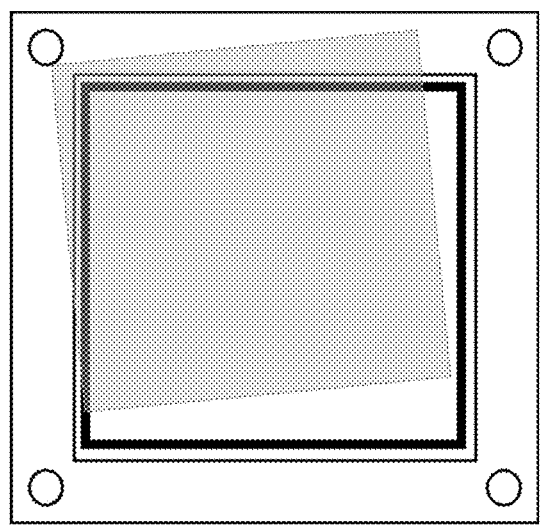
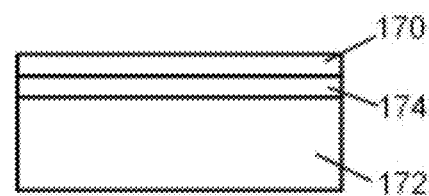
FIG. 24

TRANSDUCER AND REFLECTOR CONFIGURATIONS FOR AN ACOUSTOPHORETIC DEVICE

CROSS-REFERENCE TO RELATED APPLICATIONS

The present application is a continuation-in-part of U.S. patent application Ser. No. 14/678,841, filed Apr. 3, 2015, now U.S. Pat. No. 9,623,348, issued Apr. 18, 2017, which claimed the benefit of U.S. Provisional Patent Application Ser. No. 61/975,035, filed Apr. 4, 2014, and which is a continuation-in-part of U.S. patent application Ser. No. 14/026,413, filed on Sep. 13, 2013, now U.S. Pat. No. 9,458,450, which is a continuation-in-part of U.S. Ser. No. 13/844,754, filed Mar. 15, 2013, which claimed the benefit of U.S. Provisional Patent Application Ser. No. 61/611,159, filed Mar. 15, 2012, and of U.S. Provisional Patent Application Ser. No. 61/611,240, also filed Mar. 15, 2012, and of U.S. Provisional Patent Application Ser. No. 61/708,641, filed on Oct. 2, 2012, and of U.S. Provisional Patent Application Ser. No. 61/754,792, filed Jan. 21, 2013. This application is also a continuation-in-part of U.S. patent application Ser. No. 15/206,244, filed on Jul. 9, 2016, which claims the benefit of U.S. Provisional Patent Application Ser. No. 62/190,715, filed on Jul. 9, 2015. These applications are all hereby incorporated herein by reference in their entireties.

BACKGROUND

The ability to separate a particle/fluid mixture into its separate components is desirable in many applications. Acoustophoresis is the separation of materials using sound waves, which may propagate at ultrasonic frequencies. Standing sound waves, which may have relativity high intensity, can exert forces on particles or secondary fluids in a host or primary fluid when there is a differential in density and/or compressibility, or the acoustic contrast factor. The pressure profile in an acoustic standing wave includes areas of local minimum pressure amplitudes at nodes of the waveform and local maxima at anti-nodes of the waveform. Depending on their density and compressibility, fluid or particles are urged toward and remain at the nodes or anti-nodes of the standing wave in response to the pressure profile. The higher the frequency of the standing wave, the smaller the particles that can be trapped at nodes or anti-nodes of the standing wave.

The fields of biotechnology and bioprocessing have experienced significant growth, some of which has resulted from or fostered improvements in the equipment and technology used. For example, improved equipment and techniques applied to bioreactors have allowed for larger volumes and lower cost for the production of biologically derived materials such as monoclonal antibodies and recombinant proteins. These improvements in manufacturing processes have permitted the creation of new biologically based pharmaceuticals from bioreactor processes.

A modern bioreactor tends to be a complex piece of equipment. In such equipment, a number of parameters are controlled to various degrees of specificity. For example, the bioreactor may regulate fluid flow rates, gas content, temperature, pH and/or oxygen content. All of these parameters can be tuned to allow the cell culture in the bioreactor to be efficient in producing the desired biomolecules from the bioreactor process.

There are several popular techniques for operating a bioreactor and obtaining product. Among these techniques are fed-batch, batch and perfusion processes. The perfusion process is distinguished from the fed-batch and batch processes by its lower capital cost and higher throughput.

In the fed-batch process, a culture to be grown or expanded is seeded in a bioreactor. The gradual addition of a fresh volume of selected nutrients during the growth cycle is used to improve productivity and expansion. The product, which may be, for example, a monoclonal antibody or a recombinant protein, is recovered after the culture is harvested. Separating the cells, cell debris and other waste products from the desired product may be performed using various types of traditional filters for separation. Such filters tend to be relatively expensive to manufacture and become clogged and non-functional as they retain material from the bioreactor as the material is processed. A fed-batch bioreactor process is favored because of its simplicity and also due to carryover knowledge from well-known fermentation processes. However, a fed-batch bioreactor has high start-up costs, and generally has a large volume to obtain a cost-effective amount of product at the end of the growth cycle. The processes for turning over a batch and preparing the bioreactor for a new batch often include large amounts of non-productive downtime.

A perfusion bioreactor processes a continuous supply of fresh media that is fed into the bioreactor while growth-inhibiting byproducts are continuously removed. Nonproductive downtime can be reduced or eliminated with a perfusion bioreactor process. The cell densities achieved in a perfusion culture (30-100 million cells/mL) are typically higher than for fed-batch modes (5-25 million cells/mL). These improvements have led to lower contamination in the harvest and better yields without significant increase in cost. A perfusion bioreactor uses a cell retention system to prevent escape of the culture when byproducts are being removed. The cell retention systems add a level of complexity to the perfusion process, where the process is carefully managed, controlled and maintained for successful operation. Operational issues such as malfunction or failure of the cell retention equipment has previously been a problem with perfusion bioreactors, which has limited their attractiveness in the past.

In each of the bioreactor processes, some type of separator or filter is used to separate cells, cell debris, product or byproducts from the culture media. Acoustophoresis may be used for such separation or filtering.

BRIEF DESCRIPTION

The present disclosure relates, in various embodiments, to acoustophoretic devices and methods of separating a second fluid or a particulate from a host or primary fluid. According to some examples, an acoustic standing wave is generated by an acoustic transducer. The acoustic standing wave has pressure components in two or more dimensions, which effect is sometimes referred to herein as a multi-dimensional acoustic standing wave. In some examples herein, the multi-dimensional acoustic standing wave(s) emanate from a non-planar face of a piezoelectric material. The multi-dimensional nature of the pressure components of the standing wave is used to continuously trap the second fluid or particulate. The trapped secondary fluid or particles cluster, agglomerate, aggregate, clump, or coalesce together, and subsequently rise or settle out of the host fluid due to buoyancy or gravity forces. The non-planar piezoelectric material can be operated at a single frequency to generate a multi-dimensional acoustic standing wave.

Disclosed in various embodiments herein are acoustophoretic devices that include an acoustic chamber with at least one ultrasonic transducer coupled to the acoustic chamber. In some examples, a reflector is located opposite the ultrasonic transducer. The ultrasonic transducer includes a piezoelectric material that can be excited or driven by a signal, such as an electrical signal, for example a voltage signal. The excited piezoelectric material creates a multi-dimensional acoustic standing wave in the acoustic chamber emanating from a non-planar face of the piezoelectric material. The face of the piezoelectric material when at rest (non-excited) may be planar, non-planar, or combinations thereof. For example, the geometry of the face may include multiple facet levels in discrete regions, and be planar in other discrete regions.

In certain embodiments, the non-planar face of the piezoelectric material is poled in a direction substantially perpendicular to a second face of the piezoelectric material. The non-planar face of the piezoelectric material can be defined by a step function or a smooth function.

In certain embodiments, the reflector has a non-planar surface. The surface geometry of the reflector or the piezoelectric material can be defined by a step function or a smooth function, for examples. In certain embodiments, the piezoelectric material may be planar and the reflector has a non-planar surface.

The face of the ultrasonic transducer, the face or entirety of the piezoelectric material and/or the reflector can be shaped as a polygon, regular or irregular, and can be symmetrical or non-symmetrical in shape. For example, the face of the ultrasonic transducer, the face or entirety of the piezoelectric material and/or the reflector can be trapezoidal in shape.

Disclosed herein are methods for separating a second fluid or a particulate from a host or primary fluid by flowing a mixture of the host fluid and the second fluid or particulate through an acoustophoretic device. The acoustophoretic device includes a chamber with an ultrasonic transducer coupled thereto. The acoustophoretic device may include a reflector opposite the ultrasonic transducer. The ultrasonic transducer can produce an ultrasonic wave that travels to the reflector. The reflector reflects the ultrasonic wave back to the transducer, which at certain frequencies, generates a standing wave with spatially stable nodes and antinodes. The ultrasonic transducer is operated to create a multi-dimensional acoustic standing wave in the chamber. The multi-dimensional acoustic standing wave may be generated by a planar, non-planar or combination transducer, and may emanate from a non-planar face of the transducer composed of piezoelectric material. The multi-dimensional acoustic standing wave in the chamber can trap or retain the second fluid or particulate on a continuous basis. The trapped second fluid or particulate agglomerates, aggregates, clumps, or coalesces together, and continuously rises or settles out of the host fluid due to enhanced buoyancy or gravity forces.

The transducer can be driven by a signal, such as an electrical signal, which can be applied as a voltage signal or as a current signal. The signal can be a magnetic signal, an electromagnetic signal, a capacitive signal, or any other type of signal to which the transducer is responsive to permit generation of a multi-dimensional acoustic standing wave. The signal can be a sinusoidal, triangular, pulsed or similar waveform. The signal can have a frequency of from about 100 kHz to about 20 MHz.

In certain embodiments, the mixture of the host fluid and the second fluid or particulate is continuously flowed through the chamber. The second fluid or particulate can include cells that are CHO cells, T-cells or yeast cells. Flow rates through the acoustic chamber can be from about 1 mL per minute to about 50 liters per hour. Example implementations and techniques of the present disclosure are capable of separation efficiencies of 90% or more for cell concentrations from as low as 50,000 cells per milliliter of fluid to 80,000,000 or 100,000,000 cells per milliliter of fluid.

Also disclosed herein are systems and methods for separating microcarriers and cells from a host fluid. Microcarriers are particles with a larger or smaller dimension in the high nanometer range to the high micrometer range. The microcarriers can be composed of microspheres, microparticles and/or nanoparticles, and are sometimes referred to as beads. Microcarriers may be implemented as porous spheres that are used with adherence cells. As used herein, microcarriers or beads are used to refer collectively and/or discretely to the above described items. A mixture containing a host fluid, the microcarriers, and the cells are provided to an acoustophoretic device in which an ultrasonic transducer is actuated to generate an acoustic standing wave. The acoustic standing wave may be a planar or one-dimensional acoustic standing wave, or may be a multi-dimensional acoustic standing wave, or may include elements of both. The acoustic standing wave can be configured to provide a barrier to the microcarriers to prevent them from passing, or to retain the microcarriers within the acoustic field generated by the acoustic standing wave, or to permit the microcarriers to pass. The acoustic standing wave can be configured to provide a barrier to the cells, can retain the cells, or can permit the cells to pass. The mixture can be provided to the acoustophoretic device in a recirculating fluid stream with a tangential flow path that is tangential to the multi-dimensional acoustic standing wave. The acoustic standing wave can be configured with the tangential flow path to form an interface region that provides a barrier to the microcarriers or cells. In an example, the interface region forms a barrier for microcarriers and permits the cells to pass. For example, at least a portion of the cells (e.g., at least 95% of the cells, including up to about 99% of the cells) pass through the acoustic standing wave, and the microcarriers are held back in the recirculating fluid stream at the interface region.

The microcarriers may be any type of bead and may be composed of any useful composition. The microcarriers may be non-functionalized or functionalized. Functionalized microcarriers may include binding materials that can attach to a target material or vice-versa. The microcarriers can be functionalized with various biologic materials on the microcarrier surface, such as antigens, that permit affinity binding of target biological materials. The target materials that can be subject to affinity binding are any type of biological material, including, for example, cells, viruses, virus-like particles, cell vesicles, including exosomes and oncozomes, materials generated by cells, such as by protein synthesis, including proteins, monoclonal antibodies and recombinant proteins, as well as any other biological materials for which affinity binding materials can be provided. In addition, or alternatively, the functionalized microcarriers be functionalized with binding materials for target materials that are not biological materials. The functionalized material applied to the microcarriers may include specific chemistry for organic or inorganic target materials. For example, the beads may be polymeric beads impregnated with a material (such as DTDGA, which can be implemented as N,N,N',N'-tetra-(2-ethylhexyl) dithiodiglycolamide) for separation of metals such as gold or palladium from fluid mixtures, including those that may result from electronic waste solutions.

The microcarriers may have a positive contrast factor. Examples of functionalized microcarriers with a positive contrast factor include polystyrene beads and glass beads. The microcarriers may have a negative contrast factor. Examples of microcarriers with a negative contrast factor include microbubbles and micro-glass spheres. Micro-glass spheres may have a density of 2.4 to 2.8 g per cc, which may be similar to aluminum, and may have a positive contrast factor. Examples of microcarrier material or structure include agarose, polymeric, glass, hollow and gas-filled. Examples of the geometry or shape of the microcarriers include spherical, toroidal, cylindrical and conical.

In certain embodiments of the method, the material in the mixture that can be separated can include cell or microvesicles, for example, exosomes and/or oncosomes. Examples of other material that may be in the mixture for separation include viruses, proteins, recombinant proteins and monoclonal antibodies.

A pressure rise and an acoustic radiation force on cells can be generated at the interface region to clarify the host fluid as it passes through the multi-dimensional acoustic standing wave. In particular embodiments, cells that pass through the acoustic standing wave are recirculated through the device to provide for multiple separation passes. The cells passing through the acoustic standing wave can be collected and/or recirculated, for example by using a flow path with a switch.

In various embodiments herein are acoustophoretic devices with an ultrasonic transducer composed of piezoelectric material and a reflector that includes a faceted surface. The face of the ultrasonic transducer can be planar. The faceted surface of the reflector can include a plurality of facet clusters or a plurality of wells.

In particular embodiments, the multi-dimensional standing wave results in an acoustic radiation force having an axial force component and a lateral force component that are the same order of magnitude. In particular embodiments, the acoustic standing wave may be a multi-dimensional acoustic standing wave that is a three-dimensional acoustic standing wave. The three-dimensional standing wave generates acoustic forces in three dimensions, for example in the direction of wave propagation and in directions that are not aligned with the direction of wave propagation. Examples of such multi-dimensional acoustic standing waves can be found in commonly owned U.S. Pat. No. 9,228,183, the entire contents of which are hereby fully incorporated herein by reference. In other embodiments, the acoustic standing wave can be a planar or one-dimensional acoustic standing wave, where the acoustic forces are aligned with the direction of wave propagation. The acoustic standing wave may be a combination of a planar acoustic standing wave and a multi-dimensional acoustic standing wave, such as where the planar acoustic standing wave and multidimensional acoustic standing wave are super-positioned on each other.

In some example implementations, the reflector is a material with a different acoustic impedance than the material in which the acoustic wave propagates. For example, an acoustic wave may reflect off a fluid such as air or other gases that border the propagation fluid, which may be water or other liquids. A thin material may be provided as a boundary between the two fluids that is formed to be relatively thin and acoustically transparent. The reflector can be formed with a thin material as the boundary, using certain plastic films that are mostly or substantially acoustically transparent, for example. The thin material may be optically transparent. The reflector implemented from the thin material can provide a constant pressure boundary, also known as a free surface. The thin reflector embodiments exposed to acoustic waves are examples of a pressure release surface.

Disclosed in various embodiments is a thin structure that is located opposite an ultrasonic transducer. The thin structure implements a pressure release boundary that acts as a reflector for acoustic energy, including bulk acoustic waves.

In particular embodiments, the thin structure is a plastic film. Examples of materials that the plastic film can be made from include olefins, polyurethanes, polyureas, polyesters, polystyrenes, polyamides, cellulosics, ionomers, polyvinyl chloride, polyvinyl butyral, polyvinylidene fluoride, polyvinylidene chloride, ethylene vinyl acetate, ethylene tetrafluoroethylene, polytetrafluoroethylene, and combinations thereof. More specifically, the plastic film can be a polypropylene.

The thin structure can be optically transparent. The thin structure may be substantially flat. The thin structure may have a thickness that is ½ or less of the wavelength relative to the frequency emitted by the at least one ultrasonic transducer. This thickness may be in the range of 5 or 10 microns to 1 millimeter (mm).

In some embodiments, the ultrasonic transducer may have a face that contacts fluid within a chamber. The face of the transducer may be coated with a wear layer comprising chrome, electrolytic nickel, electroless nickel, p-xylylene, glassy carbon, or urethane.

Also disclosed in various embodiments are systems methods of separating a second fluid or a particulate from a host fluid, in which an acoustic transducer generates a multi-dimensional acoustic standing wave directed at a thin structure located opposite to the acoustic transducer. The systems and methods may include arranging the thin structure opposite the acoustic transducer to provide a pressure release boundary that acts as a reflector.

The particulate may be Chinese hamster ovary (CHO) cells, NS0 hybridoma cells, baby hamster kidney (BHK) cells, insect cells or human cells such as stem cells and T-cells. The mixture may be continuously flowed through a flow chamber in which the acoustic transducer operates to produce a multi-dimensional acoustic standing wave. The standing wave may have an axial force and a lateral force, the lateral force being at least the same order of magnitude as the axial force. The thin structure implemented as a reflector of the acoustic energy may have an acoustic reflection coefficient. The acoustic reflection coefficient may be in the range of from about −0.1 to about −1.0.

A flat-faced piezoelectric crystal can be perturbed in a multi-mode state to generate acoustic standing waves that produce pressure forces in three dimensions. The multi-mode perturbation generates vibration in higher order modes of the piezoelectric crystal. The higher order modes can produce multiple trapping lines in the resulting acoustic standing wave.

The present disclosure relates to the use of ultrasonic acoustic standing waves to achieve trapping, concentration, and separation of suspended-phase components from a host or primary fluid. The suspended phase components may be particles or a secondary fluid. The trapped particles or droplets of the secondary fluid can be separated from the host fluid by reaching a certain size at which buoyancy or gravity forces overcome the trapping forces and the particles or droplets rise or sink out of the acoustic standing waves. The acoustic standing waves may be created by an acoustic transducer, which may be composed of piezoelectric material. The piezoelectric material may be in the form of a crystal, poly-crystal, ceramic crystal or ceramic poly-crystal, collectively referred to herein as a crystal. The piezoelectric material of the transducer is operated with an applied excitation to produce acoustic waves.

The acoustic transducer may be composed of any material that is able to generate a piezo effect, e.g., vibrate when subjected to an excitation. A conventional material that is used to make piezoelectric crystals is lead zirconate titanate (PZT). Piezoelectric ceramics are traditionally a mass of perovskite ceramic crystals composed of a small, tetravalent metal ion (e.g., titanium, zirconium) in a lattice of larger, divalent metal ions (e.g., lead, barium) and oxygen ions.

A piezoelectric PZT crystal can be made by mixing fine powders of the component metal oxides in specific proportions. This mixture is then heated to form a uniform powder. An organic binder is mixed with the metal oxides and formed into desired shapes (e.g., plates, rods, discs). The formed materials are heated at high temperatures that sinter the mixture and form a dense crystalline structure. The sintered parts are then cooled and subsequently shaped or trimmed to desired specifications. Electrodes are applied to the appropriate surfaces of the PZT crystal using processes such as electroless nickel plating or a silver/glass bead mixture coating that is heated and fused on the surface of the crystal.

Excitation of the piezoelectric crystal, such as by an applied electric field or signal, causes the crystal to vibrate and generate pressure waves. The pressure waves can propagate in gasses such as air or in a liquid fluid. A function generator or oscillator may be used to apply a specific frequency or group of frequencies to the piezoelectric crystal such that the pressure waves have a specific frequency. An amplifier may be used to apply higher voltages to the piezoelectric crystal at the frequencies generated by the function generator or oscillator. In some applications, the acoustic transducer is operated with a reflector that reflects the acoustic wave back to the acoustic transducer, thereby setting up an acoustic standing wave.

BRIEF DESCRIPTION OF THE DRAWINGS

The following is a brief description of the drawings, which are presented for the purposes of illustrating the embodiments disclosed herein and are not intended to be limiting.

FIG. 3 illustrates a first embodiment of a non-planar face of a piezoelectric material according to the present disclosure. The non-planar face of the piezoelectric material is defined by a smooth function.

FIG. 7C illustrates a third exemplary configuration of the faceted surface of the reflector of FIG. 6.

In FIG. 14A, the excitation pattern is generated at a frequency of 2.217 MHz. The right-hand scale is in units of 10-9, and ranges from 0.55 to 1 in intervals of 0.05. The maximum value is 2.25×10-9, and the minimum value is 2.18×10e-11.

In FIG. 14B, the excitation pattern is generated at a frequency of 2.302 MHz. The right-hand scale is in units of 10-10, and ranges from 3 to 6 in intervals of 0.5. The maximum value is 1.38×10-9, and the minimum value is 1.64×10e-11.

In FIG. 14C, the excitation pattern is generated at a frequency of 2.32 MHz. The right-hand scale is in units of 10-10, and ranges from 2.5 to 6 in intervals of 0.5. The maximum value is 1.11×10-9, and the minimum value is 1.4×10e-11.

In FIG. 14D, the excitation pattern is generated at a frequency of 2.34 MHz. The right-hand scale is in units of 10-10, and ranges from 3 to 5 in intervals of 0.5. The maximum value is 9.23×10-10, and the minimum value is 8.98×10e-12.

FIG. 24 is a picture of a test ultrasonic transducer having an acoustically transparent film cover.

DETAILED DESCRIPTION

Figure 1:
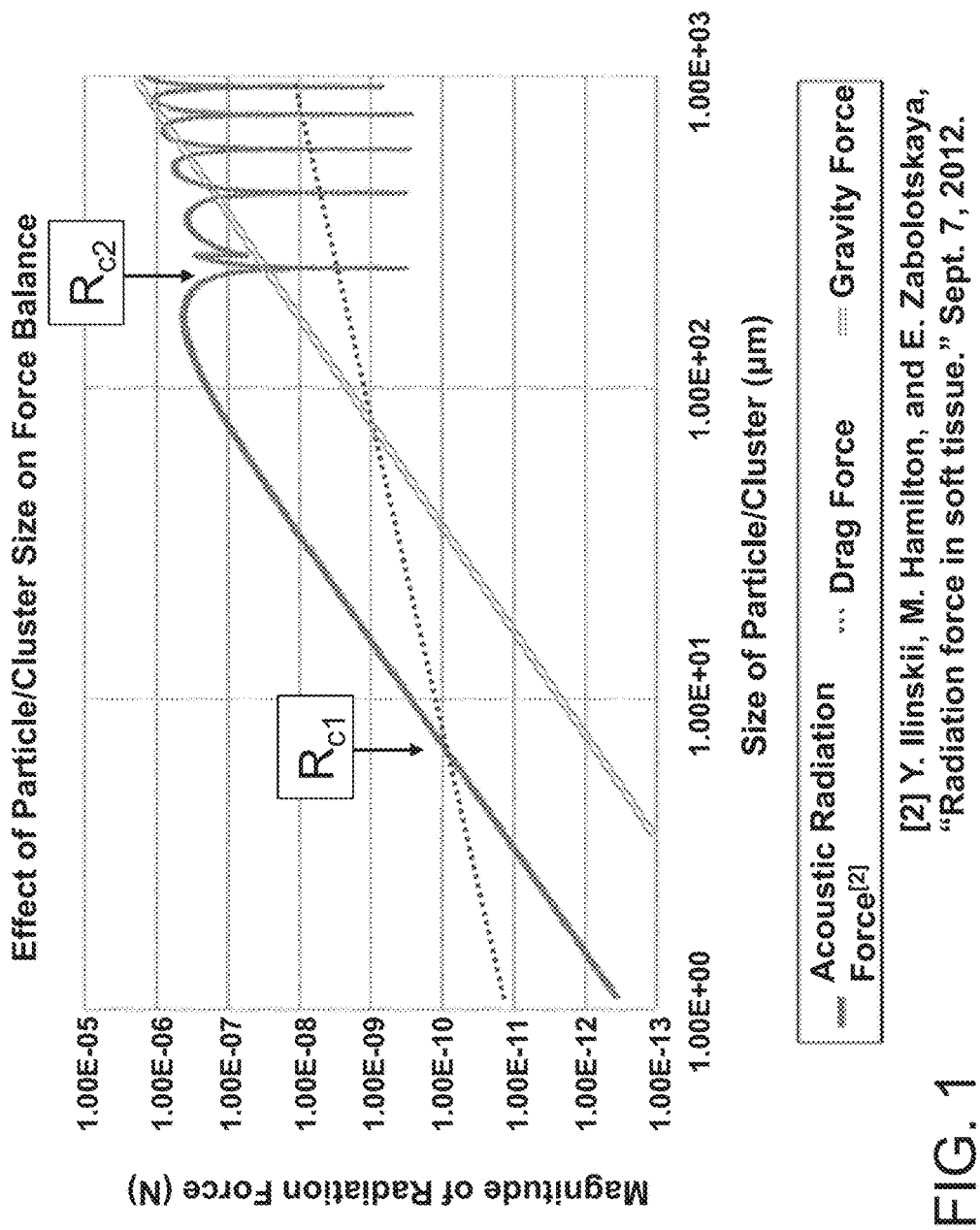
FIG. 1 is a graph showing the relationship of the acoustic radiation force, gravity/buoyancy force, and Stokes' drag force to particle size. The horizontal axis is in microns (μm) and the vertical axis is in Newtons (N).

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named component and allowing the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of "from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; upwards is always against the gravity of the earth.

The term "parallel" should be construed in its lay sense of two surfaces that maintain a generally constant distance between them, and not in the strict mathematical sense that such surfaces will never intersect when extended to infinity.

The present application refers to "the same order of magnitude." Two numbers are of the same order of magnitude if the quotient of the larger number divided by the smaller number is a value of at least 1 and less than 10.

Acoustophoresis is the separation of materials using acoustic waves. In the present disclosure, particles and secondary fluids are separated from a primary or host fluid using acoustic standing waves. The acoustic standing waves can exert forces in the host fluid and cause a change in position of the particles and/or secondary fluids when those exhibit a differential in density and/or compressibility. The differential in acoustic-related characteristics from the host fluid is sometimes referred to as the acoustic contrast factor. The pressure profile in an acoustic standing wave is also a standing wave and contains areas of local minimum pressure amplitudes at nodes and local maxima at anti-nodes. Particles and/or secondary fluids are driven by acoustic pressure forces to nodes or anti-nodes of the pressure standing wave in accordance with their density and/or compressibility. The higher the frequency of the standing wave, the smaller the particles that can be trapped at the nodes or anti-nodes.

The acoustophoretic separation technology of the present disclosure employs ultrasonic acoustic standing waves to trap, retain and/or collect particles and/or a secondary fluid from a host fluid. The particles or secondary fluid collect at the nodes or anti-nodes of the acoustic standing wave, depending on the particles' or secondary fluid's acoustic contrast factor relative to the host fluid. In the present disclosure, a multi-dimensional acoustic standing wave can be implemented that collects particles and/or secondary fluid into clusters. The clusters grow in size as more particles/secondary fluid is collected, until they eventually rise or fall out of the multi-dimensional acoustic standing wave. The clusters may rise or fall out when they have grown to a size large enough to overcome the holding force of the multi-dimensional acoustic standing wave. The scattering of the acoustic field off the particles results in a three-dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to stable axial positions within the standing waves. When the acoustic radiation force exerted on the particles is stronger than the combined effect of fluid drag force and buoyancy and gravitational force, the particle is trapped within the acoustic standing wave field. This continuous collecting of particles or secondary fluids in the acoustic standing wave field results in concentration, agglomeration and/or coalescence of the trapped particles/secondary fluid, which enhances their gravitational or buoyancy force. The multi-dimensional acoustic standing wave generates strong lateral forces that create rapid clustering of particles/secondary fluids. Relatively large solids of one material can thus be separated from smaller particles of a different material, the same material, and/or the host fluid through enhanced gravitational or enhanced buoyancy forces.

One specific application for the acoustophoresis device is in the processing of bioreactor materials. The bioreactor is used to culture cells that can express biological materials that are useful for various applications. The expressed materials are composed of biomolecules such as recombinant proteins or monoclonal antibodies, and are the desired product to be recovered. Through the use of acoustophoresis, the separation of the cells and cell debris from the desired product is very efficient and leads to very little loss of the expressed materials. This technique is an improvement over other filtration processes (depth filtration, tangential flow filtration, and the like), which show limited efficiencies at high cell densities. For example, in some instances the loss of the expressed materials in filter beds can be up to 5% of the materials produced by the bioreactor. The use of mammalian cell cultures including Chinese hamster ovary (CHO), NS0 hybridoma cells, baby hamster kidney (BHK) cells, and human cells has proven to be a very efficacious way of producing/expressing the recombinant proteins and monoclonal antibodies used in pharmaceuticals. The filtration of the mammalian cells and the mammalian cell debris through acoustophoresis aids in greatly increasing the yield of the bioreactor. The acoustophoresis process, through the use of multidimensional acoustic standing waves, may also be coupled with a standard filtration process upstream or downstream, such as depth filtration using diatomaceous earth, tangential flow filtration (TFF), or other physical filtration processes.

The present disclosure discusses applications related to particle separation from a host fluid. It should be understood that the techniques described herein are equally applicable to separating a secondary fluid from a host fluid, alone or in conjunction with separation of particles. Regarding acoustophoresis, the contrast factor is the difference between the compressibility and/or density of the particles and the fluid. These properties are characteristic of the particles and the fluid. Most cell types present a higher density and lower compressibility than the medium in which they are suspended, so that the acoustic contrast factor between the cells and the medium has a positive value. As a result, the axial acoustic radiation force (ARF) drives the cells, with a positive contrast factor, to the pressure nodal planes, whereas cells or other particles or fluids with a negative contrast factor are driven to the pressure anti-nodal planes. The radial or lateral component of the acoustic radiation force contributes to collecting the cells in the nodal planes or anti-nodal planes into clusters. The radial or lateral component of the ARF may be larger than the combined effect of fluid drag force and gravitational force to permit the cells to be collected into clusters.

As the cells agglomerate at the nodes of the standing wave, there is also a physical scrubbing of the cell culture media that occurs whereby more cells are trapped as they come in contact with the cells that are already held within the standing wave. This effect contributes to separating the cells from the cell culture media. The expressed biomolecules remain in the nutrient fluid stream (i.e. cell culture medium) and can be further process downstream, such as be being further purified or filtered.

Desirably, the ultrasonic transducer(s) generates a three-dimensional or multi-dimensional acoustic standing wave in the fluid that exerts a lateral force on the suspended particles to accompany the axial force so as to increase the particle trapping and clumping capabilities of the standing wave. This operation is different from traditional transducer operation in which a one-dimensional acoustic standing wave is produced with a lateral force that is two orders of magnitude smaller than the axial force. Rather, the transducer disclosed in this application is operated to obtain a lateral force that is greater in magnitude, up to the same order of magnitude as the axial force.

When acoustic standing waves propagate in liquids, the fast oscillations may generate a non-oscillating force on particles suspended in the liquid or on an interface between liquids. This force is known as the acoustic radiation force. The force originates from the non-linearity of the propagating wave. As a result of the non-linearity, the wave is distorted as it propagates and the time-averages are nonzero. By serial expansion (according to perturbation theory), the first non-zero term will be the second-order term, which accounts for the acoustic radiation force. The acoustic radiation force on a particle, or a cell, in a fluid suspension is a function of the difference in radiation pressure on either side of the particle or cell. The physical description of the radiation force is a superposition of the incident wave and a scattered wave, in addition to the effect of the non-rigid particle oscillating with a different speed compared to the surrounding medium thereby radiating a wave. The following equation presents an analytical expression for the acoustic radiation force on a particle, or cell, in a fluid suspension in a planar standing wave.

$$F_R = -\frac{3\pi P_0^2 V_P \beta_m}{2\lambda} \varphi(\beta, \rho) \sin(2kx) \tag{1}$$

where $\beta_m$ is the compressibility of the fluid medium, $\rho$ is density, $\varphi$ is acoustic contrast factor, $V_p$ is particle volume, $\lambda$ is wavelength, k is $2\pi/\lambda$, $P_0$ is acoustic pressure amplitude, x is the axial distance along the standing wave (i.e., perpendicular to the wave front), and $$\varphi(\beta, \rho) = \frac{5\rho_p - 2\rho_m}{2\rho_p + \rho_m} - \frac{\beta_p}{\beta_m}$$

where $\rho_p$ is the particle density, $\rho_m$ is the fluid medium density, $\beta_p$ is the compressibility of the particle, and $\beta_m$ is the compressibility of the fluid medium.

In a typical implementation, the acoustic transducer is operated to generate ultrasonic standing waves that propagate mainly in a direction referred to herein as axial. The acoustic transducer also produces acoustic pressure forces that act in a direction that is unaligned with the axial direction, referred to herein as lateral or radial forces. The axial component of the acoustic radiation force drives the particles, with a positive contrast factor, to the pressure nodal planes, whereas particles with a negative contrast factor are driven to the pressure anti-nodal planes. The radial or lateral component of the acoustic radiation force is the force that traps the particle. It therefore must be larger than the combined effect of fluid drag force and gravitational force. For small particles or emulsions, the drag force $F_D$ can be expressed as:

$$\vec{F}_D = 4\pi\mu_f R_P (\vec{U}_f - \vec{U}_p) \left[ \frac{1 + \frac{3}{2}\hat{\mu}}{1 + \hat{\mu}} \right] \tag{1}$$

where $U_f$ and $U_p$ are the fluid and particle velocity, $R_p$ is the particle radius, $\mu_f$ and $\mu_p$ are the dynamic viscosity of the fluid and particle, and $\hat{\mu} = \mu_p/\mu_f$ is the ratio of dynamic viscosities. The buoyancy force $F_B$ is expressed as:

$$F_B = 4/3\pi R_P^3 (\rho_f - \rho_p) g \tag{2}$$

where $R_p$ is the particle radius, $\rho_f$ is the fluid density, $\rho_p$ is the particle density, and g is the universal gravitational constant.

For a particle to be trapped in the ultrasonic standing wave, the force balance on the particle must be zero, and therefore an expression for lateral acoustic radiation force $F_{LRF}$ can be found, which is given by:

$$F_{LRF} = F_D + F_B \tag{3}$$

For a particle of known size and material property, and for a given flow rate, this equation can be used to estimate the magnitude of the lateral acoustic radiation force.

The theoretical model that is used to calculate the acoustic radiation force is the formulation developed by Gor'kov, where the primary acoustic radiation force $F_R$ is defined as a function of a field potential U, $F_R = -\nabla(U)$, where the field potential U is defined as $$U = V_O \left[ \frac{\langle p^2(x, y, z) \rangle}{2\rho_f c_f^2} f_1 - \frac{3\rho_f \langle v^2(x, y, z) \rangle}{4} f_2 \right]$$

and $f_1$ and $f_2$ are the monopole and dipole contributions defined by $$f_1 = 1 - \frac{1}{\Lambda \sigma^2} \qquad f_2 = \frac{2(\Lambda - 1)}{2\Lambda + 1}$$

where $$\sigma = \frac{c_p}{c_f} \qquad \Lambda = \frac{\rho_p}{\rho_f} \qquad \beta_f = \frac{1}{\rho_f c_f^2}$$

where p is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o = \pi R_p^3$ is the volume of the cell, and < > indicates time averaging over the period of the wave.

For a one dimensional standing wave, where the acoustic pressure is expressed as $$p = A \cos(kx)\cos(\omega t) \tag{4}$$

where A is the acoustic pressure amplitude, k is the wavenumber, and $\omega$ is the angular frequency. In this case, there is only the axial component of the acoustic radiation force $F_{ARF}$, which is found to be $$F_{ARF} = V_O k X \frac{A^2}{4\rho_f c_f^2} \sin(2kx) \tag{5}$$

where X is the contrast factor given by $$X = \left( \frac{5\Lambda - 2}{1 + 2\Lambda} - \frac{1}{\sigma^2 \Lambda} \right)$$

Particles with a positive contrast factor will be driven to the pressure nodal planes, and particles with a negative contrast factor will be driven to the pressure anti-nodal planes. In this way, the generation of a multi-dimensional acoustic standing wave in an acoustic chamber results in the creation of tightly packed clusters of particles in the acoustic chamber, typically corresponding to the location of the pressure nodes or anti-nodes in the standing wave depending on acoustic contrast factor.

Gork'ov's model is for a single particle in a standing wave and may be limited to particle sizes that are small with respect to the wavelength of the sound fields in the fluid. The model does not take into account the effect of viscosity of the fluid and the particle on the radiation force. As a result, this model may not be useful for macro-scale ultrasonic separators since particle clusters can grow relatively quite large compared to micro-scale particles.

For larger particle sizes, Ilinskii provides equations for calculating the 3D acoustic radiation forces for any particle size. See Ilinskii, *Acoustic Radiation Force on a Sphere in Tissue*, The Journal of the Acoustical Society of America, 132, 3, 1954 (2012), which is incorporated herein by reference.

FIG. 1 is a log-log graph (logarithmic y-axis, logarithmic x-axis) that shows the scaling of the acoustic radiation force, fluid drag force, and buoyancy force with particle radius. Calculations are done for a typical mammalian cell used in experiments. In the experiment, the mammalian cell had a density ($\rho_p$) of 1,050 kg/m$^3$ and a cell sound speed ($c_p$) of 1,550 m/s. The fluid in which the particle was flowed was water having a density ($\rho_w$) of 1000 kg/m$^3$, a fluid sound speed ($c_f$) of 1500 m/s, and a flow rate ($v_f$) of 4 cm/min. The experiment used 33 PZT-8 ultrasonic transducers driven at a frequency (f) of 2.2 MHz at a pressure (p) of 1 MPa. As explained above, the gravity/buoyancy force is a particle volume dependent force, and is therefore negligible for particle sizes on the order of micron, but grows, and becomes significant for particle sizes on the order of hundreds of microns. The fluid drag force scales linearly with fluid velocity, and therefore typically exceeds the buoyancy force for micron sized particles, but is negligible for larger sized particles on the order of hundreds of microns. The acoustic radiation force scaling is different. When the particle size is small, Gor'kov's equation is accurate and the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when a suspension is flowing through the system with primarily small micron sized particles, it is necessary for the acoustic radiation force to balance the combined effect of fluid drag force and buoyancy force for a particle to be trapped in the standing wave. In FIG. 1, this happens for a particle size of about 3.5 micron, labeled as $R_{c1}$. The graph then indicates that all larger particles will be trapped as well. Therefore, when small particles are trapped in the standing wave, particles coalescence/clumping/aggregation/agglomeration takes place, resulting in continuous growth of effective particle size. As the particle size grows, the acoustic radiation force reflects off the particle, such that large particles will cause the acoustic radiation force to decrease. Particle size growth continues until the buoyancy force becomes dominant, which is indicated by a second critical particle size, $R_{c2}$, at which size the particles will rise or sink, depending on their relative density with respect to the host fluid. Thus, FIG. 1 explains how small particles can be trapped continuously in a standing wave, grow into larger particles or clumps, and then continuously will rise or settle out because of enhanced buoyancy or gravity forces.

The models that were implemented in the present disclosure are based on the theoretical work of Yurii Ilinskii and Evgenia Zabolotskaya as described in AIP Conference Proceedings, Vol. 1474-1, pp. 255-258 (2012). These models also include the effect of fluid and particle viscosity, and therefore are a more accurate calculation of the acoustic radiation force.

The acoustophoretic separation technology of the present disclosure employs multi-dimensional ultrasonic acoustic standing waves, planar acoustic standing waves or combinations of planar and multidimensional acoustic standing waves (collectively referred to herein simple as acoustic standing waves) to trap particles or a secondary fluid in a volume of fluid containing said particles/secondary fluid.

Figures 2A, 2B:
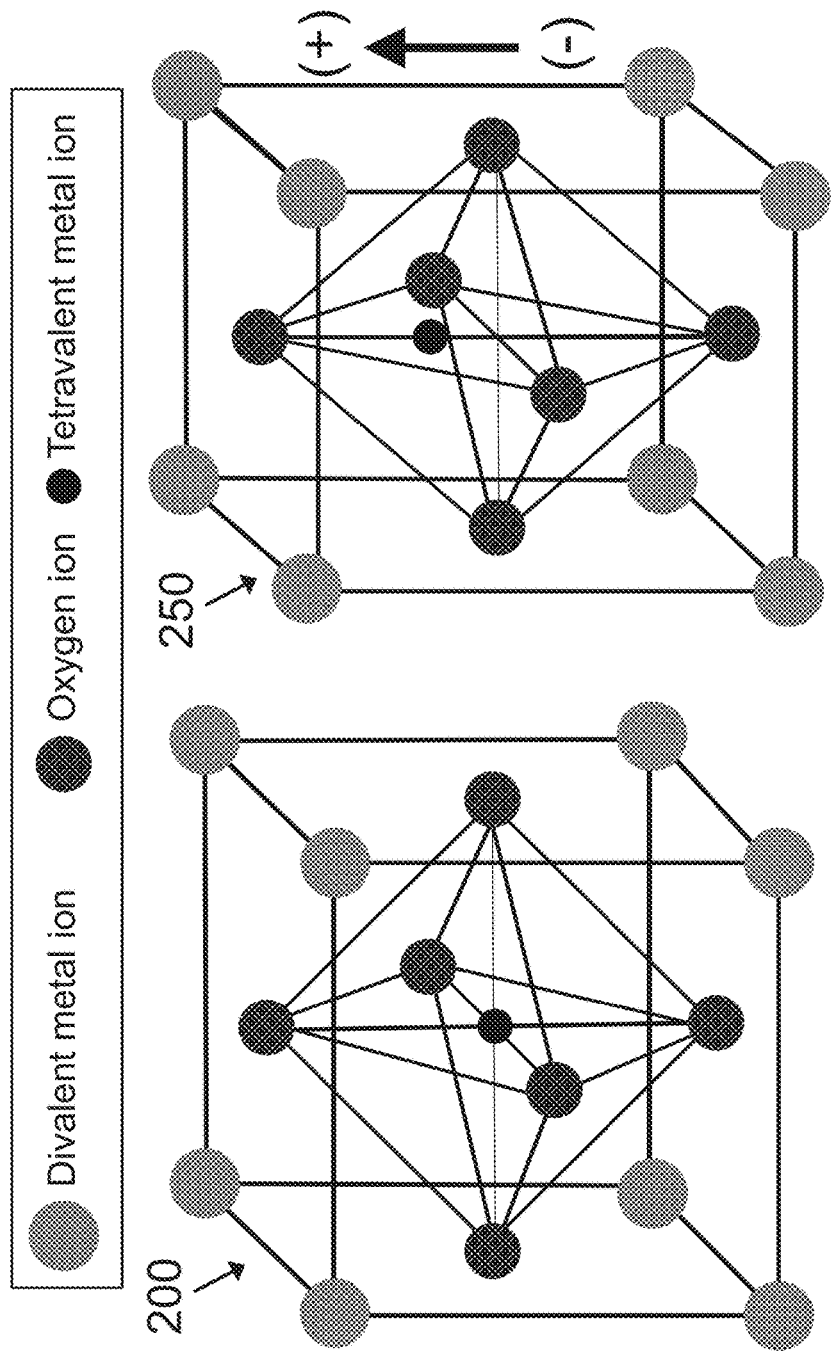
FIG. 2A illustrates a first embodiment of a piezoelectric material according to the present disclosure. The piezoelectric material is a perovskite crystal at a temperature above the Curie point.
FIG. 2B illustrates a second embodiment of a piezoelectric material according to the present disclosure. The piezoelectric material is a perovskite crystal at a temperature below the Curie point.

Turning now to FIG. 2A, a first embodiment of a piezoelectric material 200 is shown. In the embodiment depicted in FIG. 2A, the piezoelectric material 200 is a perovskite crystal at a temperature above the Curie point. The piezoelectric material 200 is in the shape of a cubic lattice with a symmetrical arrangement of positive and negative charges. FIG. 2B shows a second embodiment of a piezoelectric material 250. In the embodiment depicted in FIG. 2B, the piezoelectric material 250 is a perovskite crystal at a temperature below the Curie point. The piezoelectric material 250 is in the shape of a tetragonal (orthorhombic) lattice with an electric dipole. Both of the piezoelectric materials 200, 250 depicted in FIG. 2A and FIG. 2B are comprised of divalent metal ion(s) (e.g., lead, barium), oxygen ion(s), and tetravalent metal ion(s) (e.g., titanium, zirconium). The dipole expansion and contraction of the piezoelectric materials 200, 250 depicted in FIG. 2A and FIG. 2B allow for the piezoelectric effect to occur, resulting in the generation of pressure waves.

The Curie point is a critical temperature at which each perovskite crystal in a piezoelectric material exhibits a simple cubic symmetry with no dipole moment. However, at temperatures below the Curie point, such as is depicted in FIG. 2B, each crystal has tetragonal or rhombohedral symmetry and a dipole moment. Adjoining dipoles form regions of local alignment are called domains. The alignment of the crystals gives a net dipole moment to the domain in the crystal and, as a result, generates a net polarization. The polarization, however, is still random and thus there is no overall direction that the piezoelectric crystal will change in shape when an electrical impulse is applied.

In operation, a strong, direct current electric field, usually at a temperature slightly below the Curie point, is applied to the crystal. Through this poling (polarization) treatment, the domains of the piezoelectric crystal most nearly aligned with the electric field expand at the expense of domains that are not aligned with the field, and the piezoelectric crystal expands in the direction of the strong electrical field. When the electric field is removed, most of the dipoles are locked into a configuration of near alignment. The piezoelectric crystal now has a permanent polarization (i.e., the crystal can be considered "poled"). Thus, upon supplying an electrical charge to the crystal, the crystal will expand and contract in the direction that it is now poled.

In a conventional flat/planar piezoelectric surface, a single frequency can be used to excite a multi-dimensional acoustic standing wave. In accordance with the present disclosure, it has been found that a piezoelectric material having a non-planar (i.e., non-flat) face can be electrically excited by a single frequency to further enhance the expansion and contraction in the poled direction of the crystal, such that differential vibrations (as opposed to uniform vibrations) emanate from the surface of the non-planar face of the piezoelectric material to generate a multi-dimensional acoustic standing wave. Through proper shaping of the non-planar surface, a multi-dimensional acoustic standing wave can be generated as desired (e.g., with a desired strength, shape, intensity).

FIG. 3 shows a first embodiment of such a piezoelectric material 300 in which a non-planar first face 310 of the piezoelectric material 300 is defined by a smooth function. In this way, the non-planar face 310 of the piezoelectric material 300 is poled in a direction 320 substantially perpendicular to a second face 330 of the piezoelectric material 300. In the piezoelectric material 300 depicted in FIG. 3, the non-planar face 310 and the second face 330 are located on opposite sides of the crystal. The second face is planar, and provides the reference against which the non-planarity of the first face 310 is determined. As seen here, the first face 310 is formed from a series of peaks 312 and valleys 314. The transition between the peaks and valleys is smooth. A smooth function is a function having a derivative that is continuous.

A single electrode can be used on each side of the piezoelectric material. The electrode may be coated by several means, such as plating with electroless nickel or spray coating with a conductive coating, such as a silver-containing coating. The electrodes must be separated so that there is a positive terminal and a negative terminal to energize the piezoelectric material.

Figure 4:
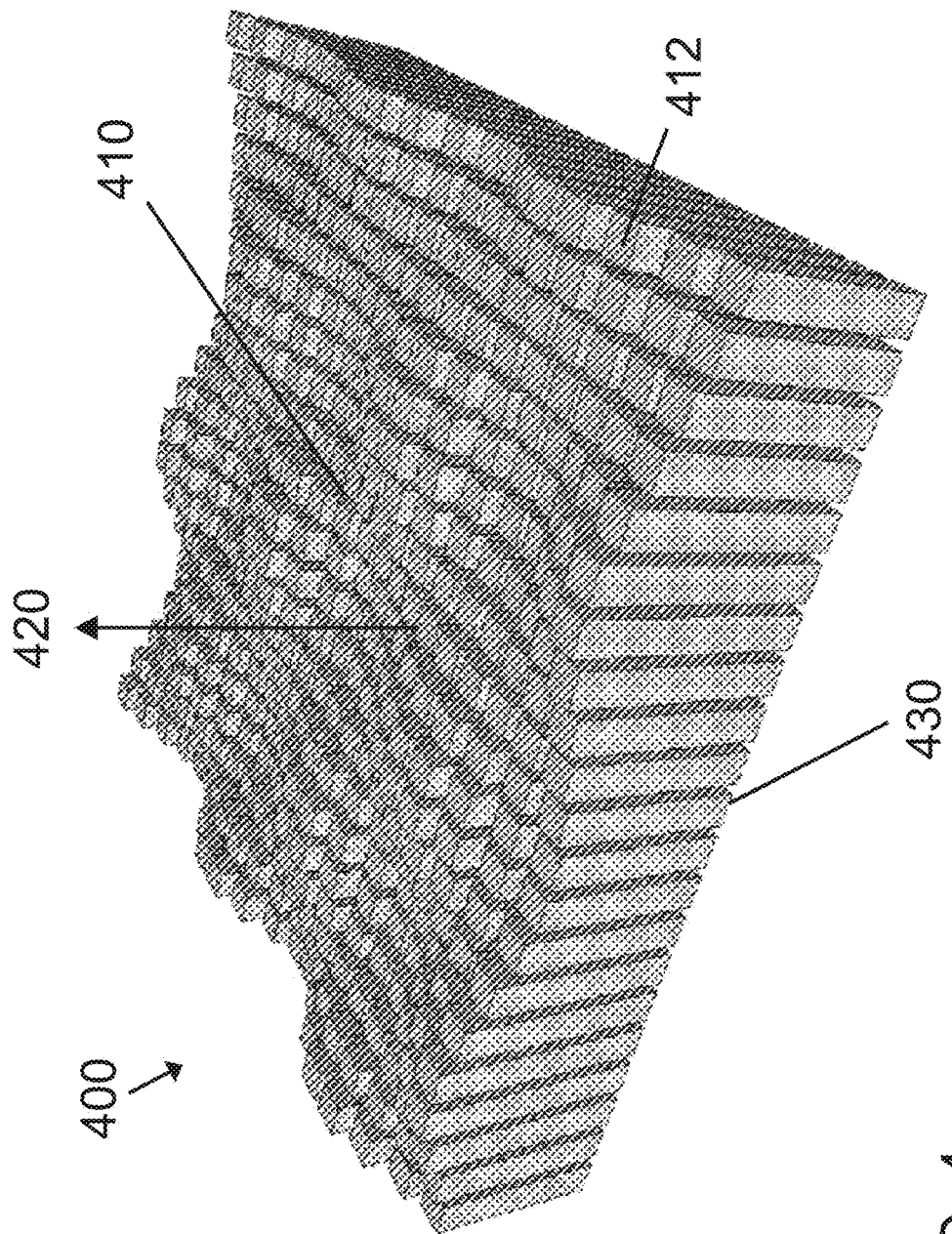
FIG. 4 illustrates a second embodiment of a non-planar face of a piezoelectric material according to the present disclosure. The non-planar face of the piezoelectric material is defined by a stepped function formed by facets.

In contrast to FIG. 3, FIG. 4 shows a second embodiment of a piezoelectric material 400 in which a non-planar first face 410 of the piezoelectric material 400 is defined by a stepped function. Again, the non-planar face 410 of the piezoelectric material 400 is poled in a direction 420 substantially perpendicular to a second face 430 of the piezoelectric material 400. A stepped function is a piecewise constant function. As seen here, the overall shape of the first face 410 is made up of a series of smaller flat surfaces 412, also referred to herein as facets.

Figure 5:
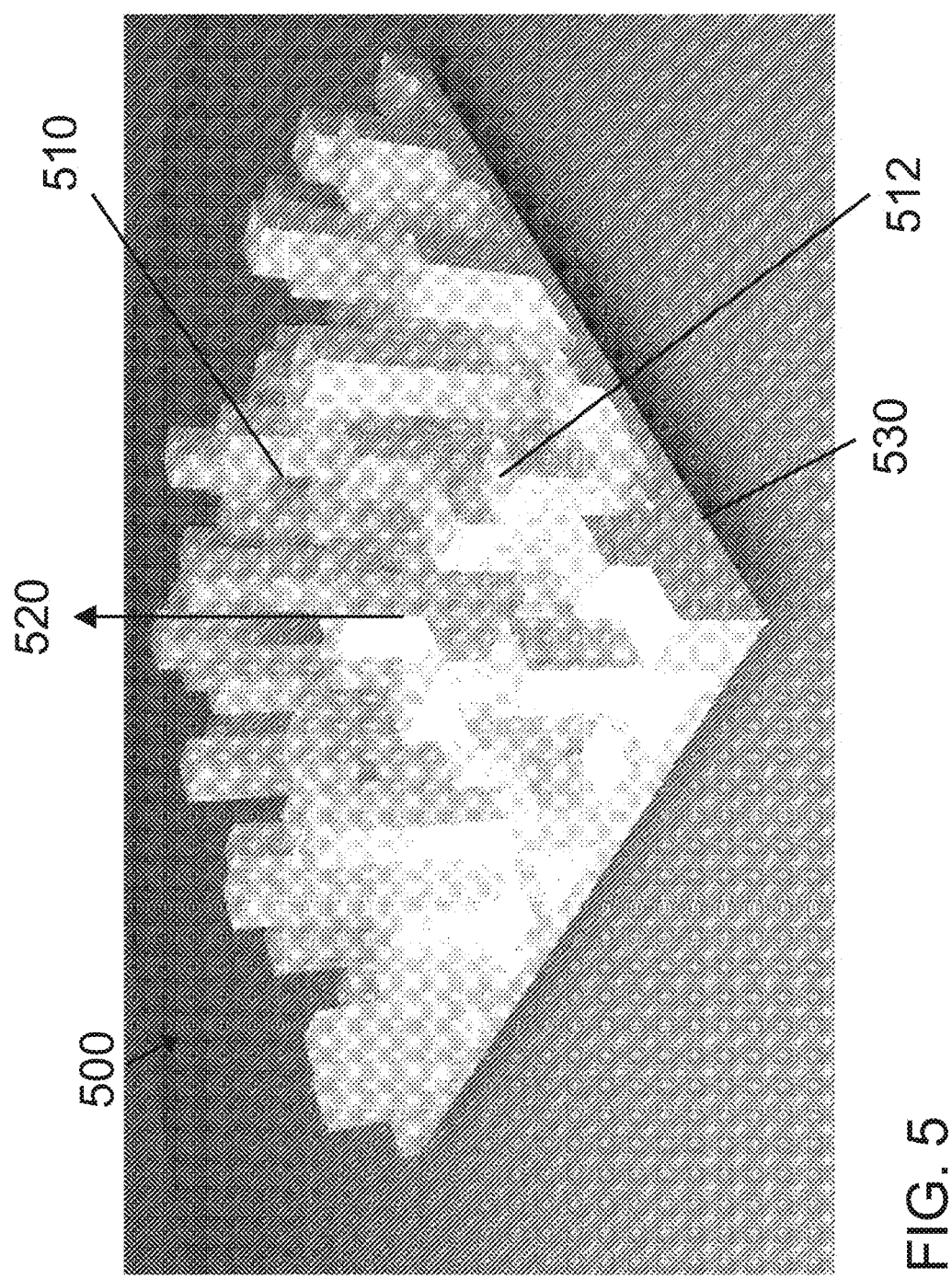
FIG. 5 illustrates a third embodiment of a non-planar face of a piezoelectric material according to the present disclosure. The non-planar face of the piezoelectric material is defined by a stepped function formed by facets.

FIG. 5 shows a third embodiment of a piezoelectric material 500 in which a non-planar face 510 of the piezoelectric material 500 is defined by a stepped function. The non-planar first face 510 of the piezoelectric material 500 is poled in a direction 520 substantially perpendicular to a second face 530 of the piezoelectric material 500. FIG. 4 and FIG. 5 differ in at least that the adjacent smaller flat surfaces or facets 512 vary much more in their difference in height (relative to the second face 530). In some embodiments, including that illustrated in FIG. 5, each of the facets or outward facing surfaces of the piezoelectric material may or may not be connected to an electrode. A number of the facets may be connected to each other electrically, and to a first electrode, to be excited at a first frequency. Other facets or groups of facets can be connected electrically to each other and to another electrode, to be excited at a second frequency, at the same or different or overlapping times as the first electrode is excited at the first frequency. Each individual facet may be connected to a single distinct electrode, to permit excitation at discrete frequencies, some or all of which may be the same or different. Accordingly, any combination of electrode-facet connections is possible, as is excitation at any combination of distinct frequencies.

Figure 6:
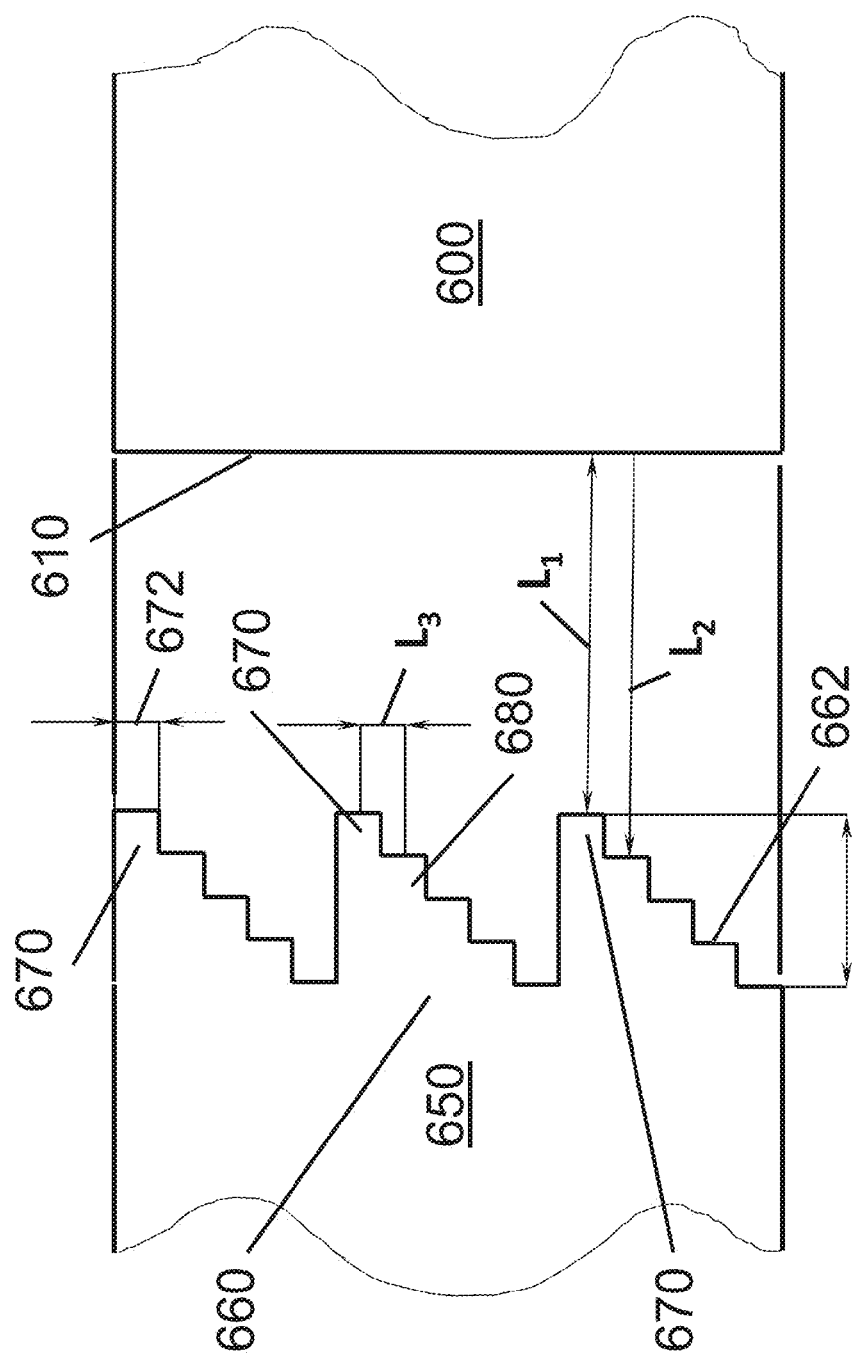
FIG. 6 illustrates a cross-sectional view of an acoustic chamber of an acoustophoretic device according to the present disclosure. The device includes a piezoelectric material having a planar first face and a reflector having a faceted surface. The acoustic chamber may be closed, or may house a flowing fluid.

The reflector located opposite the transducer/piezoelectric material can also have a non-planar surface, which can be likewise defined by a smooth or stepped function. The non-planar face of the transducer/piezoelectric material and the non-planar surface of the reflector may be described as being faceted, such as is depicted in FIG. 6. In FIG. 6, the piezoelectric material 600 has a flat, planar first face 610, and the reflector 650 has a faceted surface 660. The faceted surface 660 of the reflector 650 is defined by flat surfaces or facets 662, similar to the facets 512 of the piezoelectric material 500 of FIG. 5 and the facets 412 of the piezoelectric material 400 of FIG. 4. That is, as depicted in FIG. 6, the facets 662 in the faceted surface 660 of the reflector 650 can be stepped, such that adjacent facets are located different distances from a first face 610 of the piezoelectric material 600. For example, facet 670 is located distance $L_1$ from the first face 610 of the piezoelectric material 600, while facet 680 is located distance $L_2$ from the first face 610 of the piezoelectric material 600, with $L_1$ being greater than $L_2$. It is to be understood that the facets 662 may be dimensioned as desired. For example, facet 670 typically has a width 672 selected to maximize the reflected energy. Similarly, the distance between adjacent facets, such as distance $L_3$ between facet 670 and facet 680, is typically selected to minimize the distance between the director of a natural vibration mode of the piezoelectric material and adjacent facets. The distance between a facet and the first face 610 of the piezoelectric material 600 (e.g., distance $L_1$ for facet 670 and distance $L_2$ for facet 680) may correspond to an integer multiple of a half-wavelength to accommodate possible resonance conditions in the acoustic chamber.

Figure 7A:
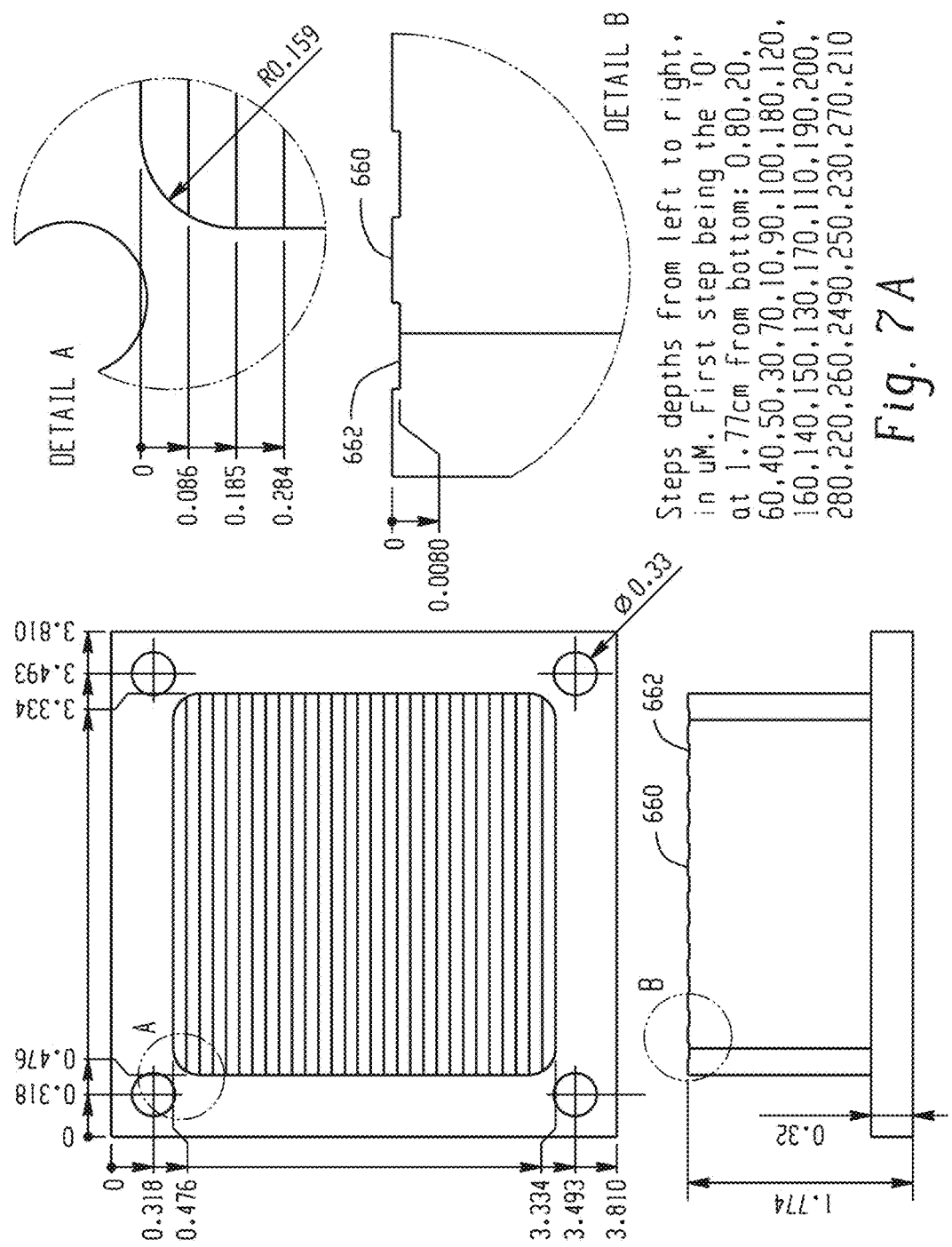
FIG. 7A illustrates a first exemplary configuration of the faceted surface of the reflector of FIG. 6.
Figure 7B:
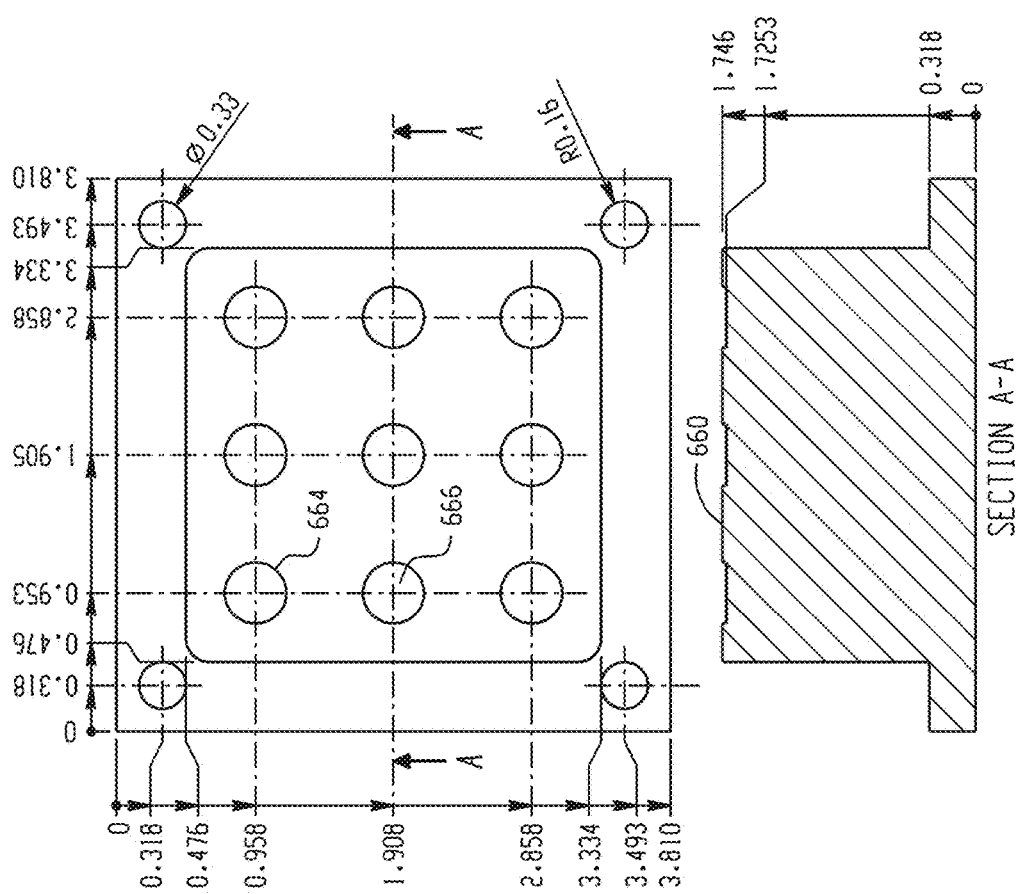
FIG. 7B illustrates a second exemplary configuration of the faceted surface of the reflector of FIG. 6.

Facets 662 can be arranged as desired to create an acoustic standing wave having a desired mode pattern. FIGS. 7A-7C depict various exemplary configurations of the faceted surface 660 of the reflector 650. For example, FIG. 7A shows a design in which the faceted surface 660 of the reflector 650 includes flat surfaces or facets 662 that extend along the length of the reflector 650. The height of a given facet generally differs from the height of an adjacent facet by a fraction of the generated acoustic standing wave. The design in FIG. 7A implements a degenerated one-dimensional pattern of intermittent steps.

FIG. 7B shows a design in which the faceted surface 660 of the reflector 650 includes wells 664 having flat bottoms 666. In the exemplary embodiment of FIG. 7B, the wells 664 are all of equal depth. The distribution of the wells 664 on the faceted surface 660 of the reflector 650 corresponds to the distribution of the 3×3 mode pattern emitted by the reflector 650. The wells are distributed in a regular pattern along the faceted surface.

Figure 8:
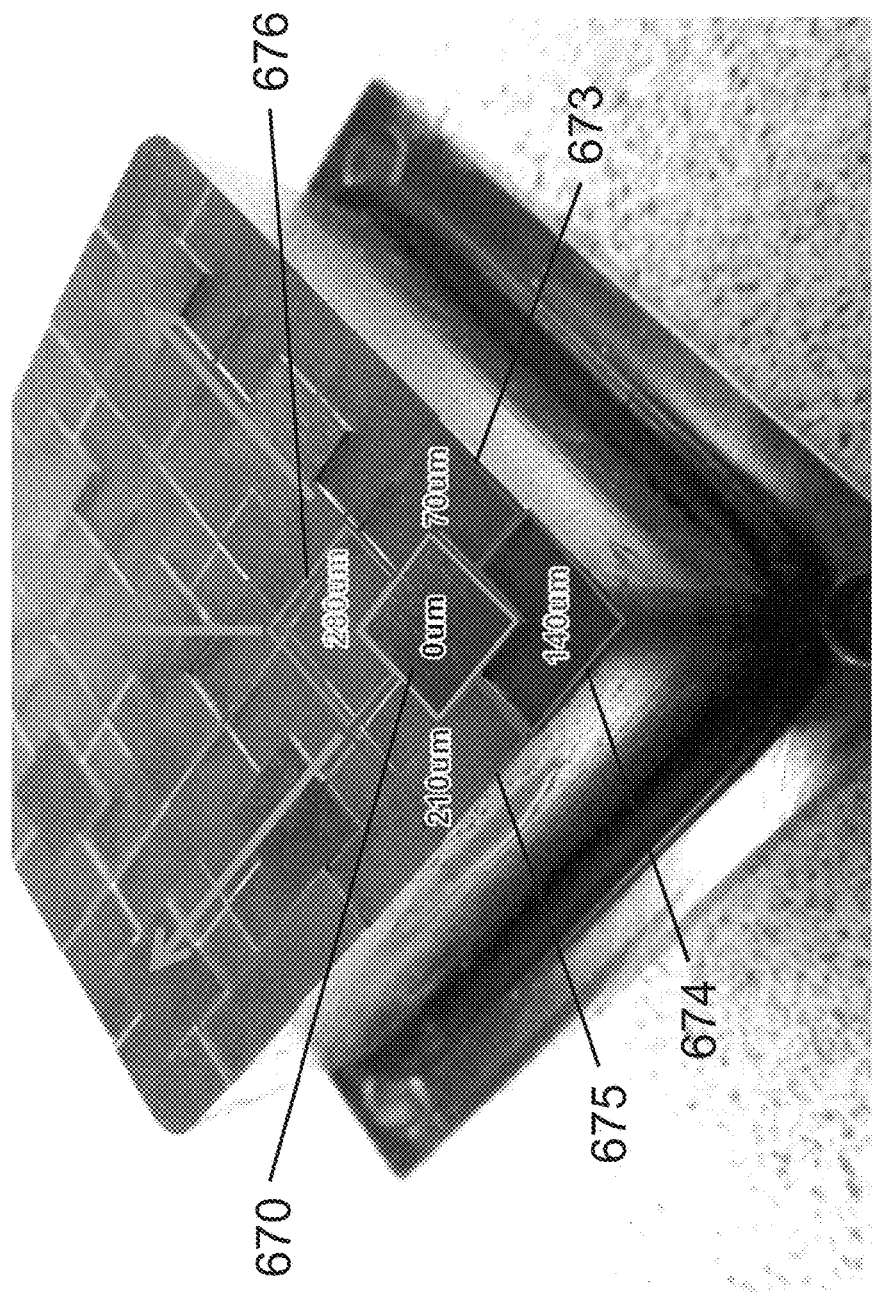
FIG. 8 illustrates a magnified view of a facet cluster of the faceted surface of FIG. 7C, showing the height differential between a central facet and four surrounding outer facets.

FIG. 7C and FIG. 8 show a design in which the faceted surface 660 of the reflector 650 includes multiple facet clusters 668. In this example embodiment, each facet cluster 668 is comprised of a pyramid-shaped group of five facets, with four outer facets 673, 674, 675, 676 differing from a central facet 670 by a multiple of 0.1 wavelengths. That is, if the central facet 670 corresponds to the 0 position, the four outer facets 673, 674, 675, 676 are deeper by 0.1, 0.2, 0.3, and 0.4 wavelengths, respectively. For example, central facet 670 in FIG. 8 corresponds to position 0, outer facet 673 is located 70 µm below the surface of the central facet 670, outer facet 674 is located 140 µm below the surface of the central facet 670, outer facet 675 is located 210 µm below the surface of the central facet 670, and outer facet 676 is located 240 µm below the surface of the central facet 670. The distribution of the facet clusters 668 corresponds to the distribution of the 9×9 mode pattern reflected by the reflector, though it is to be understood that such a design could also be used with a 3×3 mode pattern. It is further contemplated that the pattern of the facets in the faceted surface 660 of the reflector 650 may influence the mode selection for various frequencies. The number of facets or facet levels within a single facet cluster is typically selected to ensure smooth adjustment to the changing resonance conditions within the acoustic chamber (i.e., more facets or facet levels for more gradual transitions), with the facets or facet levels differing from one another by a fraction of the acoustic wavelength, as explained elsewhere herein. The number of facets or facet levels may be limited to reduce or minimize the total number of facets. In some examples, the fewer number of facets, the greater the reflecting area per facet. As will be appreciated by those skilled in the art, the piezoelectric material may likewise have a faceted front face, similar to the faceted surface of the reflector depicted in FIG. 6 and FIGS. 7A-7C. In such embodiments, the first face of the piezoelectric material is faceted, while the surface of the reflector is generally kept planar or flat.

Figure 9:
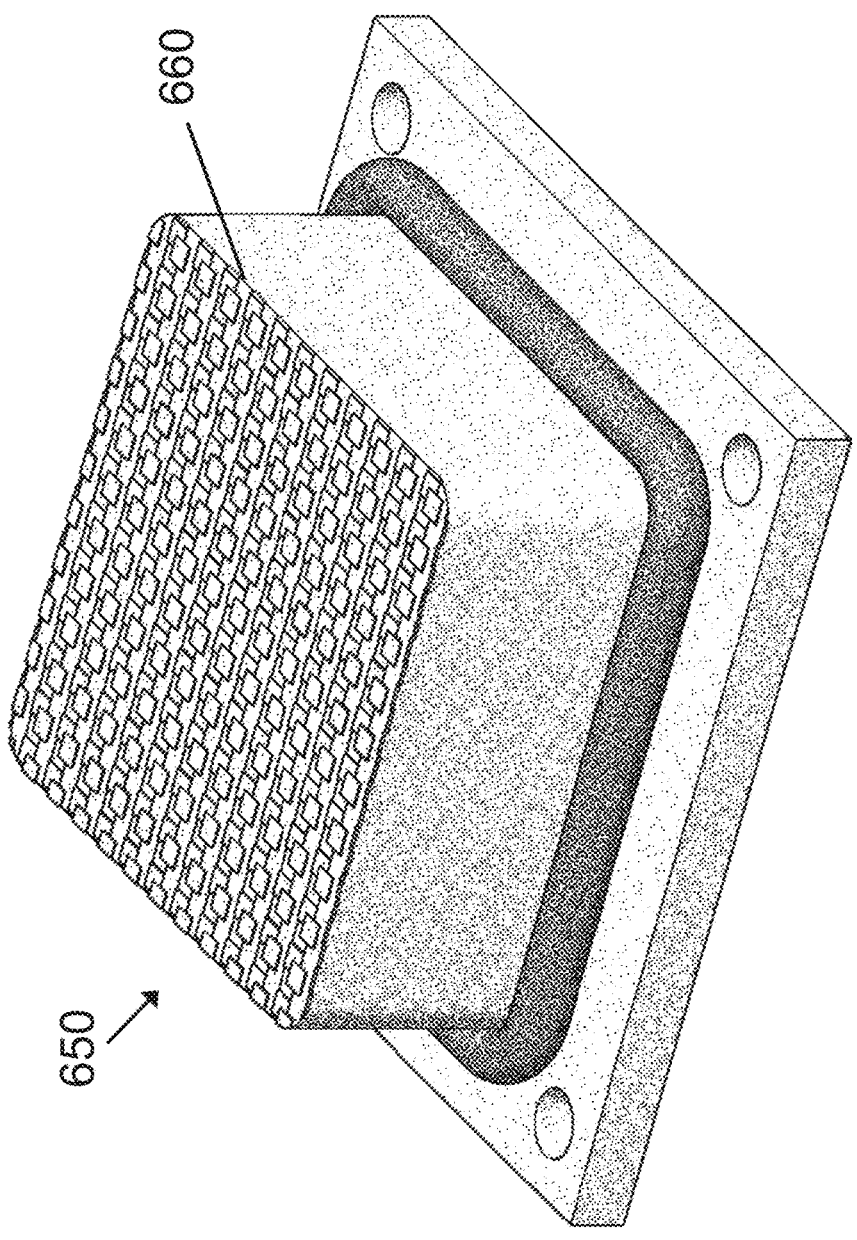
FIG. 9 illustrates a fourth exemplary configuration of the faceted surface of the reflector of FIG. 6.
Figure 10:
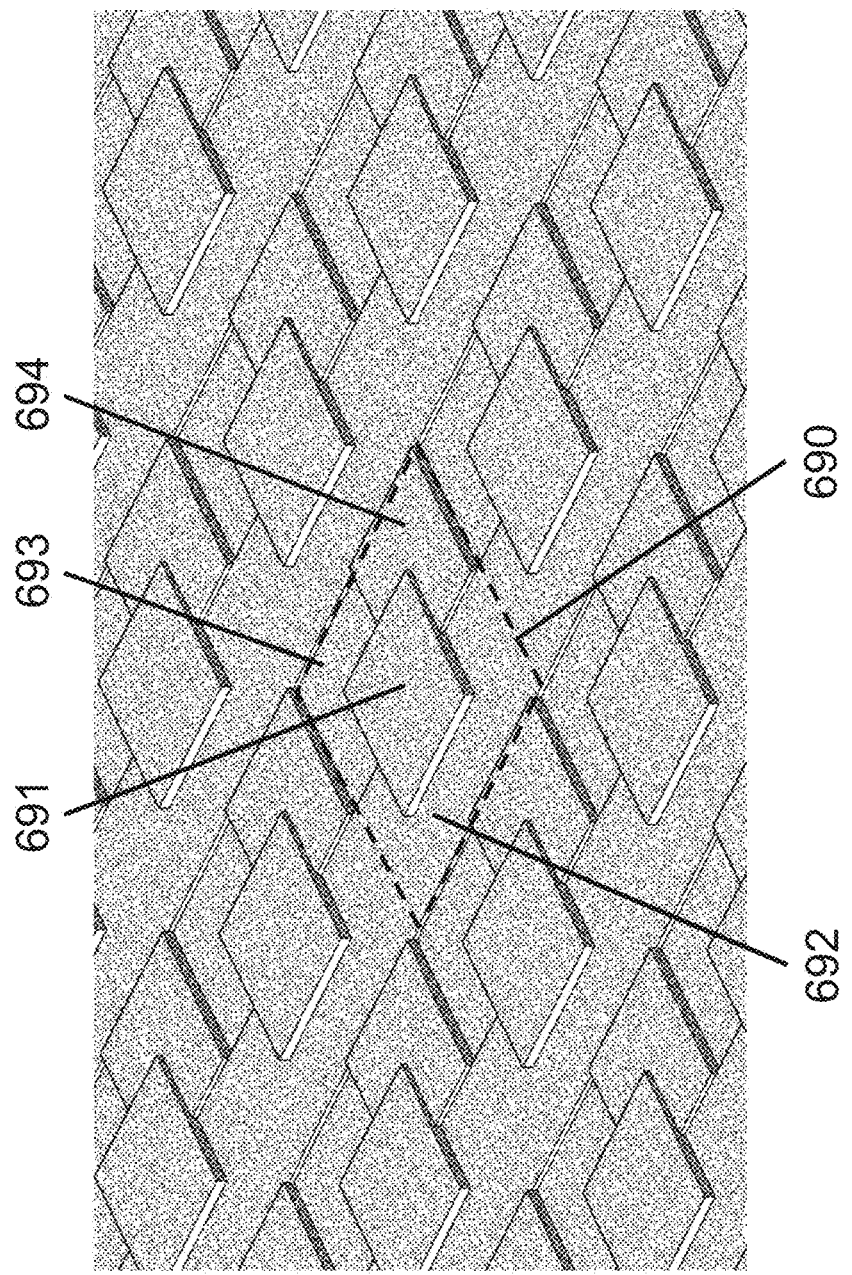
FIG. 10 illustrates a magnified view of the faceted surfaces depicted in FIG. 9.

FIG. 9 and FIG. 10 depict another exemplary embodiment of a faceted surface 660 of the reflector 650. FIG. 9 shows the entire reflector, while FIG. 10 provides a magnified view of a portion of the faceted surface 660 of the reflector 650. As best seen in FIG. 10, the surface is divided into multiple facets that provide four different heights. A dotted line is used to indicate the facet cluster 690. The central facet 691 is surrounded by a second facet 692, a third facet 693, and a fourth facet 694. The second facet 692 has approximately twice the surface area of the third facet or the fourth facet. The third facet 693 is the lowest of these facets, followed by the second facet 692, then the fourth facet 694, with the central facet 691 being the highest of these facets.

It is noted that in FIGS. 4-10, the facets are generally illustrated as being surfaces with a square-shaped perimeter. This is not a requirement, and the facets may be of any suitable shape, e.g. rectangular, circular, etc.

As will be explained in greater detail herein, the operation of the acoustophoretic devices of the present disclosure includes generation of acoustic standing waves in an acoustic chamber. The acoustic standing waves can be at a fixed or varying frequency throughout the period of operation, and the frequency or a range of frequencies may be selected to match the mode distribution of the piezoelectric material to the facet distribution of the reflector. An increased or maximal amplitude of the acoustic standing wave may be achieved under resonance conditions that occur when the wave frequency f satisfies the condition $f = nc/2L$, where c is the speed of sound in the medium, n is a positive integer, and L is the distance between the transducer and the reflector. Increased or potentially optimal cell separation may be achieved under conditions that may include resonance conditions near or at a maximal amplitude of the acoustic pressure for a fixed emitter power. The maximal acoustic pressure may provide maximal acoustic radiation force, which is the result of the acoustic field gradients, and may provide efficient cell trapping. When particles (e.g., cells) accumulate within the acoustophoretic device (or more generally due to inhomogeneous conditions), the speed of sound c changes and the resonance conditions may deteriorate. The speed of sound may also change due to the change of temperature of the suspension. The temperature change may be a result of the acoustic operation or due to the change of the feed solution temperature, as examples. The resonance conditions may be different for different suspension compositions.

Figure 11:
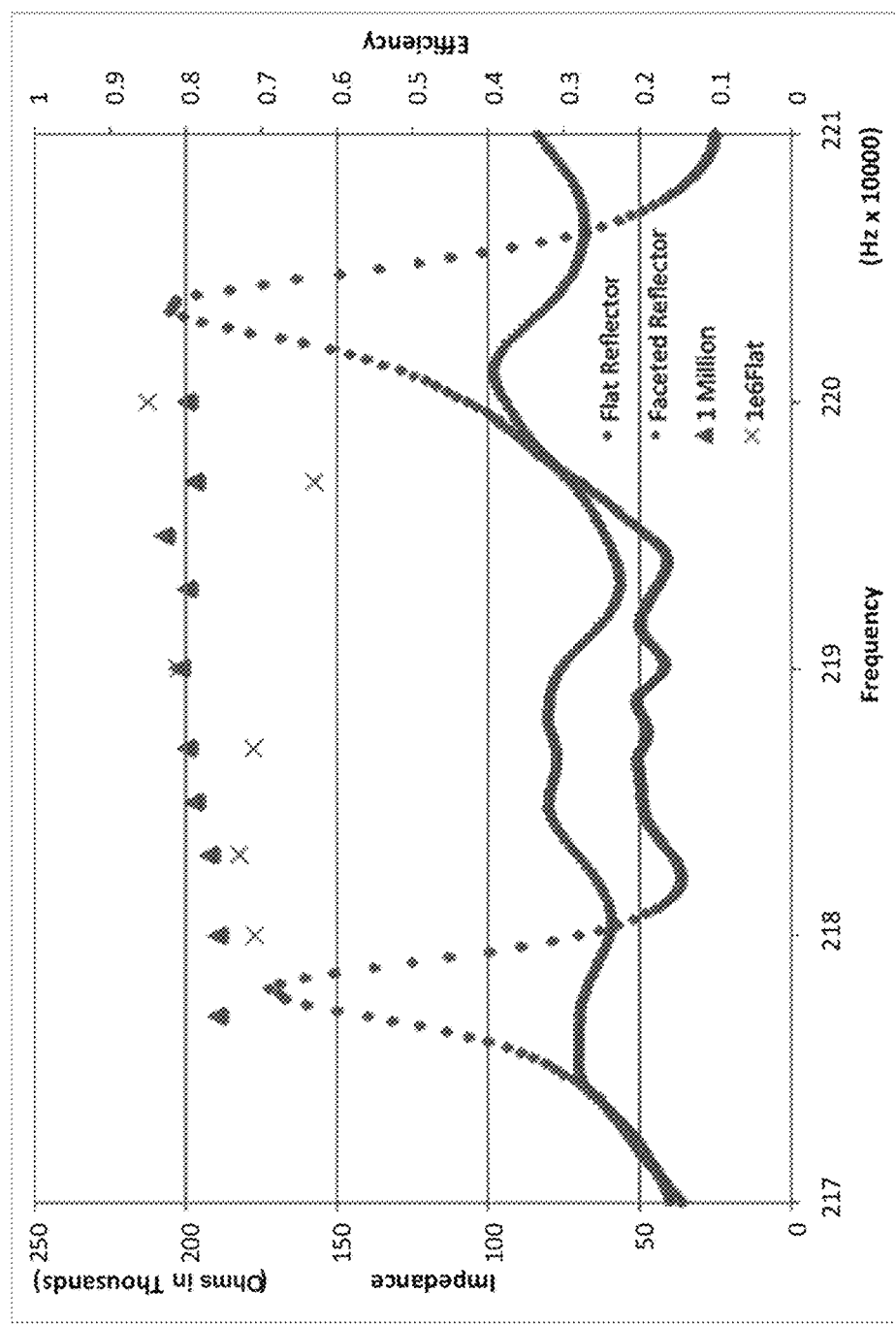
FIG. 11 is a graph illustrating the separation efficiency of a faceted reflector versus a flat, planar reflector at varied impedance levels. The left-hand y-axis is impedance in thousands of ohms. The two lines marked as "Flat Reflector" and "Faceted Reflector" are read against the left-hand y-axis. The right-hand y-axis is efficiency. The points labeled "1 million" and "1e6 flat" (triangular and X-shaped points) are read against the right-hand y-axis. The x-axis is in units of ten thousand Hertz.
Figure 12:
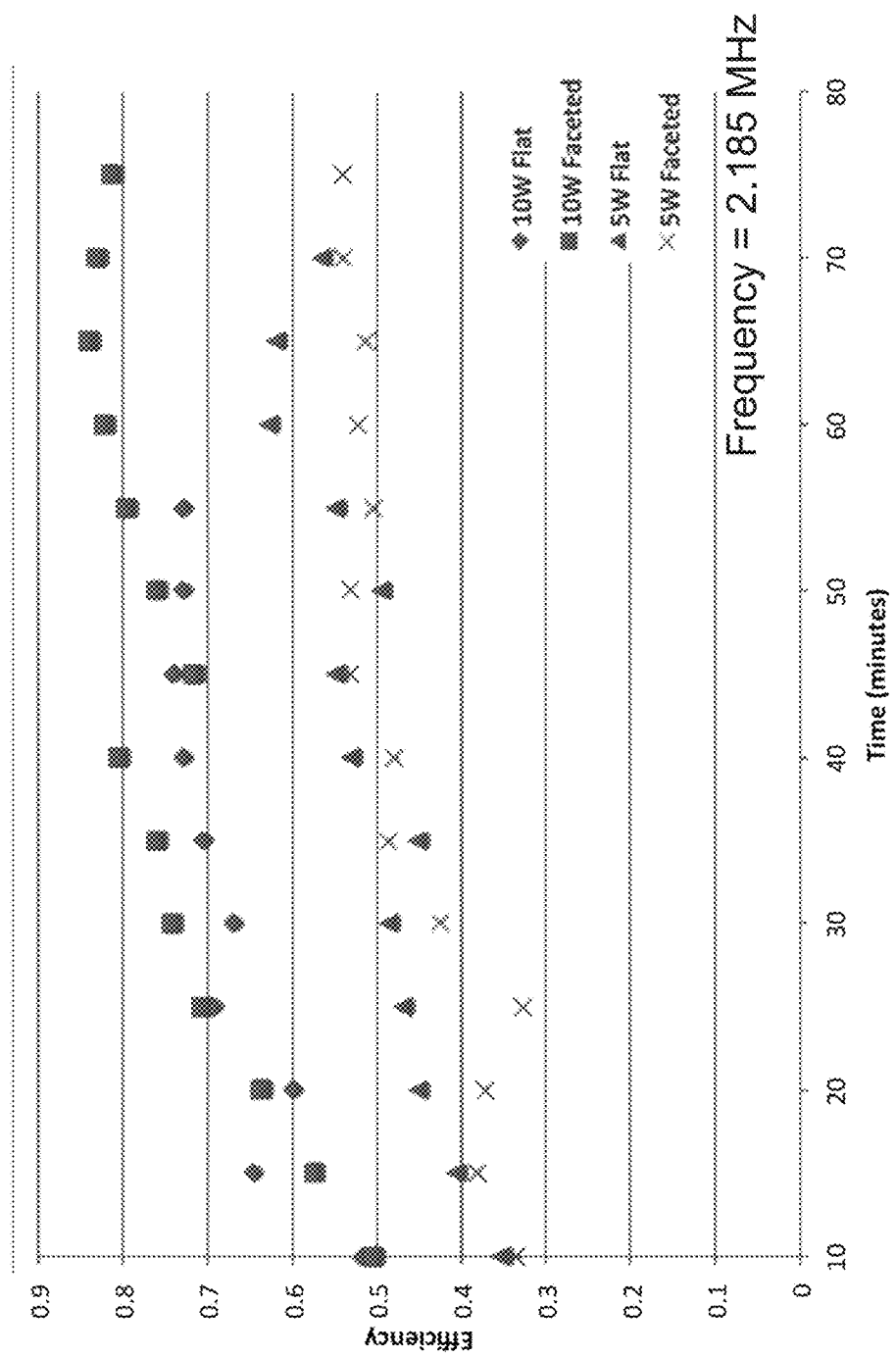
FIG. 12 is a graph illustrating the separation efficiency of a faceted reflector versus a flat, planar reflector over time at a frequency of 2.185 MHz and two different powers (5 W and 10 W).

FIG. 11 graphically illustrates some of the advantages of using a reflector having a faceted surface over a flat, planar reflector. In FIG. 11, the lowest two lines, represented with square and diamond-shaped points, graph the impedance of a faceted reflector and flat reflector in thousands of Ohms along the left y-axis, and the upper two lines, represented with triangular and X-shaped points, graph the efficiency of a faceted reflector and a flat reflector in values of percentage along the right y-axis. The x-axis of FIG. 11 represents various operating frequencies in ten thousands of Hertz. FIG. 11 shows that for a yeast concentration of $1 \times 10^6$ cells/mL, the efficiency of a faceted reflector was noticeably greater than the efficiency of a flat, planar reflector. A similar result is noticed in FIG. 12, which graphically illustrates the efficiency of a faceted reflector versus the efficiency of a flat, planar reflector at a frequency of 2.185 MHz across a period of 80 minutes.

Referring again to FIG. 6, when the resonance is diminished or destroyed for facet 670 separated by distance $L_1$ from the piezoelectric material 600, the standing wave may "hop" to nearby facet 680, which corresponding $L_2$ distance from the piezoelectric material 600 satisfies the resonance conditions at the new speed of sound. Therefore, the device can automatically self-tune and/or readjust operation to maintain a strong multi-dimensional (e.g., three-dimensional) acoustic field regardless of the changing properties of the processed suspension, and can maintain the same operating frequency. The frequency operating point of the device can be determined by scanning. The operating conditions may change to reduce or eliminate resonance, e.g., because collected material drops out of the acoustic standing wave. When the operating conditions change, the frequency operating point may be re-determined by scanning frequencies to detect a desired operating frequency, e.g., based on optimizing efficiency of the acoustic standing wave in trapping and collecting particles. The automatic self-tuning or adjustment operation described above permits the scanning operation to be avoided. By avoiding the scanning operation, the productive operating time and/or effect of the acoustic standing wave can be increased.

The use of a reflector having a faceted surface contributes to improving performance with respect to uneven cell mass distribution. As the cell density and concentration can be different along the paths between the piezoelectric material/transducer and the reflector at different positions across the resonator cross section, the resonance conditions can be different along these paths. With a reflector having a faceted surface, different facets are available to re-tune the resonator along these paths in accordance to these local conditions. This level of optimization does not exist in a flat transducer-flat reflector system, even with agile frequency tuning.

Moreover, the use of a reflector having a faceted surface suppresses the standing wave corresponding to the "piston" mode of the flat piezoelectric material/transducer regardless of the frequency. Therefore, the range of operation frequencies available with the reflector having a faceted surface is wider than with a flat transducer-flat reflector system.

The differential vibrations of the non-planar face of the piezoelectric material allow for differential pressure waves to be generated from the non-planar face of the piezoelectric material. Local wave fronts with varying amplitudes may be generated from the non-planar face of the piezoelectric material with a single frequency input.

Figure 13:
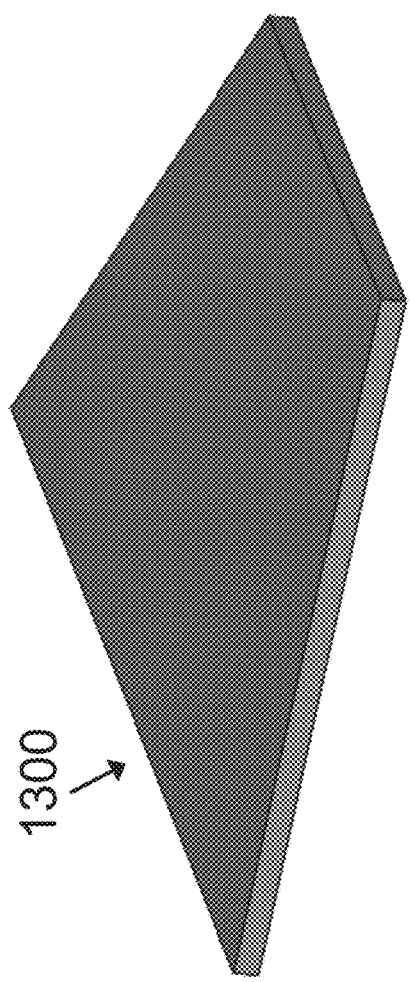
FIG. 13 illustrates a third embodiment of a piezoelectric material according to the present disclosure. The piezoelectric material has a non-symmetrical, trapezoidal shape.
Figure 14A:
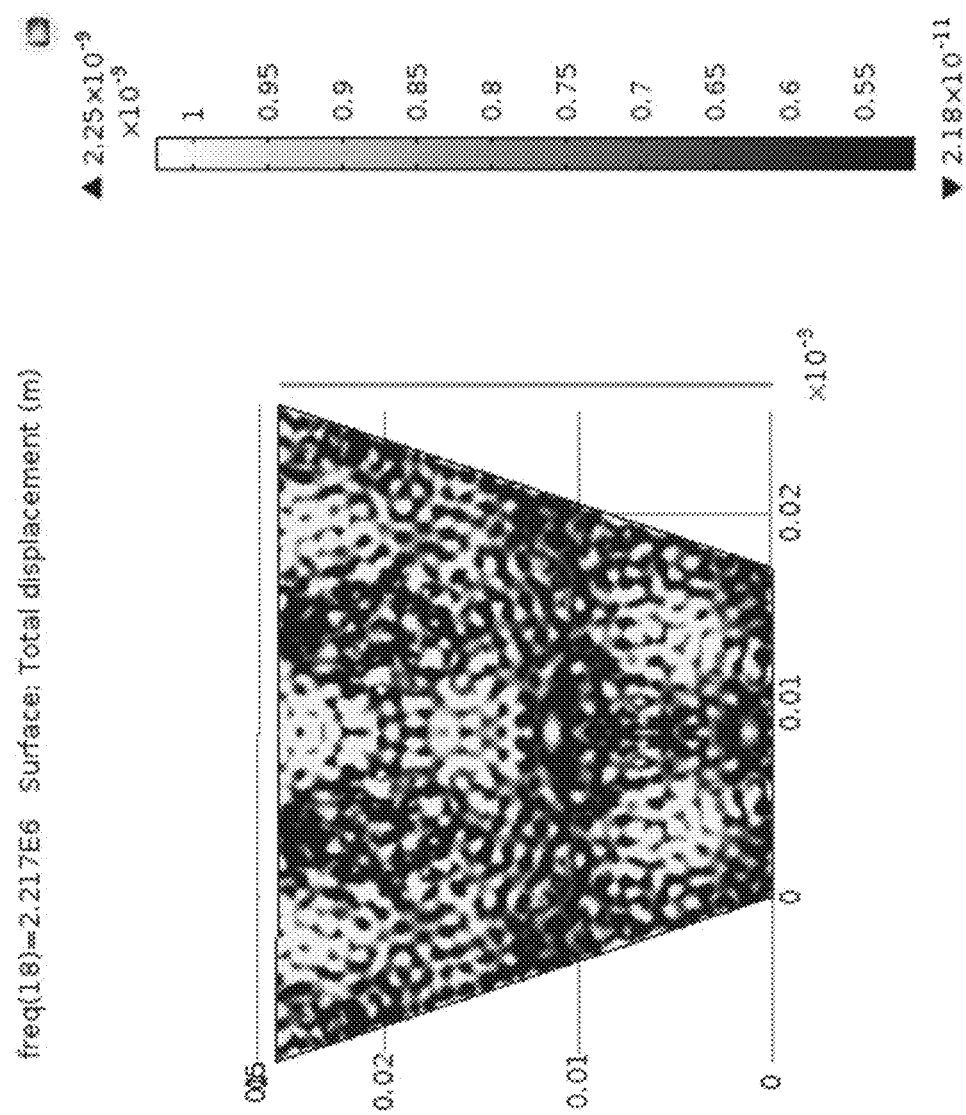
FIGS. 14A-14D illustrate the non-planar face of the trapezoidal piezoelectric material of FIG. 13 upon which asymmetric excitation patterns are generated at four different frequencies.
Figure 14B:
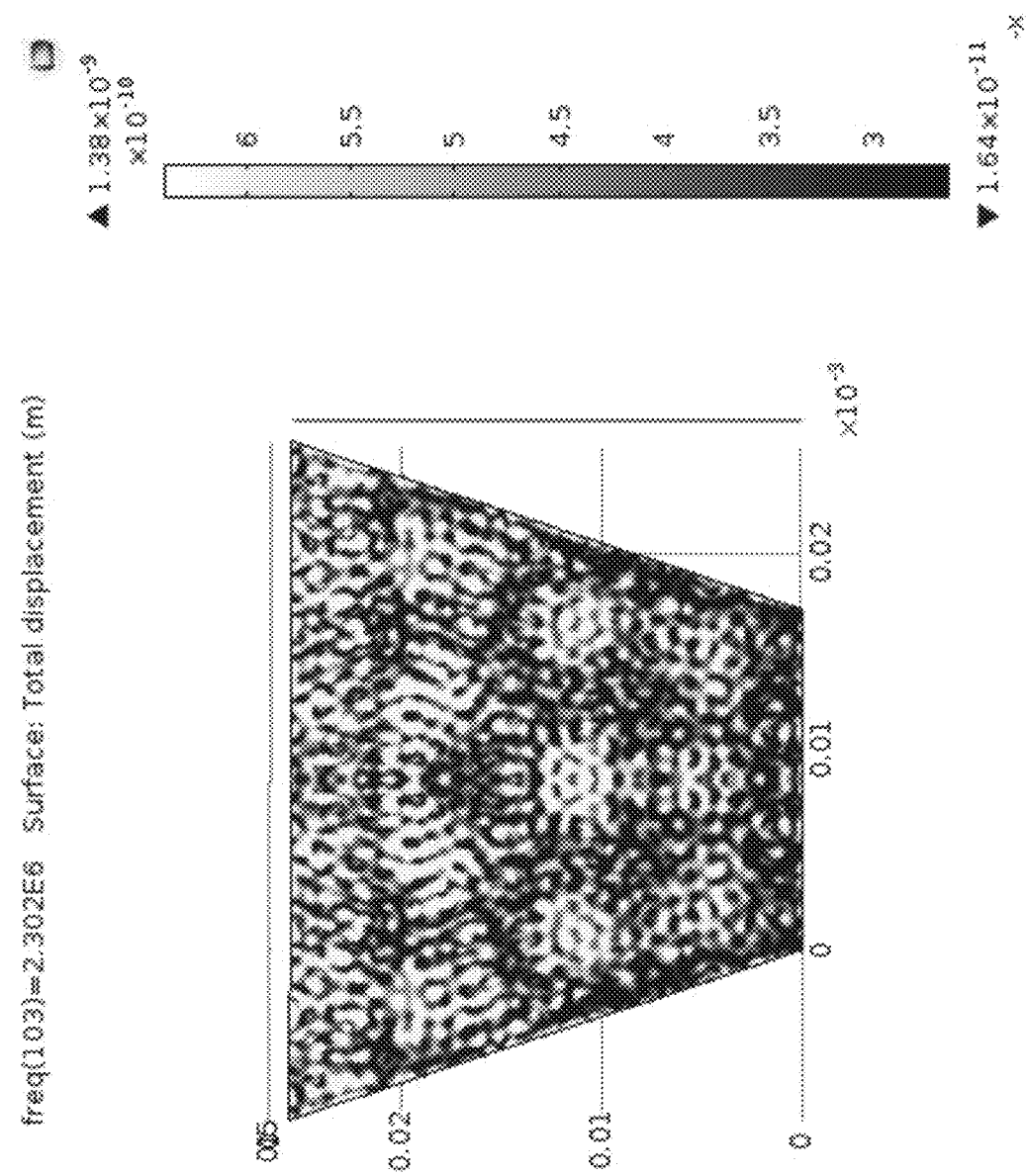
Figure 14C:
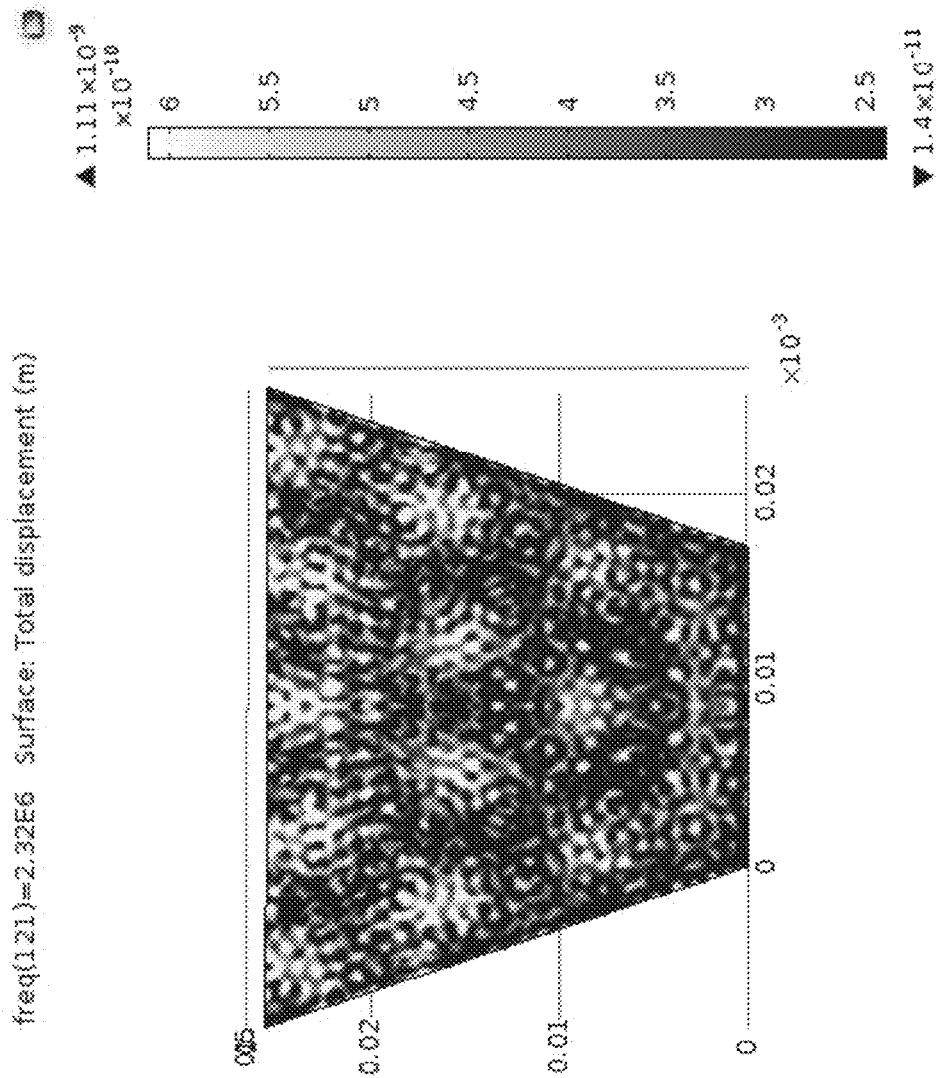
Figure 14D:
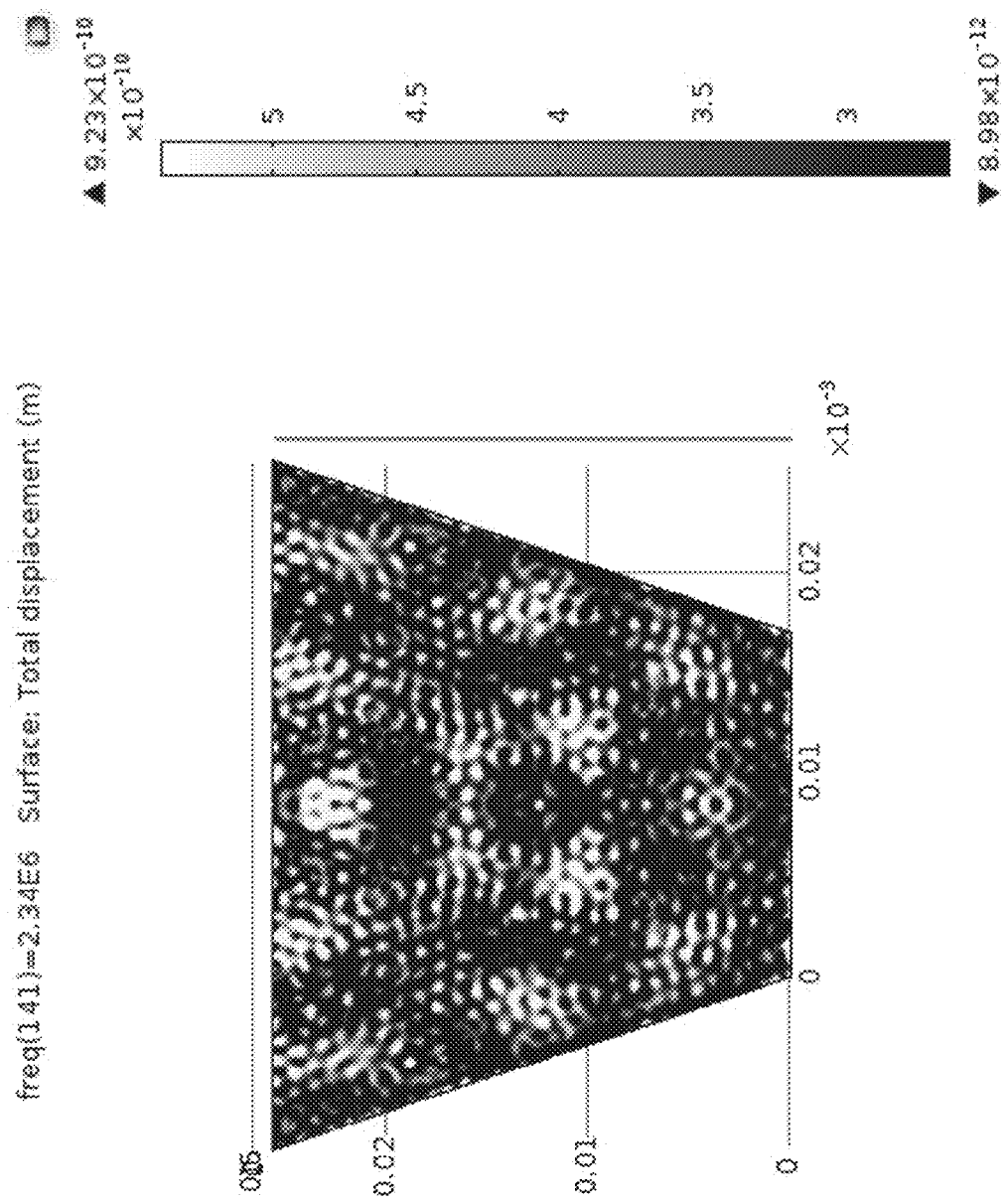

In certain embodiments, the piezoelectric material and/or reflector may be symmetrical or non-symmetrical in shape. The symmetry refers to the shape of the piezoelectric material as defined by its perimeter. In some examples, the perimeter of the piezoelectric material and/or the reflector forms a regular polygon or an irregular polygon. The piezoelectric crystal of FIG. 3, for example, is a square, which is symmetrical. However, piezoelectric material 1300 depicted in FIG. 13 has a trapezoidal shape, which can be symmetrical or non-symmetrical, e.g., with four different angles. Piezoelectric material 1300 may be shaped as an irregular polygon. Designing the piezoelectric material to have a symmetrical or non-symmetrical shape, or as a regular or irregular polygon, permits the acoustic transducer to be operated in modes that provide a desired number or arrangement of trapping lines. In some examples, the acoustic standing wave created by the piezoelectric material can generate trapping lines that are asymmetric.

FIGS. 14A-14D show four excitation patterns generated on the face of a trapezoidal piezoelectric material at four different frequencies. The shape of the piezoelectric material permits the production of certain modes of operation, which leads to the generation of trapping lines of particles inside the fluid in particular arrangements. The arrangement of the trapping lines can vary at different frequencies of excitation. In the example of the trapezoidal shaped piezoelectric material, the resulting trapping lines can produce less interference between adjacent trapping lines when continuous gravity separation of a secondary fluid or particulate from a host fluid is in operation. For example, when a trapezoidal piezoelectric material is placed in an acoustic chamber across from a reflector with a non-symmetrical or another shape, the trapping lines of the standing wave are spatially staggered. The staggering or spacing of the trapping lines provides paths for collected secondary fluid or particles in each trapping line to drop out of the acoustic standing wave without significantly impacting collected secondary fluid or particles in another trapping line.

In accordance with the present disclosure, the particles or secondary fluid collect at the nodes or anti-nodes of the acoustic standing wave, depending on the particles' or secondary fluid's acoustic contrast factor relative to the host fluid, forming clusters/clumps/agglomerates/coalesced droplets that continuously fall out of the acoustic standing wave when the clusters have grown to a size large enough to overcome the holding force of the acoustic standing wave (e.g. by coalescence or agglomeration) and the particle/secondary fluid density is higher than the host fluid, or to rise out of the acoustic standing wave when the particle/secondary fluid density is less than the host fluid. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable axial positions within the standing waves. When the acoustic radiation force exerted on the particles is stronger than the combined effect of fluid drag force and buoyancy and gravitational force, the particle is trapped within the acoustic standing wave field. This results in concentration, agglomeration and/or coalescence of the trapped particles. The strong lateral forces create rapid clustering of particles. Micron-sized particles, e.g., bacteria, mammalian cells, micro-algae, metal particles, yeast, fungi, lipids, oil droplets, red blood cells, white blood cells, platelets, etc., can thus be separated from the host fluid through enhanced gravitational separation. For the case of a suspension with several different particle sizes, it is possible by tuning of the system parameters to settle out the group of particles that are larger in size whereas the group of particles smaller in size can be kept in suspension. These two layers can then be harvested separately. A repeated process can then be used to fractionate groups of different sized particles according to size. In this regard, the multi-dimensional acoustic standing waves generated by each transducer can be of different frequencies.

One specific application for the acoustophoresis device is in the processing of bioreactor materials. It is important to be able to separate relatively larger cells and cell debris from the expressed materials that are in the host fluid. The expressed materials are composed of biomolecules such as recombinant proteins or monoclonal antibodies, and are the desired product to be recovered. Through the use of acoustophoresis, the separation of the cells and cell debris is very efficient and leads to very little loss of the expressed materials. This is an improvement over current filtration processes (depth filtration, tangential flow filtration, and the like), which show limited efficiencies at high cell densities, so that the loss of the expressed materials in the filter beds themselves can be up to 5% of the materials produced by the bioreactor. The use of mammalian cell cultures including Chinese hamster ovary (CHO), NS0 hybridoma cells, baby hamster kidney (BHK) cells, insect cells, and human cells (e.g. T-cells, B-cells, stem cells, red blood cells), and living/biological cells in general has proven to be a very efficacious way of producing/expressing the recombinant proteins and monoclonal antibodies used in pharmaceutical processes. The filtration of the mammalian cells and the mammalian cell debris through acoustophoresis aids in greatly increasing the yield of the bioreactor. As desired, the acoustophoresis process may also be coupled with a standard filtration process upstream or downstream, such as depth filtration, tangential flow filtration (TFF), or other physical filtration processes.

Efficient separation has been demonstrated for CHO cells, T-cells, and yeast cells with separation efficiencies in excess of 90% and more for cell concentrations from as little as 50,000 cells per ml of fluid to 80 million cells per ml of fluid. The flow rates of the acoustic separation devices according to the current embodiments vary from 1 ml/min for smaller scale devices to in excess of 50 liter/hour for larger scale devices.

In this regard, the acoustic contrast factor is a function of the ratio of particle to fluid compressibility and particle to fluid density. Most cell types present a higher density and lower compressibility than the medium in which they are suspended, so that the acoustic contrast factor between the cells and the medium has a positive value. As a result, the axial acoustic radiation force (ARF) drives the cells, with a positive contrast factor, to the pressure nodal planes, whereas cells or other particles with a negative contrast factor are driven to the pressure anti-nodal planes. The radial or lateral component of the ARF is larger than the combined effect of fluid drag force and gravitational force. The radial or lateral component drives the cells/particles to specific locations (points) within these planes where they cluster, clump, agglomerate, or coalesce into larger groups, which will then continuously gravity separate from the fluid.

Desirably, the ultrasonic transducer(s) generate a three-dimensional or multi-dimensional acoustic standing wave in the fluid that exerts a lateral force on the suspended particles to accompany the axial force so as to increase the particle trapping and clumping capabilities of the standing wave. Typical results published in literature state that the lateral force is two orders of magnitude smaller than the axial force. In contrast, the technology disclosed in this application provides for a lateral force to be of the same order of magnitude as the axial force (i.e. a multi-dimensional acoustic standing wave). However, in certain embodiments described further herein, combinations of transducers that produce both multi-dimensional acoustic standing waves and planar standing waves are contemplated. For purposes of this disclosure, a standing wave where the lateral force is of the same order of magnitude as the axial force is considered a "multi-dimensional acoustic standing wave."

Figure 15:
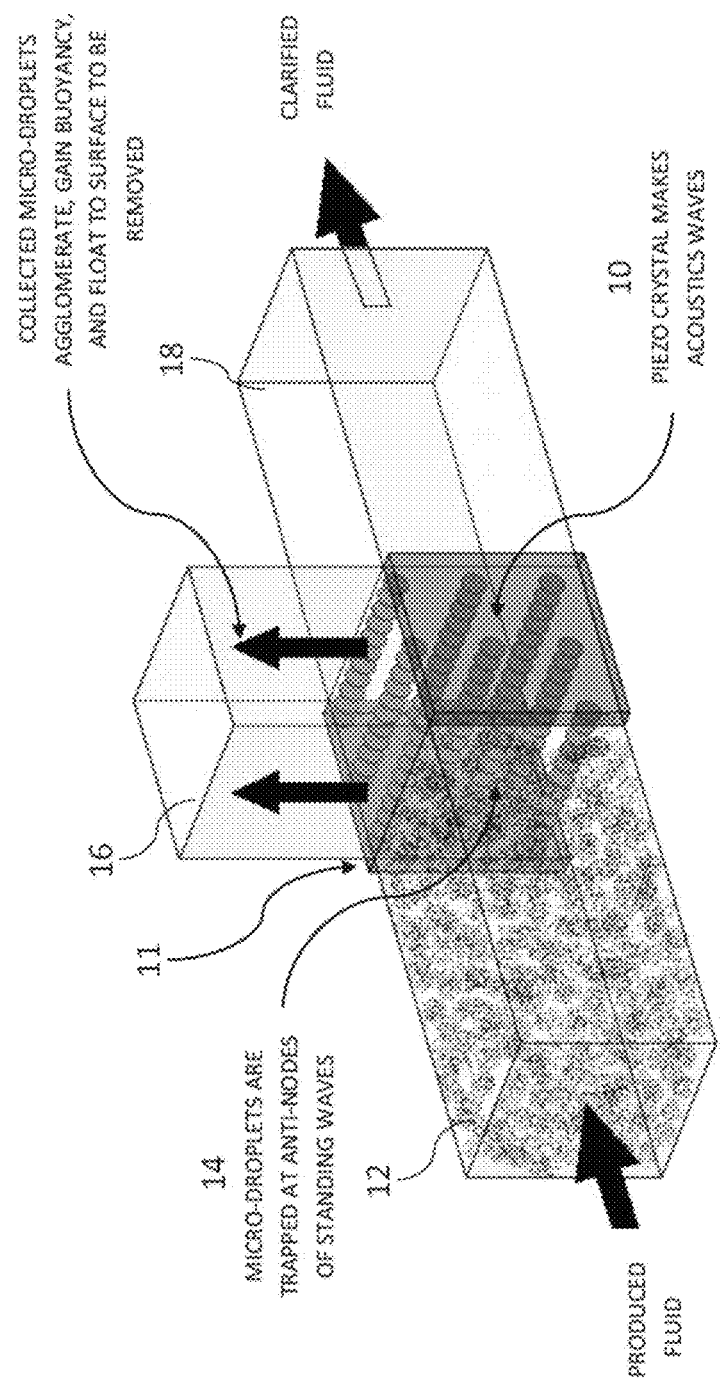
FIG. 15 is a diagram illustrating an acoustophoretic separation method according to the present disclosure for a second fluid or particle less dense than a host fluid.

A diagrammatic representation of an acoustic chamber for removing oil or other lighter-than-water material is shown in FIG. 15. Excitation frequencies typically in the range from hundreds of kHz to 10s of MHz are applied by transducer 10. One or more standing waves are created between the transducer 10 and the reflector 11. Incoming host fluid containing a secondary phase enters at inlet 12. Microdroplets are trapped in standing waves at the pressure anti-nodes 14 where they agglomerate, aggregate, clump, or coalesce, and, in the case of buoyant material, float to the surface and are discharged via an effluent outlet 16 located above the flow path. Clarified fluid (e.g. water) is discharged at outlet 18. The acoustophoretic separation technology can accomplish multi-component particle separation without any fouling at a much reduced cost.

Figure 16:
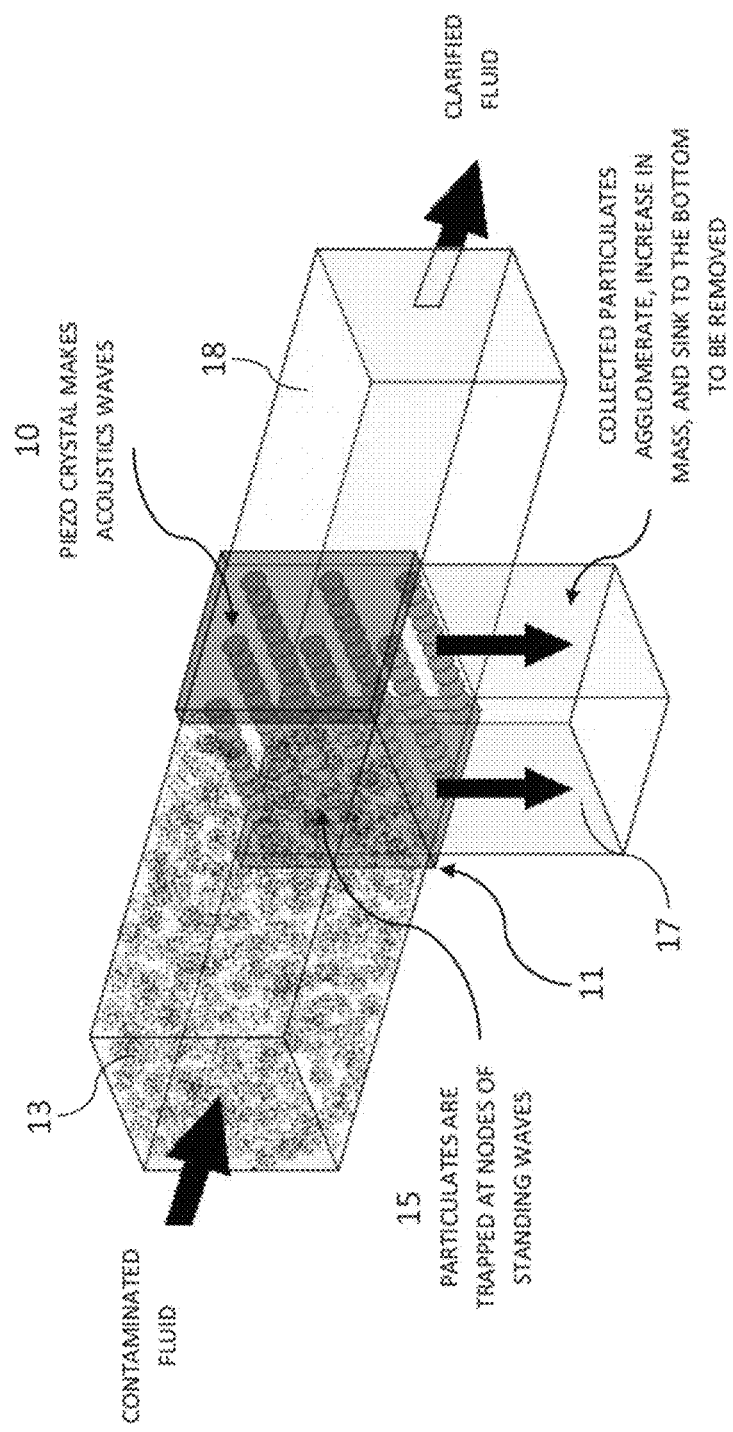
FIG. 16 is a diagram illustrating an acoustophoretic separation method according to the present disclosure for a second fluid or particle denser than a host fluid.

A diagrammatic representation of an acoustic chamber for removing contaminants or other heavier-than-water material is shown in FIG. 16. Excitation frequencies typically in the range from hundreds of kHz to 10s of MHz are applied by transducer 10. Incoming contaminated fluid enters through inlet 13. Contaminants are trapped in standing waves at the pressure nodes 15 where they agglomerate, aggregate, clump, or coalesce, and, in the case of heavier material, sink to the bottom collector and are discharged via an effluent outlet 17 located below the flow path. Clarified fluid is discharged at outlet 18.

As previously explained, the ultrasonic transducer and reflector are located on opposite sides of the acoustic chamber. In this way, one or more acoustic standing waves are created between the ultrasonic transducer and reflector.

Prior to discussing further optimization of the systems, it is helpful to provide an explanation now of how multi-dimensional acoustic standing waves are generated. The multi-dimensional acoustic standing wave needed for particle collection is obtained by driving an ultrasonic transducer at a frequency that both generates the acoustic standing wave and excites a fundamental 3D vibration mode of the transducer piezoelectric element. The multi-dimensional acoustic standing wave may be generated by distinct modes of the piezoelectric element such as a 3×3 mode that would generate multidimensional acoustic standing waves. A multitude of multidimensional acoustic standing waves may also be generated by allowing the piezoelectric element to vibrate through many different mode shapes. Thus, the element would excite multiple modes such as a 0×0 mode (i.e. a piston mode) to a 1×1 (the fundamental mode), to 2×2, 1×3, 3×1, 3×3, and other higher order modes and then cycle back through the lower modes of the element (not necessarily in straight order). This switching or dithering of the piezoelectric element between modes allows for various multi-dimensional wave shapes, along with a single piston mode shape, to be generated over a designated time.

It is also possible to excite or choose a frequency of excitation that excites multiple modes at the same time, each mode with a varying degree of displacement amplitude. Through this combination of multiple modes excited at the same time with varying displacement amplitude, it is possible to generate a superposition of multi-dimensional standing waves desirable for trapping, clustering, and separation of a secondary fluid or particle from a host fluid.

The scattering of the acoustic field off the particles results in a three dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). When the acoustic radiation force exerted on the particles is stronger than the combined effect of fluid drag force and buoyancy and gravitational force, the particles are trapped within the acoustic standing wave field. This results in concentration, agglomeration and/or coalescence of the trapped particles. Relatively large solids of one material can thus be separated from smaller particles of a different material, the same material, and/or the host fluid through enhanced gravitational separation.

The multi-dimensional standing wave generates acoustic radiation forces in both the axial direction (i.e., in the direction of the standing wave, between the transducer and the reflector, perpendicular to the flow direction) and the lateral direction (i.e., in the flow direction). As the mixture flows through the acoustic chamber, particles in suspension experience a strong axial force component in the direction of the standing wave. Since this acoustic force is perpendicular to the flow direction and the drag force, it quickly moves the particles to pressure nodal planes or anti-nodal planes, depending on the contrast factor of the particle. The lateral acoustic radiation force then acts to move the concentrated particles towards the center of each planar node, resulting in agglomeration or clumping. The lateral acoustic radiation force component has to overcome fluid drag for such clumps of particles to continually grow and then drop out of the mixture due to gravity. Therefore, both the drop in drag per particle as the particle cluster increases in size, as well as the drop in acoustic radiation force per particle as the particle cluster grows in size, must be considered for the acoustic separator device to work effectively. In the present disclosure, the lateral force component and the axial force component of the multi-dimensional acoustic standing wave are of the same order of magnitude. In this regard, it is noted that in a multi-dimensional acoustic standing wave, the axial force is stronger than the lateral force, but the lateral force of a multi-dimensional acoustic standing wave is much higher than the lateral force of a planar standing wave, usually by two orders of magnitude or more.

Some further explanation of the ultrasonic transducers used in the devices, systems, and methods of the present disclosure may be helpful as well. In this regard, the transducers use a piezoelectric element, usually made of PZT-8 (lead zirconate titanate). Such elements may have a 1 inch by 1 inch square shape with a thickness of 1 mm (nominal 2 MHz resonance frequency), and may also be of a larger size, such as a 1 inch by 3 inch shape with a 1 mm thickness, or smaller such as 0.5 inch by 0.5 inch. The thickness controls the resonance frequency, as the resonance frequency is inversely proportional to thickness. Each ultrasonic transducer module can have only one piezoelectric element, or can have multiple elements that each act as a separate ultrasonic transducer and are either controlled by one or multiple amplifiers. The piezoelectric element(s) can be crystalline, semi-crystalline, or non-crystalline. The transducer(s) is/are used to create a pressure field that generates forces of the same order of magnitude both orthogonal to the standing wave direction (lateral) and in the standing wave direction (axial).

Figure 17:
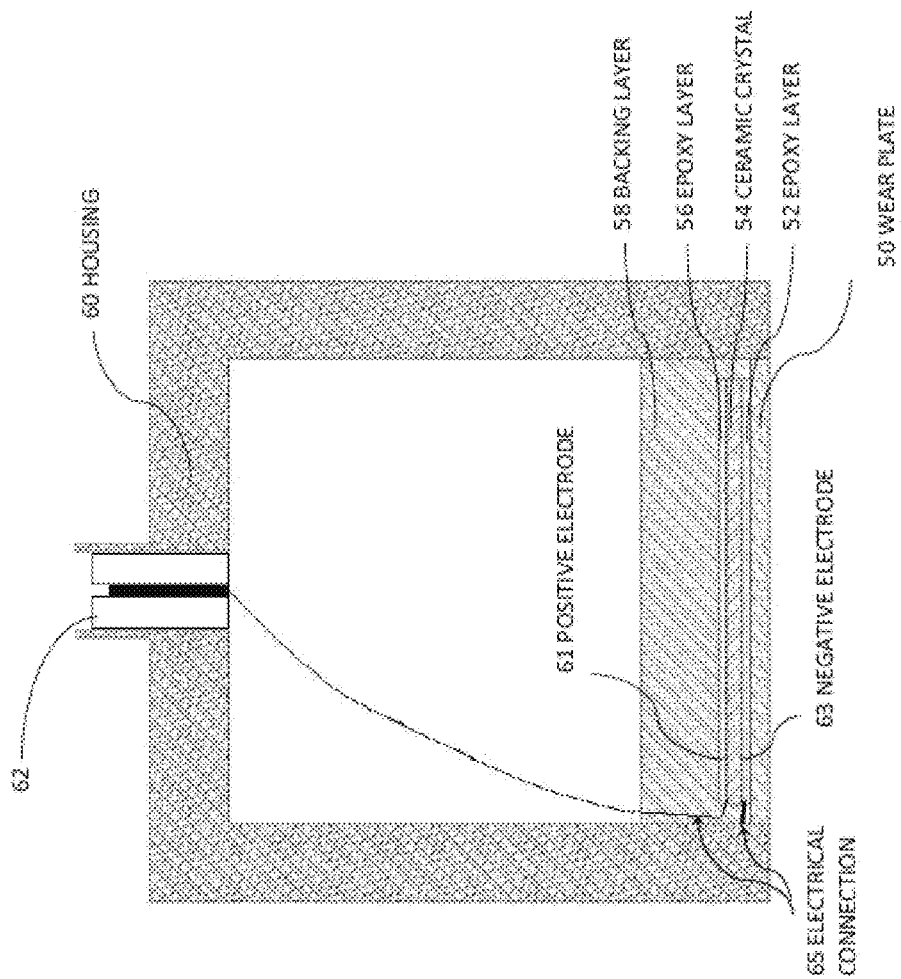
FIG. 17 is a cross-sectional diagram of a conventional ultrasonic transducer.

FIG. 17 is a cross-sectional diagram of a conventional ultrasonic transducer. This transducer has a wear plate 50 at a bottom end, epoxy layer 52, piezoelectric element 54 (e.g. a ceramic crystal made of, e.g. PZT), an epoxy layer 56, and a backing layer 58. On either side of the piezoelectric element, there is an electrode: a positive electrode 61 and a negative electrode 63. The epoxy layer 56 attaches backing layer 58 to the piezoelectric element 54. The entire assembly is contained in a housing 60 which may be made out of, for example, aluminum. An electrical adapter 62 provides connection for wires to pass through the housing and connect to leads 65 which attach to the piezoelectric element 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

Figure 18:
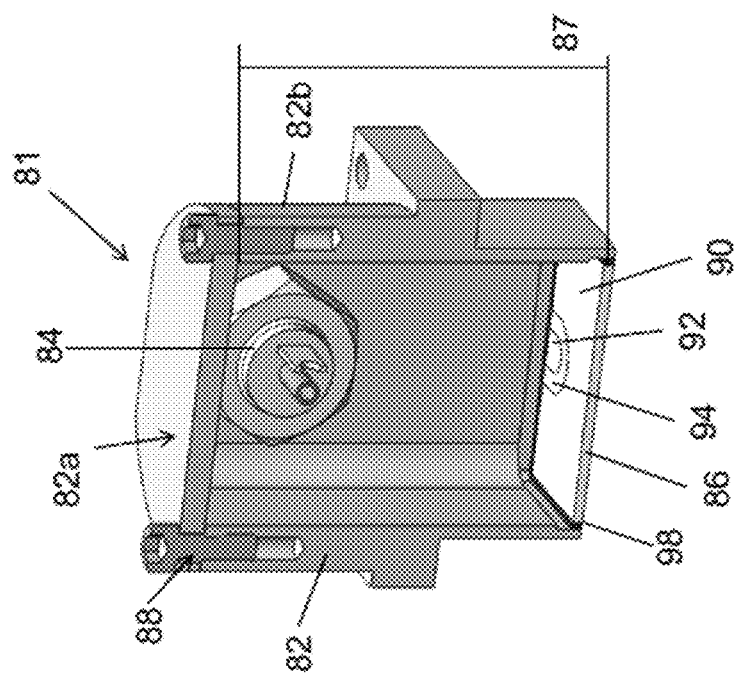
FIG. 18 is a cross-sectional diagram of an ultrasonic transducer according to the present disclosure. An air gap is present within the transducer, and no backing layer or wear plate is present.

FIG. 18 is a cross-sectional view of an ultrasonic transducer 81 of the present disclosure. Transducer 81 is shaped as a disc or a plate, and has an aluminum housing 82. The piezoelectric element can be, e.g., a mass of perovskite ceramic crystals, each consisting of a small, tetravalent metal ion, usually titanium or zirconium, in a lattice of larger, divalent metal ions, usually lead or barium, and O2-ions. As an example, in the embodiment shown in FIG. 18, a PZT (lead zirconate titanate) crystal 86 defines the bottom end of the transducer, and is exposed from the exterior of the housing. The crystal is supported on its perimeter by a small elastic layer 98, e.g. silicone or similar material, located between the crystal and the housing. Put another way, no wear layer is present. In particular embodiments, the crystal is an irregular polygon, and in further embodiments is an asymmetrical irregular polygon.

Figure 19:
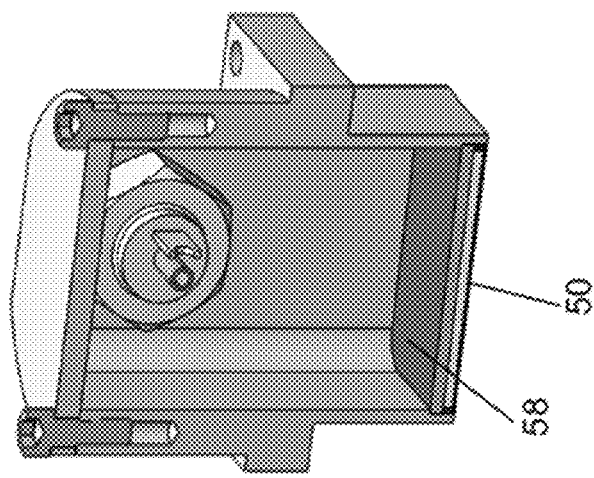
FIG. 19 is a cross-sectional diagram of an ultrasonic transducer according to the present disclosure. An air gap is present within the transducer, and a backing layer and wear plate are present.

Screws 88 attach an aluminum top plate 82a of the housing to the body 82b of the housing via threads. The top plate includes a connector 84 for powering the transducer. The top surface of the PZT crystal 86 is connected to a positive electrode 90 and a negative electrode 92, which are separated by an insulating material 94. The electrodes can be made from any conductive material, such as silver or nickel. Electrical power is provided to the PZT crystal 86 through the electrodes on the crystal. Note that the crystal 86 has no backing layer or epoxy layer. Put another way, there is an air gap 87 in the transducer between aluminum top plate 82a and the crystal 86 (i.e. the air gap is completely empty). A minimal backing 58 and/or wear plate 50 may be provided in some embodiments, as seen in FIG. 19.

The transducer design can affect performance of the system. A typical transducer is a layered structure with the piezoelectric element bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the piezoelectric element to vibrate in one of its eigenmodes (i.e. near eigenfrequency) with a high Q-factor. The vibrating piezoelectric element, such as, e.g., a ceramic crystal/disk, is directly exposed to the fluid flowing through the acoustic chamber.

Removing the backing (e.g. making the piezoelectric element air backed) also permits the element to vibrate at higher order modes of vibration with little damping (e.g. higher order modal displacement). In a transducer having a piezoelectric element with a backing, the element vibrates with a more uniform displacement, like a piston. Removing the backing allows the element to vibrate in a non-uniform displacement mode. The higher order the mode shape of the piezoelectric element, the more nodal lines the element has. The higher order modal displacement of the element creates more trapping lines, although the correlation of trapping line to node is not necessarily one to one, and driving the element at a higher frequency will not necessarily produce more trapping lines.

In some embodiments, the piezoelectric element may have a backing that minimally affects the Q-factor of the crystal (e.g. less than 5%). The backing may be made of a substantially acoustically transparent material such as balsa wood, foam, or cork which allows the element to vibrate in a higher order mode shape and maintains a high Q-factor while still providing some mechanical support for the element. The backing layer may be a solid, or may be a lattice having holes through the layer, such that the lattice follows the nodes of the vibrating element in a particular higher order vibration mode, providing support at node locations while allowing the rest of the element to vibrate freely. The goal of the lattice work or acoustically transparent material is to provide support without lowering the Q-factor of the piezoelectric element or interfering with the excitation of a particular mode shape.

Placing the piezoelectric element in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymers or polymer films. Organic and biocompatible coatings such as silicone or polyurethane are also usable as a wear surface.

The lateral force of the total acoustic radiation force (ARF) generated by the ultrasonic transducers of the present disclosure is significant and is sufficient to overcome the fluid drag force at high linear velocities up to 1 cm/s and beyond. For example, linear velocities through the devices of the present disclosure can be a minimum of 4 cm/min for separation of cells/particles, and can be as high as 1 cm/sec for separation of oil/water phases.

The lateral force of the acoustic radiation force generated by the transducer can be increased by driving the transducer in higher order mode shapes, as opposed to a form of vibration where the piezoelectric element effectively moves as a piston having a uniform displacement. The acoustic pressure is proportional to the driving voltage of the transducer. The electrical power is proportional to the square of the voltage. The voltage signal can have a sinusoidal, triangular, pulsed, or similar waveform and can have a frequency of from about 100 kHz to about 20 MHz. The transducer may be implemented as a thin piezoelectric plate, with electric field in the z-axis and primary displacement in the z-axis. The transducer is typically coupled on one side by air (i.e., the air gap within the transducer) and on the other side by the fluid mixture of the cell culture media. The types of waves generated in the thin piezoelectric plate are known as composite waves. A subset of composite waves in the piezoelectric plate is similar to leaky symmetric (also referred to as compressional or extensional) Lamb waves. The piezoelectric nature of the plate typically results in the excitation of symmetric Lamb waves. The waves are leaky because they radiate into the water layer, which result in the generation of the acoustic standing waves in the water layer. Lamb waves exist in thin plates of infinite extent with stress free conditions on its surfaces. Because the transducers of this embodiment are finite in nature, the actual modal displacements are more complicated.

Generally, the transducers of the present disclosure are used to create a pressure field that generates acoustic radiation forces of the same order of magnitude both orthogonal to the standing wave direction and in the standing wave direction. When the forces are roughly the same order of magnitude, particles of size 0.1 microns to 300 microns will be moved more effectively towards "trapping lines," so that the particles will not pass through the pressure field. Instead, the particles will remain within the acoustic chamber, from which they can advantageously be collected via specified outlets of the acoustophoretic device or otherwise recycled back to an associated bioreactor.

The acoustophoretic devices and methods described herein are useful for separating a second fluid or particulate from a host fluid. In this regard, the devices and methods of the present disclosure utilize higher order modal displacement of a piezoelectric material having a non-planar face, such that the piezoelectric material may be perturbed by a single excitation, yet still generate multi-dimensional acoustic standing waves.

Perturbation of the piezoelectric crystal in an ultrasonic transducer can generate a multidimensional acoustic standing wave. A piezoelectric crystal can be specifically designed to deform in a multimode fashion at designed frequencies, allowing for generation of a multi-dimensional acoustic standing wave. The multi-dimensional acoustic standing wave may be generated by distinct modes of the piezoelectric crystal such as the 3×3 mode that would generate multidimensional acoustic standing waves. A multitude of multidimensional acoustic standing waves may also be generated by allowing the piezoelectric crystal to vibrate through many different mode shapes. Thus, the crystal would excite multiple modes such as a 0×0 mode (i.e. a piston mode) to a 1×1, 2×2, 1×3, 3×1, 3×3, and other higher order modes and then cycle back through the lower modes of the crystal (not necessarily in straight order). This switching or dithering of the crystal between modes allows for various multidimensional wave shapes, along with a single piston mode shape to be generated over a designated time.

It is also possible to drive multiple ultrasonic transducers with arbitrary phasing. In other words, the multiple transducers may work to separate materials in a fluid stream while being out of phase with each other. Alternatively, a single ultrasonic transducer that has been divided into an ordered array may also be operated such that some components of the array will be out of phase with other components of the array.

Acoustic streaming is a fluid flow that may be caused or influenced by an acoustic wave propagating through a fluid. Acoustic streaming may be controlled in accordance with the present disclosure by modulating the drive signal to the acoustic transducer, such as by modulating the frequency or voltage amplitude of the input electrical signal, for example. The drive signal modulation may be amplitude modulation and/or frequency modulation. The duty cycle of the propagation of the standing wave may also be utilized to achieve certain results for trapping of materials. For example, the acoustic transducer may be turned on and/or shut off at different frequencies to obtain particular duty cycles for the ultrasonic standing wave to achieve desired results.

Figure 20:
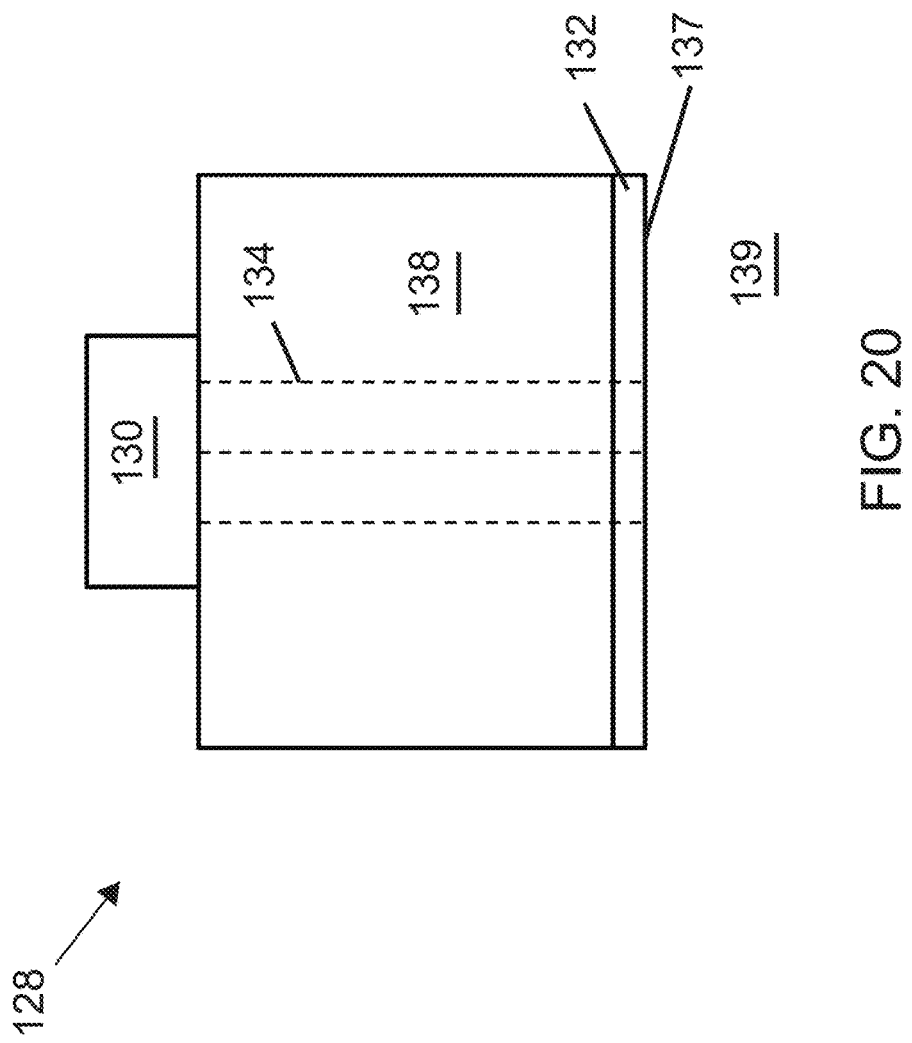
FIG. 20 is a schematic plan view of an acoustic chamber, illustrating the thin structure/reflector of the present disclosure.

The lateral force of the total acoustic radiation force (ARF) generated by the ultrasonic transducers of the present disclosure is significant and is sufficient to overcome the fluid drag force at relatively large linear velocities of up to 1 cm/s and greater. For example, linear velocities through the devices of the present disclosure can be as small as 4 cm/min for separation of cells/particles, and can be as large as 1 cm/sec for separation of oil/water phases. Flow rates can be as small as 25 mL/min, and can range as large as 40 mL/min to 1000 mL/min, or higher. This is true for batch reactors, fed-batch bioreactors and perfusion bioreactors. The present disclosure relates to acoustophoretic devices and structures that can make such devices more economical and also provide opportunities to enhance the range of applications in which they can be used. In this regard, FIG. 20 is a plan (top) view of an acoustic chamber 128. An ultrasonic transducer 130 is coupled to the chamber, such as by being affixed over an opening in acoustic chamber 128 to permit ultrasonic transducer 130 to generate an acoustic standing wave therein. A reflector 132 is implemented opposite to ultrasonic transducer 130, such as be being attached to, embedded in or forming a chamber wall opposite to ultrasonic transducer 130. Acoustic chamber 128 can be implemented as a closed chamber or as a flow chamber in which fluid flow is in/out of the plane of the figure.

Reflectors may be made from a solid material, such as a steel or aluminum plate. While a metal plate provides good acoustic reflection, it also adds weight to acoustic chamber 128. In the example illustrated in FIG. 20, reflector 132 is a thin structure that can provide a pressure release boundary. A pressure release boundary occurs when the acoustic pressure is zero at the interface.

As illustrated here in FIG. 20, reflector 132 has a substantially flat profile relative to chamber 128. The thin structure separates fluid 138 inside chamber 128 from a medium (typically air) 139 on the exterior of chamber 128. In operation, an ultrasonic propagating wave 134 (illustrated as dotted lines) generated by ultrasonic transducer 130 reflects off a boundary 137 created at a reflector/air interface. The acoustic standing wave passes through the material of reflector 132, and then reflect off the boundary 137. Reflector 132 can be made from an acoustically transparent material that does not impede the ultrasonic wave or that has a very low acoustic impedance. The acoustic wave reflects off the air at the interface of the thin structure and the air. For purposes of this disclosure, the term "reflector" can be used to refer to the structural component that separates the interior of an acoustic chamber from the exterior of the acoustic chamber and provides the interface with the air. In some example embodiments with fluid bordered by air, e.g., with a direct, fluid/air boundary, the transducer may be oriented to direct an acoustic standing wave through the fluid towards the fluid/air boundary. In this case, the fluid/air boundary is the free surface providing a pressure release boundary, with no other physical structure being necessary.

In specific embodiments, the thin structure has a thickness that is ½ or less of the wavelength of the ultrasonic transducer that it is being used with, and in more particular embodiments is at most 1/20 or at most 1/50 of the wavelength. Generally, this means the thin structure has a thickness of 5 or 10 microns to 1 millimeter.

In specific embodiments, the thin structure that provides the pressure release boundary is an acoustically transparent film, such as a plastic film. The plastic film is typically stretched within a frame. The plastic film can be transparent, thereby allowing visualization of the interior of chamber 128. The plastic film can be made of a material selected from the group consisting of olefins, polyurethanes, polyureas, polyesters, polystyrenes, polyamides, cellulosics, ionomers, polyvinyl chloride, polyvinyl butyral, polyvinylidene fluoride, polyvinylidene chloride, ethylene vinyl acetate, ethylene tetrafluoroethylene, polytetrafluoroethylene, and combinations thereof.

Figure 21:
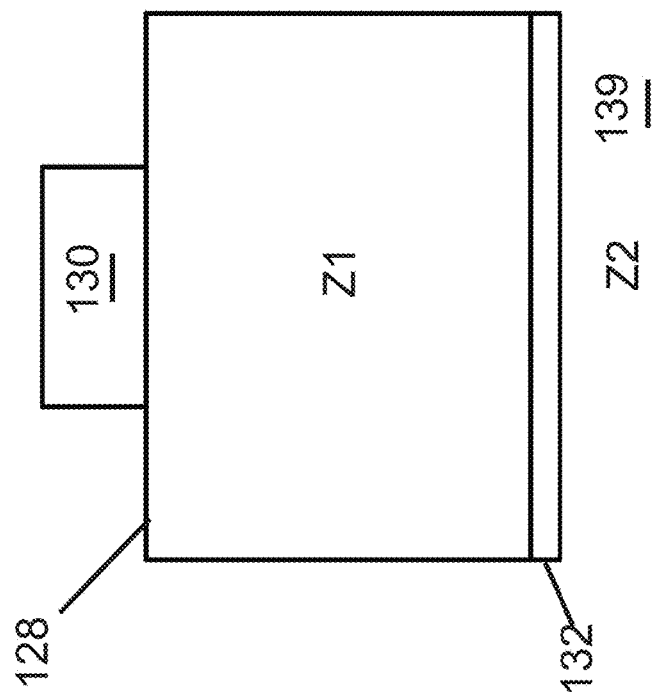
FIG. 21 is a schematic showing how the acoustic reflection coefficient is calculated for the device of FIG. 20.

FIG. 21 is a schematic explaining the operation of the thin structure that provides the pressure release boundary. Chamber 128 is depicted, as is ultrasonic transducer 130 and reflector 132. During operation, the flow chamber is filled with a fluid, typically water, that has an acoustic impedance $Z_1$, which is the product of the density of the fluid and the speed of sound in the fluid. When the thin structure is very thin, its acoustic impedance can be ignored. The medium 139 outside of the flow chamber (typically air) also has an acoustic impedance $Z_2$. As illustrated on the right-hand side, the fluid inside the chamber and the medium outside the chamber result in a system having an acoustic reflection coefficient R that is determined according to the formula:

$$R = \frac{Z_2 - Z_1}{Z_2 + Z_1}$$

The acoustic impedance is measured in Rayls (1 Rayl=1 kg/m²/sec). As an example of the efficacy of the thin structure, the acoustic impedance of air at 0° C. is 428 Rayls, and the acoustic impedance of fresh water is 1.48 million Rayls. Thus, the system would have an acoustic reflection coefficient of −0.999. This indicates that most of the acoustic energy will be reflected with a 180 degree phase change.

Figure 22A:
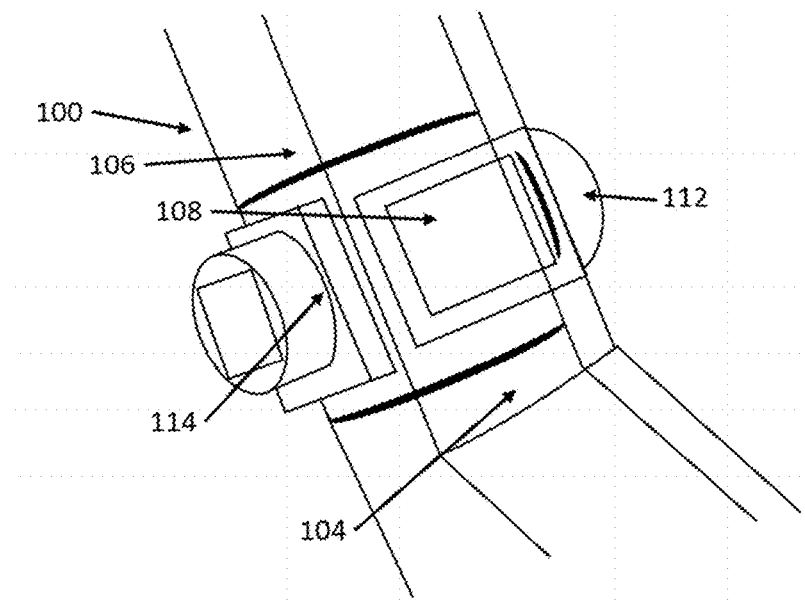
FIG. 22A is a picture of an acoustophoretic separator having one ultrasonic transducer and a transparent thin plastic film acting as the boundary.
Figure 22B:
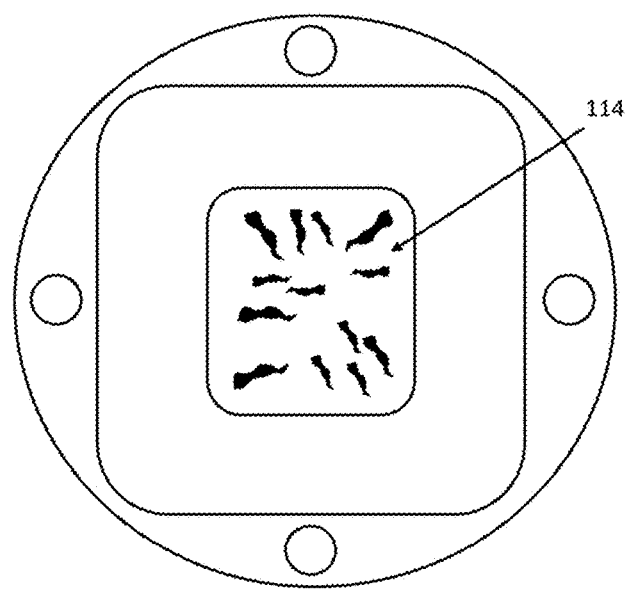
FIG. 22B is a picture showing the thin plastic film reflector.

Pictures showing an acoustophoretic particle separator 100 using an acoustically transparent film as a reflector are shown in FIG. 22A and FIG. 22B. Referring first to FIG. 22A, a multi-component liquid stream (e.g. water or other fluid) enters the inlet 104 and separated fluid exits at the opposite end via outlet 106. It should be noted that this liquid stream is usually under pressure when flowing through the separator. The particle separator 100 has a longitudinal flow channel 108 that carries the multi-component liquid stream past an ultrasonic transducer 112 and the acoustically transparent plastic film 114, which is located on the wall opposite the transducer. As seen here, a thin plastic film was used as the interface between the air and the fluid within the flow chamber. FIG. 22B is a picture of plastic film 114 during operation of the device.

Figure 23:
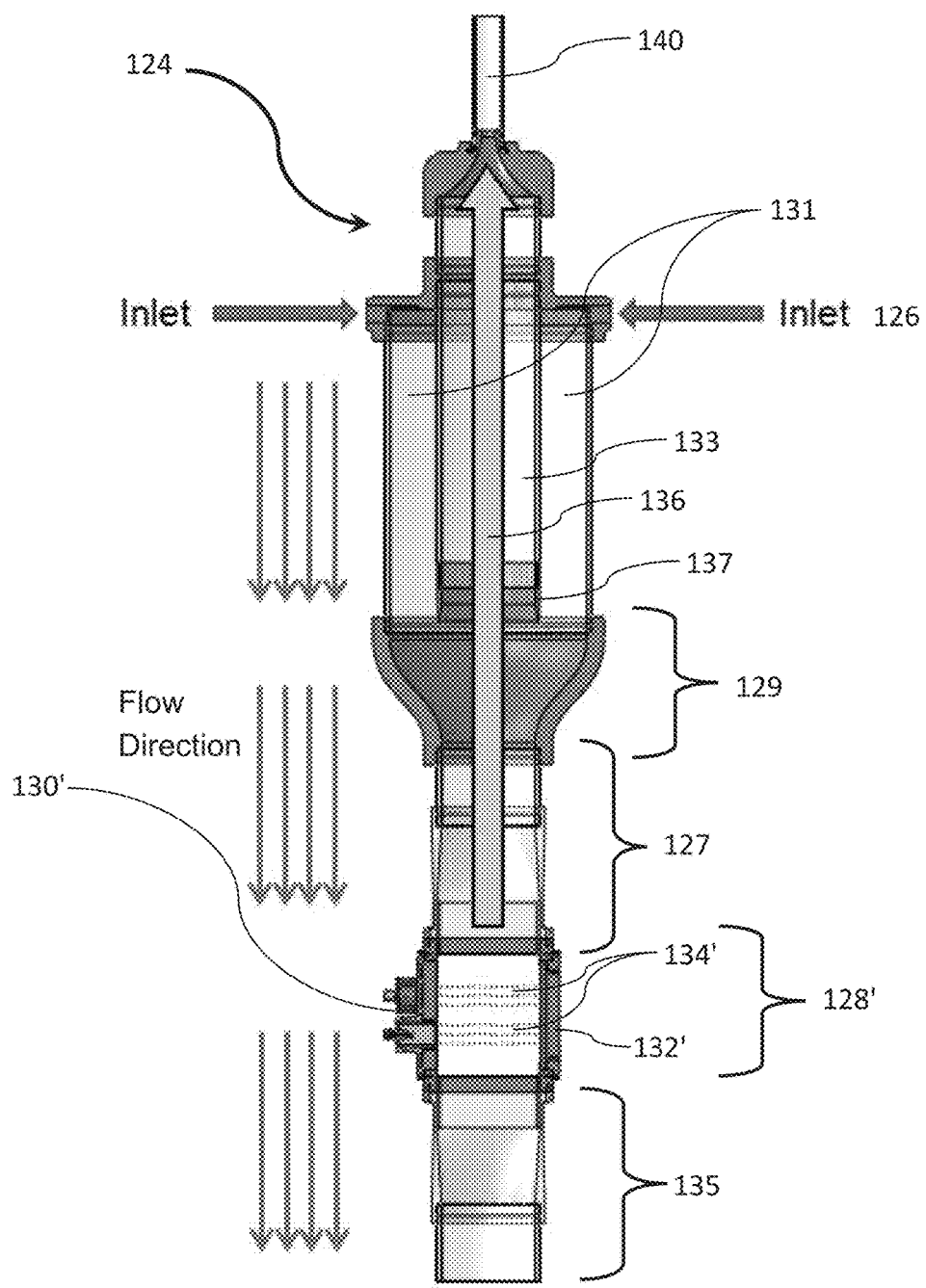
FIG. 23 is a cross-sectional view of an acoustophoretic separator in which the reflector of the present disclosure can be used.

FIG. 23 is a cross-sectional view of an acoustophoretic separation apparatus in which the thin structure reflector of the present disclosure (e.g. a thin plastic film) can be used. This is a figure of a 4" by 2.5" flow cross sectional area intermediate scale apparatus 124 for separating a host fluid from a buoyant fluid or particulate. The acoustic path length is 4". The apparatus is shown here in an orientation where the flow direction is downwards, which is used for separating less-dense particles from the host fluid. However, the apparatus may be essentially turned upside down to allow separation of particles which are heavier than the host fluid. Instead of a buoyant force in an upward direction, the weight of the agglomerated particles due to gravity pulls them downward. It should be noted that this embodiment is depicted as having an orientation in which fluid flows vertically. However, it is also contemplated that fluid flow may be in a horizontal direction, or at an angle.

A particle-containing fluid enters the apparatus through inlets 126 into an annular plenum 131. The annular plenum has an annular inner diameter and an annular outer diameter. Two inlets are visible in this illustration, though it is contemplated that any number of inlets may be provided as desired. In particular embodiments, four inlets are used. The inlets are radially opposed and oriented.

A contoured nozzle wall 129 reduces the outer diameter of the flow path in a manner that generates higher velocities near the wall region and reduces turbulence, producing near plug flow as the fluid velocity profile develops, i.e. the fluid is accelerated downward in the direction of the centerline with little to no circumferential motion component and low flow turbulence. This arrangement generates a chamber flow profile that is useful and potentially optimum for acoustic separation and particle collection. The fluid passes through connecting duct 127 and into a flow/separation chamber 128', which may be implemented by/as chamber 128. The contoured nozzle wall 129 adds a radial motion component to the suspended particles, moving the particles closer to the centerline of the apparatus and generating more collisions with rising, buoyant agglomerated particles. This radial motion will allow for optimum scrubbing of the particles from the fluid in the connecting duct 127 prior to reaching the separation chamber. The contoured nozzle wall 129 directs the fluid in a manner that generates large scale vortices at the entrance of the collection duct 133 to also enhance particle collection. Generally, the flow area of apparatus 124 is designed to be continually decreasing from the annular plenum 131 to the separation chamber 128' to assure low turbulence and eddy formation for better particle separation, agglomeration, and collection. The nozzle wall has a wide end and a narrow end. The term scrubbing is used to describe the process of particle/droplet agglomeration, aggregation, clumping or coalescing, that occurs when a larger particle/droplet travels in a direction opposite to the fluid flow and collides with smaller particles, in effect scrubbing the smaller particles out of the suspension.

Flow/separation chamber 128' includes a transducer array 130' and reflector 132' on opposite sides of the chamber. Transducer array 130' may be implemented by/as ultrasonic transducer 130. Reflector 132' can be the thin film-air interface described above in FIG. 20, with one side of the film exposed to the fluid within the flow chamber and the other side of the film exposed to the air outside of the flow chamber. In use, standing waves 134' are created between the transducer array 130' and reflector 132' as a thin film-air interface. These standing waves can be used to agglomerate particles, and this orientation is used to agglomerate particles that are buoyant (e.g. oil). Fluid, containing residual particles, then exits through flow outlet 135.

As the buoyant particles agglomerate, they eventually overcome the combined effect of the fluid flow drag forces and acoustic radiation force, and their buoyant force 136 is sufficient to cause the buoyant particles to rise upwards. In this regard, a collection duct 133 is surrounded by the annular plenum 131. The larger particles will pass through this duct and into a collection chamber 140. This collection chamber can also be part of an outlet duct. Collection duct 133 include a collection opening 137 that may be shaped to contribute to collecting buoyant particles moving upward with buoyant force 136. The collection duct and the flow outlet are on opposite ends of the apparatus.

It should be noted that the buoyant particles formed in the separation chamber 128' subsequently pass through the connecting duct 127 and the nozzle wall 129. This causes the incoming flow from the annular plenum to flow over the rising agglomerated particles due to the inward radial motion imparted by the nozzle wall. This allows the rising particles to also trap smaller particles in the incoming flow, increasing scrubbing effectiveness. The length of the connecting duct 127 and the contoured nozzle wall 129 thus increase scrubbing effectiveness. Especially high effectiveness is found for particles with a size of 0.1 microns to 20 microns, where efficiency is very low for conventional methods.

The design here provides an optimized velocity profile with low flow turbulence at the inlet to the flow chamber 128', a scrubbing length before the flow chamber to enhance particle agglomeration and/or coalescence before acoustic separation, and the use of the collection vortices to aid particle removal at the collection duct 133.

The transducer setup of the present disclosure creates a three dimensional pressure field which includes standing waves perpendicular to the fluid flow. The pressure gradients are large enough to generate acoustophoretic forces orthogonal to the standing wave direction (i.e., the acoustophoretic forces are parallel to the fluid flow direction) which are of the same order of magnitude as the acoustophoretic forces in the wave direction. This permits enhanced particle trapping, clumping and collection in the flow chamber and along well-defined trapping lines, as opposed to merely trapping particles in collection planes as in conventional devices. The particles have significant time to move to nodes or anti-nodes of the standing waves, generating regions where the particles can concentrate, agglomerate, and/or coalesce, and then gravity separate.

In some embodiments, the fluid flow has a Reynolds number of up to 1500, i.e. laminar flow is occurring. For practical application in industry, the Reynolds number is usually from 10 to 1500 for the flow through the system. The particle movement relative to the fluid motion generates a particle Reynolds number much less than 1.0 for that particle. The Reynolds number represents the ratio of inertial flow effects to viscous effects in a given flow field. For Reynolds numbers below 1.0, viscous forces are dominant in the flow field. This results in significant damping where shear forces are predominant throughout the flow. This flow where viscous forces are dominant is called Stokes flow. Wall contouring and streamlining have very little importance under such conditions. This is associated with the flow of very viscous fluids or the flow in very tiny passages, like MEMS devices.

The large annular plenum is followed by an inlet wall nozzle that accelerates and directs the fluid inward toward the centerline as shown in FIG. 23. The wall contour will have a large effect on the profile. The area convergence increases the flow average velocity, but it is the wall contour that determines the velocity profile. The nozzle wall contour will be a flow streamline, and is designed with a small radius of curvature in the separator.

In biological applications, it is contemplated that all of the parts of the system (e.g. the reaction vessel, tubing leading to and from the bioreactor, the temperature-regulating jacket, etc.) can be separated from each other and be disposable. The frequency of the transducers may also be varied to obtain optimal effectiveness for a given power.

The following examples are provided to illustrate the apparatuses, components, and methods of the present disclosure. The examples are merely illustrative and are not intended to limit the disclosure to the materials, conditions, or process parameters set forth therein.

EXAMPLES

Example 1

A polyolefin heat shrink film having a thickness of 0.60 mills (15.24 microns) was used as the acoustically transparent film to form a fluid-air interface, and was sandwiched in place using an empty transducer housing. This thickness is 1/50 of a wavelength when the transducer is operated at a frequency of 2.2 MHz. FIG. 22A is a picture of the test device.

FIG. 22B is a picture of the plastic film-air interface reflector during operation. The operation of a 5×5 trapping line mode can be seen through the plastic film, which is also optically transparent. The white trapping lines are visible through the plastic film. The overall efficiency of the apparatus dropped only 3% compared to using a steel reflector, which was within the range of measurement error.

Example 2

Acoustically transparent thin films 170 were attached to the face of the piezoelectric crystal (dimensions 1 inch by 1 inch) 172 of the ultrasonic transducer. Two different plastic thin films were used, one about 60 microns thick and one about 350 microns thick. A thin layer of ultrasonic transmission gel 174 was used to ensure there were no air pockets between the thin film and the crystal face. FIG. 24 is a picture of the square transducer and a diagram of the resulting structure. According to an example embodiment of the present disclosure, thin film 170 atop piezoelectric material 172 illustrated in FIG. 24 can be embossed and/or patterned to have a number of facets, similar to thin films discussed elsewhere herein. Such a non-planar thin film overlaid on piezoelectric material 172 can implement acoustic lensing for the transducer. The non-planar thin film can be configured and constructed to modulate the acoustic wave produced by piezoelectric material 172 to produce a desired acoustic profile from the transducer. Accordingly, such a non-planar thin film can be used as a pressure release boundary that is directly adjacent to piezoelectric material 172, in conjunction with gel 174.

Three types of reflectors were tested: a steel reflector, a thin plastic film reflector about 60 microns thick (R-ATF), and a thin plastic film reflector about 350 microns thick (R-TBC). Three different types of piezoelectric crystals were used: a crystal with the plastic thin film cover about 60 microns thick (C-ATF); a crystal with the plastic thin film cover about 350 microns thick (C-TBC); and an uncoated gamma sterilized crystal (UC).

These crystal/reflector combinations were tested to determine the effect on separation of a 3% yeast feed having 200 million cells/mL and starting turbidity as indicated. The feed flow rate was 30 ml/min, the concentrate output was 5 mL/min, and the permeate output was 25/mL/min. The power to the crystals was 7-11 watts, unless otherwise noted, and the frequency was 2.2455 MHz. The 350-micron-thick film was about one-half the thickness of the wavelength at this frequency.

After 30 minutes, the concentrate, permeate, and retentate were measured. The concentrate was the portion exiting the device that contained the concentrated yeast, along with some fluid. The permeate was the filtered portion exiting the device, which was mostly liquid with a much lower concentration of yeast. The retentate was the remaining substance left in the device after operation.

The results are provided in the following Table 1.

TABLE 1

| Reflector | Crystal | Starting Turbidity (NTU) | Turbidity Reduction (%) | Permeate Turbidity (NTU) | Concentrate Turbidity (NTU) | Retentate Turbidity (NTU) |
|---|---|---|---|---|---|---|
| Steel | UC | 5400 | 97 | 164 | 24000 | 7760 |
| R-ATF | UC (8 watts) | 5690 | 95 | 309 | 23440 | 8210 |
| R-ATF | UC (11 watts) | 5520 | 91 | 308 | 22480 | 9530 |
| Steel | C-ATF | 5130 | 98 | 134 | 24520 | 6600 |
| Steel | C-TBC | 5420 | 91 | 450 | 28160 | 8070 |
| R-TBC | UC | 5730 | 91 | 432 | 29480 | 8190 |

TABLE 1-continued

| Reflector | Crystal | Starting Turbidity (NTU) | Turbidity Reduction (%) | Permeate Turbidity (NTU) | Concentrate Turbidity (NTU) | Retentate Turbidity (NTU) |
|---|---|---|---|---|---|---|
| R-TBC | C-TBC (10-11 watts) | 5840 | 88 | 660 | 24120 | 7500 |
| R-TBC | C-TBC (19-20 watts) | 5690 | 93 | 379 | 31080 | 8700 |

As seen here, the turbidity was heavily reduced in the permeate and heavily increased in the concentrate, indicating the efficiency of the system.

Figure 25:
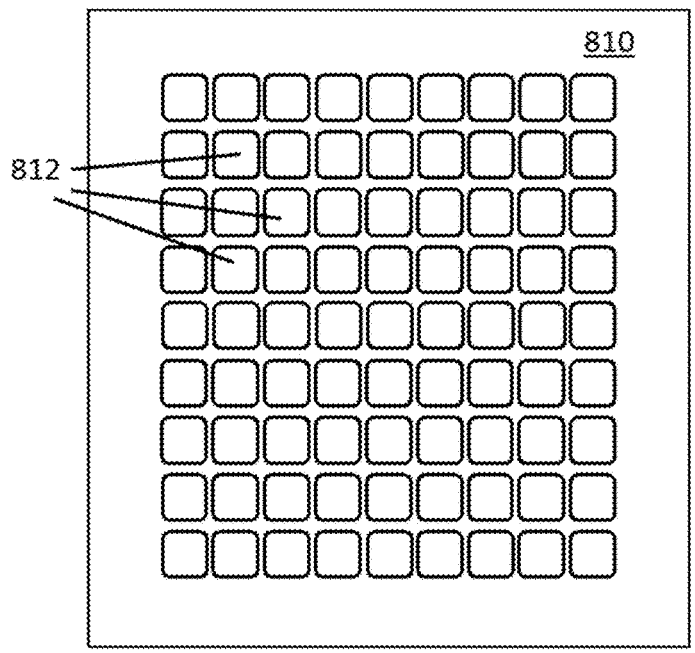
FIG. 25 is a picture of an embossed thin-film structure that can serve as a reflector boundary.

In some examples, a thin structure is provided as a reflector boundary, which may be constructed from a thin sheet of plastic or plastic film. As discussed herein, thin film structures that act as a pressure release boundary are sometimes referred to as a reflector for ease of reference and understanding. This reference is made with the understanding that it is the pressure release boundary that causes the acoustic reflection, e.g., the change in acoustic mediums, rather than the thin film structure itself. The thin structure may be patterned to be faceted or non-planar. FIG. 25 illustrates a thin, non-planar reflector 810. Reflector 810 has a number of facets 812 arranged in a grid pattern. Reflector 810 is a thin plastic material, such as a plastic film, which can be patterned with facets, such as by molding or stamping. Thin, non-planar reflector 810 may attain some or all of the features described herein with respect to the reflector implemented with thin material and with respect to the non-planar reflector or transducer. For example, thin, non-planar reflector 810 may implement a pressure release boundary, and may provide continuous tuning or improved pressure distribution or efficiency of the acoustic standing wave.

Figure 26:
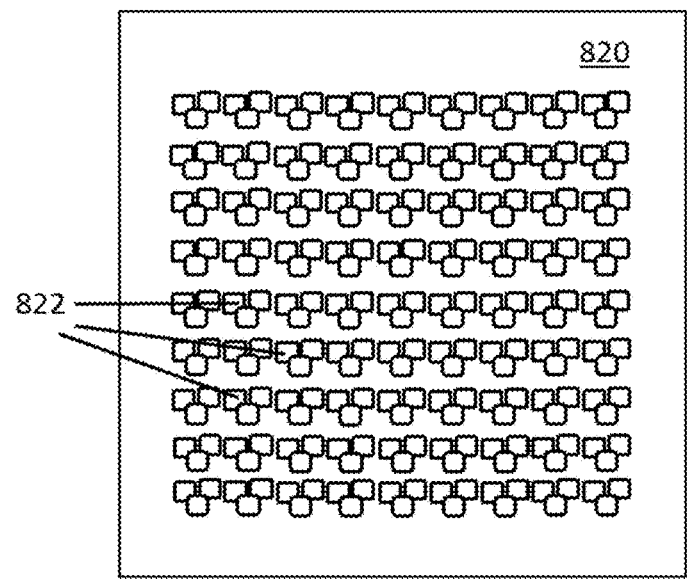
FIG. 26 is a picture of an embossed thin-film structure that can serve as a reflector boundary.

FIG. 26 illustrates another example of a thin structure reflector 820 that has a non-planar face. Reflector 820 has a grid of patterned facets 822 that include multiple surfaces in each grid location. Reflector 820 is a thin plastic material, such as a plastic film, which can be patterned with facets 822, such as by molding or stamping. Like reflector 810, reflector 820 may attain some or all of the features described elsewhere herein with respect to reflectors or implementing an acoustic standing wave.

Figure 27:
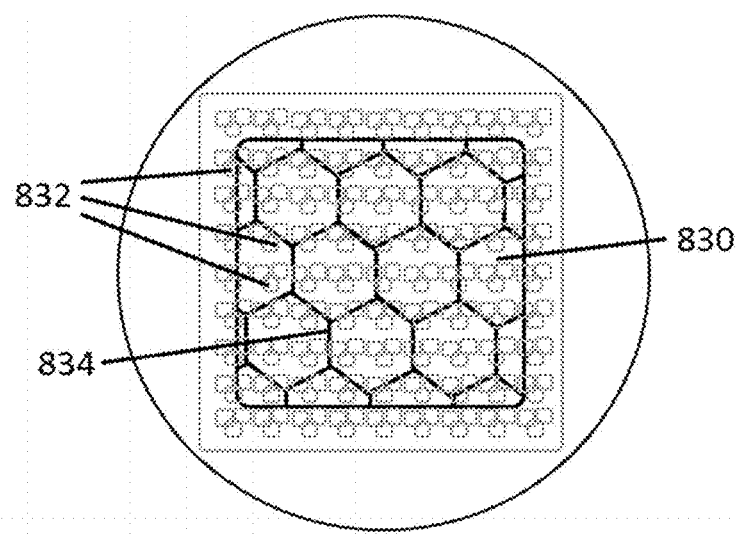
FIG. 27 is a picture of an embossed thin-film structure, which can serve as a reflector boundary, atop a support structure.

FIG. 27 illustrates another example of a thin structure reflector 830 that has a non-planar face. Reflector 830 has a grid of patterned facets 832 that include multiple surfaces in each grid location. Reflector 830 is a thin plastic material, such as a plastic film, which can be patterned with facets 832, such as by molding or stamping. Reflector 830 is overlaid on a support structure 834, which can provide additional support for reflector 830, for example, permitting reflector 830 to withstand greater fluid pressure without bowing or distorting significantly. Reflector 830 can be fastened to support structure 834. Reflector 830 can be located externally or internally to an acoustic chamber relative to support structure 834. As with other examples herein of non-planar thin film reflectors, reflector 830 can implement a pressure release boundary and can contribute to enhancements obtained with an acoustic standing wave in an acoustic chamber.

Figure 28:
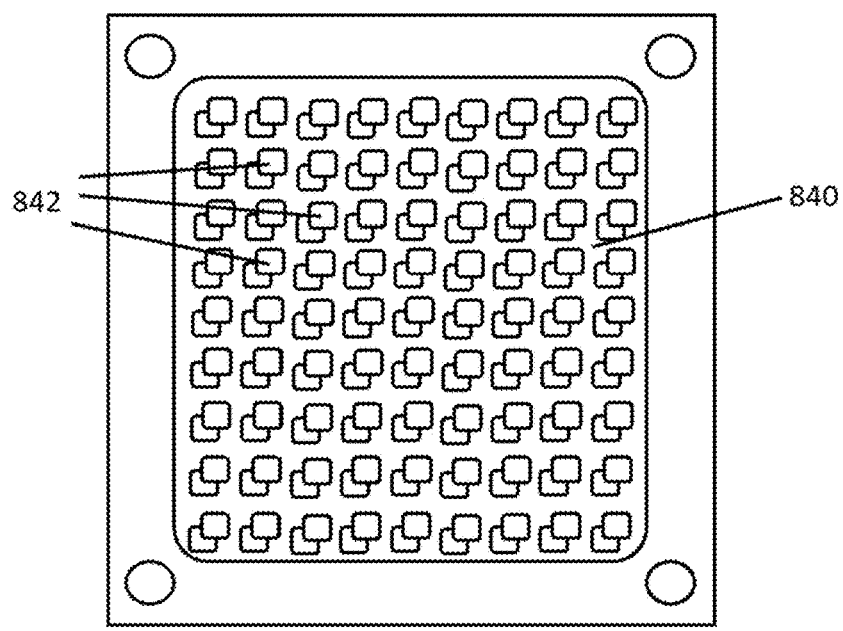
FIG. 28 is a picture of a non-planar transducer, which can be implemented as a thin structure, and can also serve as an embossing tool.

FIG. 28 illustrates an example acoustic transducer 840 that has a non-planar face. Acoustic transducer 840 has a grid of patterned facets 842 that include multiple surfaces in each grid location. As discussed elsewhere herein, acoustic transducer 840 can be implemented with a thin piezoelectric material. The thin piezoelectric material can include electrodes on either side of its major surfaces, which can be used, for example, to apply an electrical signal to excite acoustic transducer 840 generate an ultrasonic acoustic wave. As discussed elsewhere herein, individual facets 842 or layers of facets 842 can have a same or distinct electrode applied thereto. Each of the connected facets 842 can be actuated with an electrode, individual ones of which can be addressable, such as with a digital controller. For example, groups of facets 842 can be addressed and actuated with one or more electrodes connected thereto, at a certain frequency, while other facets 842 can be actuated at different frequencies, or remain unactuated. Transducer 840 may also be used as an embossing tool to form thin-film structures, such as a reflector 830 illustrated in FIG. 27. Such a technique may be implemented by stamping transducer 840 on a thin plastic film to form facets 832 in reflector 830.

Figure 29:
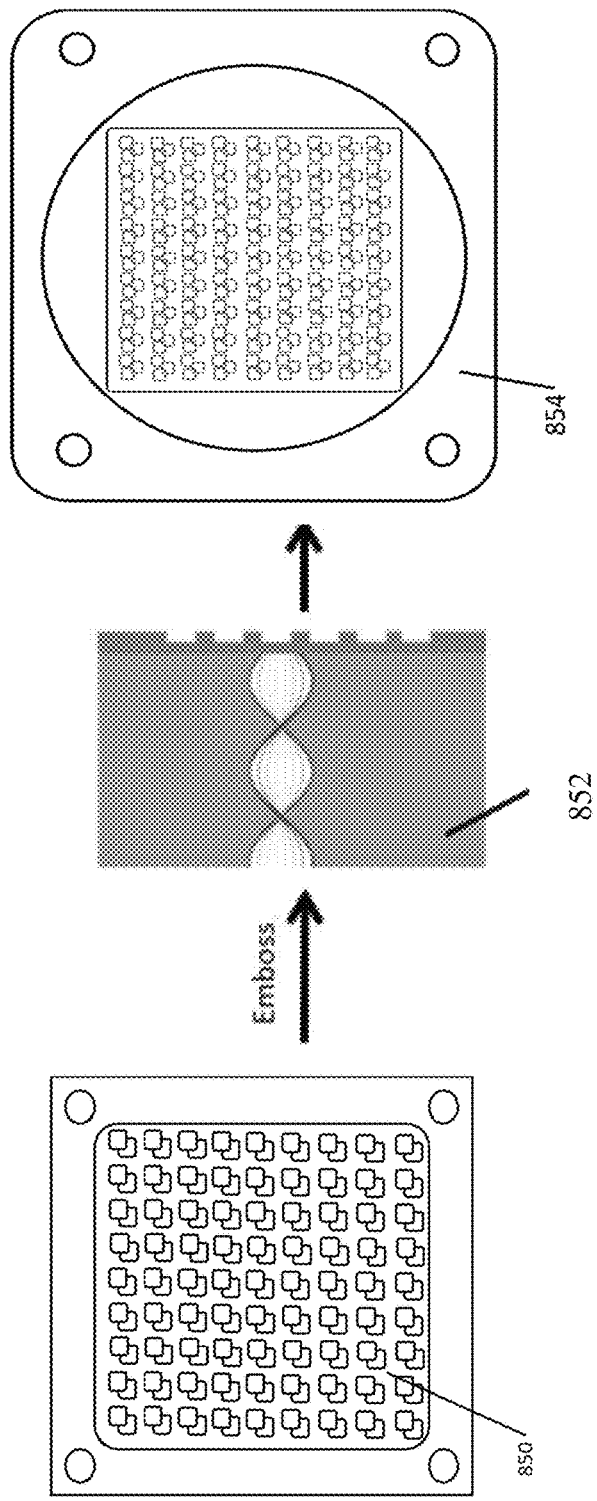
FIG. 29 is a series of images illustrating construction and use of an embossed, non-planar thin-film structure.

FIG. 29 illustrates a process for embossing a thin film to obtain a non-planar thin film reflector. A stamping form 850, which may be implemented as a steel or other metallic tool, including a non-planar metal reflector, can be used to emboss or impress a pattern onto a thin plastic film. The embossed thin plastic film can act as a pressure release boundary to permit reflection of an acoustic wave, as illustrated in picture 852. The non-planar thin plastic film may be affixed to a rigid structure, such as a housing for an acoustic flow chamber, as illustrated in picture 854.

Figure 30:
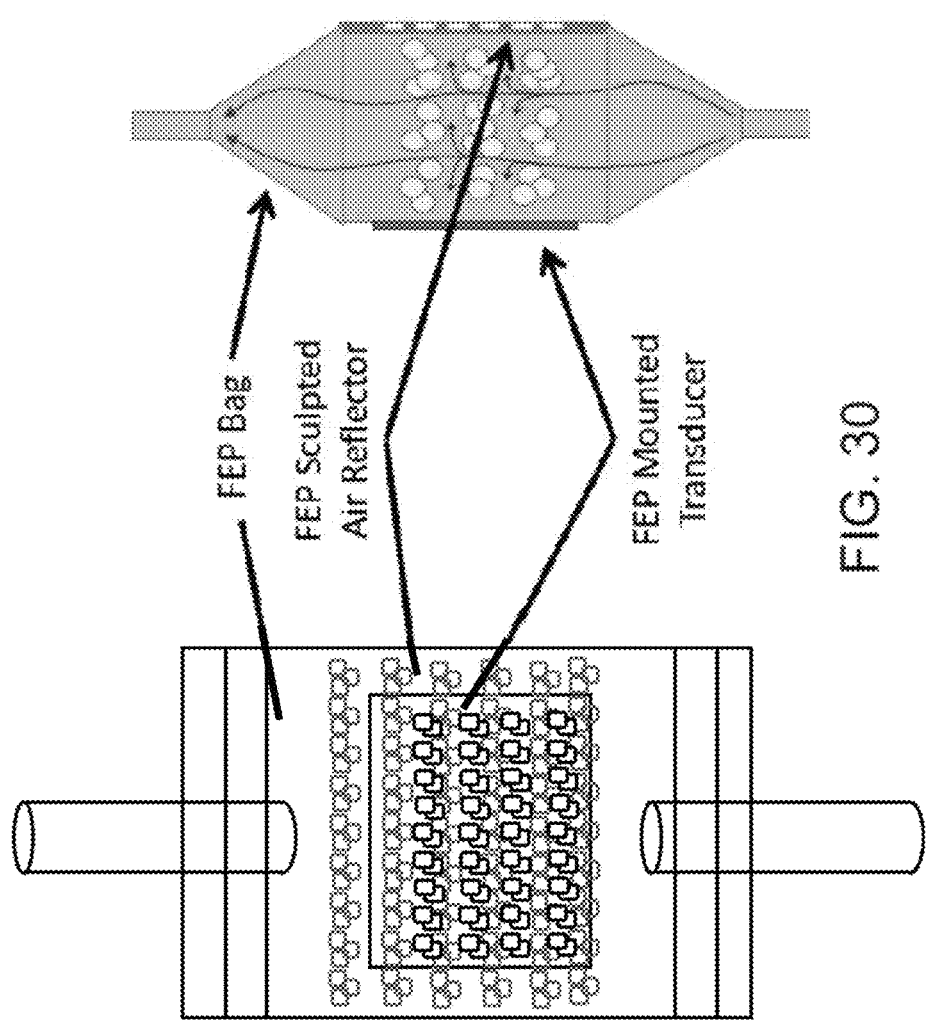
FIG. 30 is a picture and diagram of a disposable bag that can be used for cell culturing with an acoustic field across the bag.
Figure 31:
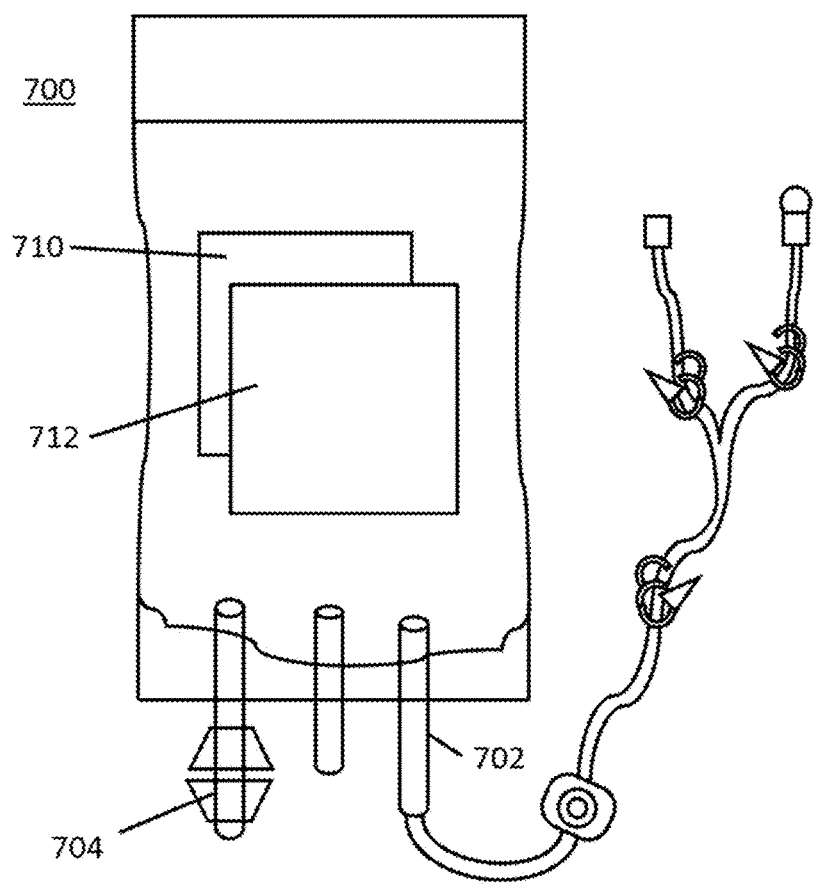
FIG. 31 is an illustration of an embodiment where the bioreactor is in the form of a flexible bag.

Piezoelectric material and/or a reflector may be constructed from or configured to be a thin structure. FIG. 30 illustrates a thin structure transducer composed of piezoelectric material and a thin structure reflector, or pressure release boundary, implemented for a disposable bag. The bag may have inlet and outlet connections for flowing the fluid mixture therethrough. Particles, such as cells, or droplets flowing through the bag can be separated from the fluid mixture by being trapped and/or retained by the acoustic standing wave generated between the piezoelectric material and the reflector. The reflector may be implemented in this case as the bag material, or as a patterned section of the bag material, which can implement a pressure release boundary between the fluid mixture and the external air. Clarified fluid mixture can flow out of the bag with the particles or droplets retained within the bag by the acoustic standing wave.

In some embodiments, a flexible bag or pouch is used as a bioreactor. FIG. 25 illustrates a flexible bag 700 used as a bioreactor. The interior volume of flexible bag 700 operates as the growth volume for cells. Flexible bag 700 includes an inlet 702 and an outlet 704. Opposite surfaces of the flexible bag can be flexible or stiff. One surface of flexible bag 700 includes an ultrasonic transducer 710, and an opposite surface includes a reflector 712 opposite to ultrasonic transducer 710. Ultrasonic transducer 710 and reflector 712 can be arranged and configured to generate an acoustic standing wave, including a multi-dimensional standing wave, within flexible bag 700. Flexible bag 700 is illustrated as having one inlet 702 and one outlet 704, however any number of inlets and outlets can be provided, including none of either. Not shown are other parts of the bioreactor, such as the agitator, pump, sensors, thermal jacket, etc., though such parts may or may not be used with flexible bag 700.

In use, cell culture media and cells drawn from a cell source, e.g., a patient or a reaction vessel, enter flexible bag 700 through inlet 702. The acoustic standing wave generated by ultrasonic transducer 710 in conjunction with reflector 712 traps the cell culture within the bag. Fluid, for example, cell culture media or wash media, and/or other material, is flowed through inlet 702. Fluid exits through outlet 704, which fluid can carry cell debris or waste. The added fluid may also be used to dislodge cells from the cell culture trapped in the acoustic standing wave, or can be used to remove biomolecules being expressed by the trapped cell culture. Flexible bag 700 can be arranged in any useful orientation, including that shown in FIG. 25 where gravity is downward toward inlet 702 and outlet 704. For example, flexible bag 700 may be oriented so that gravity is directed away from one or more of inlet 702 and outlet 704. In addition, or alternatively, inlet 702 and/or outlet 704 may be arranged at various locations on flexible bag 700, including the sides, top or bottom, separately or together, and generally in any useful orientation. Inlet 702 and/or outlet 704 may include additional structures inside flexible bag 700, such as extensions that are near or in the acoustic standing wave or that extend to a majority of the interior of flexible bag 700. Flexible bag 700 may also have one or more additional pockets (not shown) that are sealable and/or removable for holding concentrated cells that are clustered and dropout of the acoustic standing wave.

Ultrasonic transducer 710 and/or reflector 712 may be implemented as thin components that may be, in any combination, interior to, embedded in a wall of, or located externally to flexible bag 700. In some examples, flexible bag 700 may be constructed with a thin plastic film that can be used to implement reflector 712 as a thin film reflector, as discussed elsewhere herein. Ultrasonic transducer 710 and/or reflector 712 can be implemented to have a faceted or non-planar surface, as discussed elsewhere herein.

In some examples, the bioreactor includes a housing that may be rigid or flexible. The housing may take the form of a plastic, glass or metal container, for example. The housing may house the ultrasonic transducer and the reflector. A flexible polymeric bag or pouch, which may be implemented as flexible bag 700, with appropriate connections is placed within the housing and connected to the various inlets, outlets, and other components. The flexible bag itself may contain an inlet and/or an outlet. The flexible bag or pouch inserted within the housing may or may not include the ultrasonic transducer and/or reflector illustrated in FIG. 25. A cell culture is maintained within the flexible bag, which can be inserted into or removed from the housing. Accordingly, the cell culture subjected to acoustophoresis can be changed (e.g. to obtain other cells or biomolecules) by changing the bag containing the cell culture in the housing. This arrangement permits faster turnaround of the bioreactor.

In addition, or alternatively, the acoustophoresis process can be applied to a closed cell culture, using a flexible bag and/or the housing. For example, a flexible bag or pouch, similar to flexible bag 700, can be implemented with a sealed interior that holds the cell culture. The flexible bag can be constructed to have one or more additional pockets for holding concentrated cells, for example, as discussed elsewhere herein. The closed cell culture can be exposed to the acoustic standing wave to, for example, concentrate cells in the bag. The closed cell culture represents a closed system that avoids contamination and other advantageous features.

Figure 32:
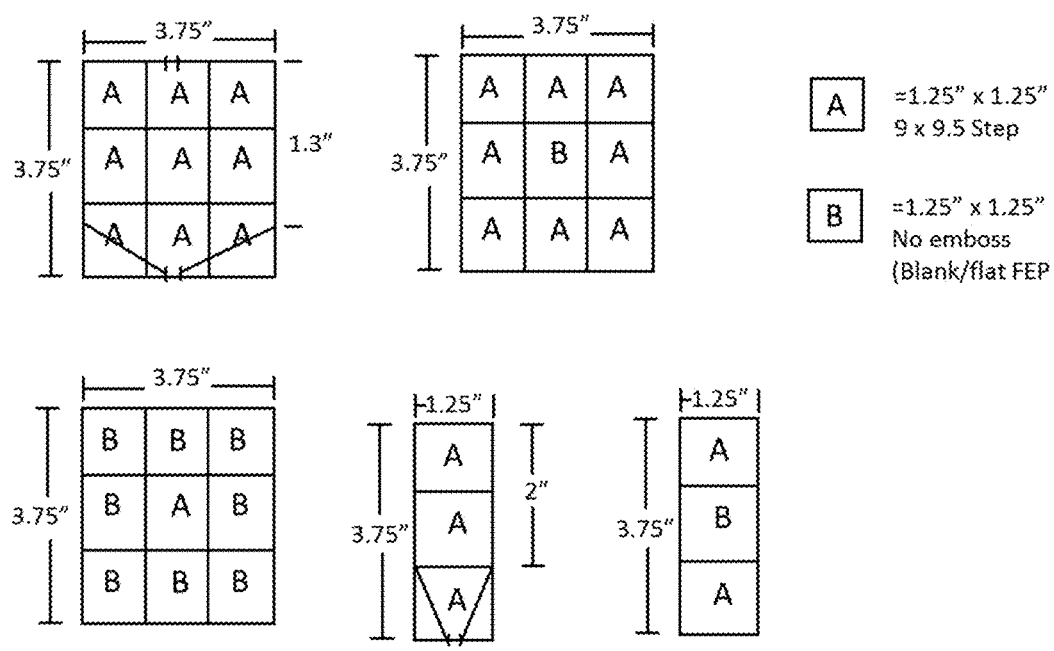
FIG. 32 is an illustration of different configurations for a non-planar transducer or reflector boundary material.

FIG. 32 illustrates a number of configurations of non-planar reflectors or transducers. Different non-planar sections of the transducer or reflector face can be provided, as illustrated. In some implementations, the non-planar face of the transducer or reflector can generate a number of small nodal lines or multi-dimensional acoustic standing waves. If the face of the transducer or reflector is implemented in accordance with configuration 860, a central portion labeled B can be planar. The implementation of a planar region in the face of the transducer or reflector provides a region for collection of particles or droplets that can grow to a significant size before dropping out of the acoustic standing wave. The larger size particles or droplets can improve the collection efficiency of the transducer or reflector by collecting particles from the non-planar regions labeled A in FIG. 32.

The reaction vessel may be tubular, cubic, or another polygonal shape. The flow of the nutrient fluid stream through the reaction vessel of the bioreactor may be vertical, horizontal, or any angle in between. The combination of the ultrasonic transducers and the reflectors set up the resonant waves in the interior of the reaction vessel. The standing waves hold the cell culture at net zero pressure nodes. The ultrasonic transducers and reflectors may be set perpendicular or at another angle to the fluid flow of the nutrient fluid stream through the acoustic bioreactor. The reflector may be flat or non-planar. In addition, or alternatively, two facing transducers may be employed and actuated to form an acoustic standing wave therebetween. The facing transducers may be thin components, as discussed elsewhere herein. In addition, or alternatively, the reflector may be implemented as an active piezoelectric element that is not actuated. Such a reflector can change its shape to contribute to establishing and maintaining an acoustic standing wave or resonance.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known processes, structures, and techniques have been shown without unnecessary detail to avoid obscuring the configurations. This description provides example configurations only, and does not limit the scope, applicability, or configurations of the claims. Rather, the preceding description of the configurations provides a description for implementing described techniques. Various changes may be made in the function and arrangement of elements without departing from the scope of the disclosure.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Also, configurations may be described as a process that is depicted as a flow diagram or block diagram. Although each may describe the operations as a sequential process, many of the operations can be performed in parallel or concurrently. In addition, the order of the operations may be rearranged. A process may have additional stages or functions not included in the figure.

Having described several example configurations, various modifications, alternative constructions, and equivalents may be used without departing from the scope of the disclosure. For example, the above elements may be components of a larger system, wherein other structures or processes may take precedence over or otherwise modify the application of the disclosed subject matter. Also, a number of operations may be undertaken before, during, or after the above elements are considered. Accordingly, the above description does not bound the scope of the claims.

The present disclosure has been described with reference to exemplary embodiments. Modifications and alterations may occur to others upon reading and understanding the preceding detailed description. It is intended that the present disclosure be construed as including all such modifications and alterations insofar as they come within the scope of the appended claims or the equivalents thereof.

The invention claimed is:

1. An acoustophoretic separation apparatus, comprising:
   a chamber for containing a fluid;
   at least one ultrasonic transducer acoustically coupled to the chamber; and
   a thin structure with a planar face that includes a non-planar surface facing the at least one ultrasonic transducer that is configured to reflect at least some acoustic energy from the at least one ultrasonic transducer.

2. The apparatus of claim 1, wherein the thin structure is a plastic film.

3. The apparatus of claim 2, wherein the plastic film is made of a material selected from the group consisting of olefins, polyurethanes, polyureas, polyesters, polystyrenes, polyamides, cellulosics, ionomers, polyvinyl chloride, polyvinyl butyral, polyvinylidene fluoride, polyvinylidene chloride, ethylene vinyl acetate, ethylene tetrafluoroethylene, polytetrafluoroethylene, and combinations thereof.

4. The apparatus of claim 1, wherein the thin structure is configured to provide a pressure release boundary.

5. The apparatus of claim 1, wherein the at least one ultrasonic transducer includes a non-planar surface.

6. The apparatus of claim 1, wherein the at least one ultrasonic transducer is a thin structure.

7. The apparatus of claim 1, wherein the thin structure has a thickness that is ½ or less of the wavelength emitted by the at least one ultrasonic transducer.

8. The apparatus of claim 1, wherein the at least one ultrasonic transducer is operable to generate a multi-dimensional acoustic standing wave in the chamber.

9. The apparatus of claim 8, wherein the multi-dimensional acoustic standing wave includes an axial force component and a lateral force component that are of the same order of magnitude.

10. The apparatus of claim 1, wherein the at least one ultrasonic transducer has a face that contacts fluid within the flow chamber, the face being coated with a wear layer comprising chrome, electrolytic nickel, electroless nickel, p-xylylene, glassy carbon, or urethane.

11. An acoustophoretic method, comprising:
    receiving a mixture of a host fluid and a second fluid or particulate in a container;
    generating an acoustic standing wave in the container using a thin acoustic component with a planar face that includes a non-planar surface; and
    collecting droplets of the second fluid or particles in the acoustic standing wave to separate the second fluid or particulate from the host fluid.

12. The method of claim 11, further comprising flowing the host fluid through the container.

13. The method of claim 11, further comprising closing off the container to provide a closed container.

14. The method of claim 11, wherein the thin acoustic component is an ultrasonic transducer.

15. The method of claim 14, wherein the ultrasonic transducer is operable to generate a multi-dimensional acoustic standing wave in the chamber.

16. The method of claim 15, wherein the multi-dimensional acoustic standing wave includes an axial force component and a lateral force component that are of the same order of magnitude.

17. The method of claim 14, wherein the ultrasonic transducer includes a face that contacts fluid within the container, the face being coated with a wear layer comprising chrome, electrolytic nickel, electroless nickel, p-xylylene, glassy carbon, or urethane.

18. The method of claim 11, wherein the thin acoustic component is a reflector configured to provide a pressure release boundary.

19. The method of claim 11, further comprising a free surface that is configured to provide a pressure release boundary for the acoustic standing wave.

20. An apparatus, comprising:
    a chamber for containing a fluid;
    at least one ultrasonic transducer acoustically coupled to the chamber;
    a thin structure with a planar face that includes a non-planar surface facing the at least one ultrasonic transducer that is configured to reflect at least some acoustic energy from the at least one ultrasonic transducer with an acoustic reflection coefficient from about −0.1 to about −1.0.

* * * * *